US009290478B2

(12) United States Patent
Saxty et al.

(10) Patent No.: US 9,290,478 B2
(45) Date of Patent: Mar. 22, 2016

(54) SUBSTITUTED QUINOXALINES AS FGFR KINASE INHIBITORS

(75) Inventors: Gordon Saxty, Cambridge (GB); Christopher William Murray, Cambridge (GB); Valerio Berdini, Cambridge (GB); Gilbert Ebai Besong, Bad Duerkheim (DE); Christopher Charles Frederick Hamlett, Cambridge (GB); Steven John Woodhead, San Diego, CA (US); Yannick Aime Eddy Ligny, Sotteville-les-Rouen (FR); Patrick René Angibaud, Fontaine Bellenger (FR)

(73) Assignee: ASTEX THERAPEUTICS LTD, Cambridge (GB)

( * ) Notice: Subject to any disclaimer, the term of this patent is extended or adjusted under 35 U.S.C. 154(b) by 0 days.

(21) Appl. No.: 13/990,193

(22) PCT Filed: Nov. 29, 2011

(86) PCT No.: PCT/GB2011/052356
§ 371 (c)(1),
(2), (4) Date: May 29, 2013

(87) PCT Pub. No.: WO2012/073017
PCT Pub. Date: Jun. 7, 2012

(65) Prior Publication Data
US 2013/0267525 A1 Oct. 10, 2013

Related U.S. Application Data

(60) Provisional application No. 61/417,744, filed on Nov. 29, 2010.

(30) Foreign Application Priority Data

Nov. 29, 2010 (GB) .................................. 1020179.6

(51) Int. Cl.
| | |
|---|---|
| A61K 31/498 | (2006.01) |
| C07D 241/40 | (2006.01) |
| C07D 403/04 | (2006.01) |
| C07D 401/14 | (2006.01) |
| C07D 403/14 | (2006.01) |

(52) U.S. Cl.
CPC ............ *C07D 403/04* (2013.01); *C07D 401/14* (2013.01); *C07D 403/14* (2013.01)

(58) Field of Classification Search
CPC ............................ A61K 31/498; C07D 241/40
USPC .................. 514/249; 544/353; 548/364.7
See application file for complete search history.

(56) References Cited

U.S. PATENT DOCUMENTS

| | | | |
|---|---|---|---|
| 2,940,972 | A | 6/1960 | Roch |
| 4,666,828 | A | 5/1987 | Gusella |
| 4,683,202 | A | 7/1987 | Mullis |
| 4,801,531 | A | 1/1989 | Frossard |
| 5,192,659 | A | 3/1993 | Simons |
| 5,272,057 | A | 12/1993 | Smulson et al. |
| 5,700,823 | A | 12/1997 | Hirth et al. |
| 5,882,864 | A | 3/1999 | An et al. |
| 6,218,529 | B1 | 4/2001 | An et al. |
| 6,271,231 | B1 | 8/2001 | Bergstrand et al. |
| 6,331,555 | B1 | 12/2001 | Hirth et al. |
| 9,145,367 | B2 | 9/2015 | Tazi et al. |
| 9,221,804 | B2 | 12/2015 | Leonard et al. |
| 2003/0207886 | A1 | 11/2003 | Plücker et al. |
| 2005/0261307 | A1 | 11/2005 | Cai et al. |
| 2005/0272728 | A1 | 12/2005 | Altenbach et al. |
| 2005/0272736 | A1 | 12/2005 | Altenbach et al. |
| 2007/0123494 | A1 | 5/2007 | Seipelt et al. |
| 2007/0149484 | A1 | 6/2007 | Claus et al. |
| 2008/0116789 | A1 | 5/2008 | Yamaguchi et al. |
| 2009/0054304 | A1 | 2/2009 | Herbert et al. |

(Continued)

FOREIGN PATENT DOCUMENTS

| | | | |
|---|---|---|---|
| CA | 2 524 525 | A1 | 12/2004 |
| CA | 2 524 948 | A1 | 12/2004 |

(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Hackam, et al. JAMA, 296(14), 2006, 1731-1732.*
Zhou, Wenjun et al., "A Structure-Guided Approach to Creating Covalent FGFR Inhibitors", *Chemistry & Biology*, vol. 17, pp. 285-295 (2010).

(Continued)

*Primary Examiner* — Douglas M Willis
(74) *Attorney, Agent, or Firm* — Heslin Rothenberg Farley & Mesiti P.C.

(57) ABSTRACT

The invention relates to new quinoxaline derivative compounds of formula (I),

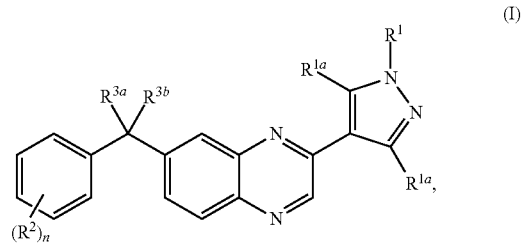

to pharmaceutical compositions comprising said compounds, to processes for the preparation of said compounds and to the use of said compounds in the treatment of diseases, e.g. cancer.

20 Claims, No Drawings

(56) References Cited

U.S. PATENT DOCUMENTS

| | | |
|---|---|---|
| 2009/0221591 A1 | 9/2009 | Hartmann et al. |
| 2010/0234347 A1 | 9/2010 | Dollinger et al. |
| 2013/0072457 A1 | 3/2013 | Saxty et al. |
| 2014/0288053 A1 | 9/2014 | Berdini et al. |
| 2014/0296236 A1 | 10/2014 | Berdini et al. |
| 2015/0031669 A1 | 1/2015 | Woodhead et al. |
| 2015/0057293 A1 | 2/2015 | Angibaud et al. |
| 2015/0291589 A1 | 10/2015 | Saxty et al. |

FOREIGN PATENT DOCUMENTS

| | | |
|---|---|---|
| CN | 1128496A A | 8/1996 |
| CN | 102036963 A | 4/2011 |
| EP | 0544445 A2 | 6/1993 |
| EP | 1001946 B1 | 5/2000 |
| EP | 1 990 342 A1 | 11/2008 |
| EP | 2 332 939 A1 | 6/2011 |
| EP | 2650293 A1 | 10/2013 |
| JP | 2003213463 A | 7/2003 |
| JP | 2008530030 A | 8/2008 |
| WO | 95/19169 A2 | 7/1995 |
| WO | 99/17759 A2 | 4/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 2003/055491 A1 | 7/2003 |
| WO | 2004/006355 A2 | 1/2004 |
| WO | 2004/030635 A2 | 4/2004 |
| WO | 2004/043950 A1 | 5/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/047244 A2 | 5/2005 |
| WO | 2005/054201 A1 | 6/2005 |
| WO | 2005/061463 A1 | 7/2005 |
| WO | 2006/066361 A1 | 6/2006 |
| WO | 2006084338 A1 | 8/2006 |
| WO | 2006/092430 A1 | 9/2006 |
| WO | 2006124354 A2 | 11/2006 |
| WO | 2007/003419 A1 | 1/2007 |
| WO | 2007054556 A1 | 5/2007 |
| WO | 2007/075567 A1 | 7/2007 |
| WO | 2007/125405 A2 | 11/2007 |
| WO | 2007/132227 A1 | 11/2007 |
| WO | 2008/003702 A2 | 1/2008 |
| WO | 2008/076278 A2 | 6/2008 |
| WO | 2008/078091 A1 | 7/2008 |
| WO | 2008/082198 A1 | 7/2008 |
| WO | 2008080015 A2 | 7/2008 |
| WO | 2008/138878 A2 | 11/2008 |
| WO | 2008/141065 A1 | 11/2008 |
| WO | 2008540535 A | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009/064835 A1 | 5/2009 |
| WO | 2009/137378 A2 | 11/2009 |
| WO | 2009/141386 A1 | 11/2009 |
| WO | 2010059771 A1 | 5/2010 |
| WO | 2010/084152 A1 | 7/2010 |
| WO | 2010129570 A1 | 11/2010 |
| WO | 2011/026579 A1 | 3/2011 |
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | WO 2012/073017 | * 6/2012 |
| WO | 2012/104776 A1 | 8/2012 |
| WO | 2012/118492 A1 | 9/2012 |
| WO | 2012/148540 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013/179033 A1 | 12/2013 |
| WO | 2013/179034 A1 | 12/2013 |
| WO | 2014/174307 A1 | 10/2014 |
| WO | 2015144803 A1 | 10/2015 |
| WO | 2015144804 A1 | 10/2015 |
| WO | 2015144808 A1 | 10/2015 |

OTHER PUBLICATIONS

Garuti, L., et al., Irreversible Protein Kinase Inhibitors, *Current Medicinal Chemistry*, vol. 18, No. 20, Jul. 1, 2011, pp. 2981-2994.

International Search Report for PCT/GB2011/052356 dated Feb. 27, 2012.

Search Report for GB1020179.6 dated Feb. 9, 2011.

Yan, Lin et al. "An efficient synthesis of quinoxaline derivatives from 4-chloro-4-deoxy-α-D-galactose and their cytotoxic activities", *Bioorganic & Medicinal Chemistry Letters*, vol. 17, No. 3, 2006, pp. 609-612.

Thompson, Andrew M. et al. "Synthesis and Structure—Activity Relationships of 7-Substituted 3-(2,6-Dichlorophenyl)-1,6-napthyridin-2(1H)-ones as Selective Inhibitors of pp60$^{c-src}$", *Journal of Medicinal Chemistry*, vol. 43, No. 16, 2000, pp. 3134-3147.

Berge, Stephen M. et al. "Pharmaceutical Salts", *Journal of Pharmaceutical Sciences*, vol. 66, No. 1, 1977, pp. 1-19.

Deady, Leslie W. "Ring Nitrogen Oxidation of Amino Substituted Nitrogen Heterocycles with m-Chloroperbenzoic Acid", *Synthetic Communications*, vol. 7(8), 1977, pp. 509-514.

Knights, Victoria et al. "De-regulated FGF receptors as therapeutic targets in cancer", *Pharmacology & Therapeutics*, 2010; vol. 125(1), pp. 105-117.

Korc, M. et al. "The Role of Fibroblast Growth Factors in Tumor Growth", *Current Cancer Drug Targets*, vol. 9(5), 2009, pp. 639-651.

Angerer, Lynne M. et al. "Demonstration of Tissue-Specific Gene Expression by in Situ Hybridization", *Methods in Enzymology*, vol. 152, 1987, pp. 649-661.

Deprimo, Samuel E. et al. "Expression profiling of blood samples from an SU5416 Phase III metastatic colorectal cancer clinical trial: a novel strategy for biomarker identification", *BMC Cancer*, vol. 3, 2003; pp. 1-12.

Orre, Maxine and Rogers, Peter A. W. "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.

Elsevier, Avendaño, C. et al., "Drugs That Inhibit Signalling Pathways for Tumor Cell Growth and Proliferation", *Medicinal Chemistry of Anticancer Drugs*, pp. 251-305 (2008).

"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).

V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).

"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).

(56) References Cited

OTHER PUBLICATIONS

Lima, L.M., et al., "Bioisosterism: A Useful Strategy for Molecular Modification and Drug Design", *Current Medical Chemistry*, vol. 12(1), pp. 23-49 (2005).

Patani, G.A., et al., "Bioisosterism: A Rational Approach in Drug Design", *Chem. Rev.* vol. 96, pp. 3147-3176 (1996).

Dorwald, F.Z., Side Reactions in Organic Synthesis: A Guide to Successful Synthesis Design, Weinheim:WILEY-VCH Verlag GmbH & Co. KGaA, 2005, ISBN: 3-527-31021.5.

Dieci, M.V., et al., Fibrolast Growth Factor Receptor Inhibitors as a Cancer Treatment: From a Biologic Rationale to Medical Perspectives, Cancer Discovery, vol. 3, No. 3, pp. 264-279 (Feb. 2013).

Gallick, G.E., et al., Small-molecule protein tyrosine kinase inhibitors for the treatment of metastatic prostate cancer, Future Medicinal Chemistry, vol. 4, No. 1, pp. 107-119 (Jan. 2012).

Study to Assess the Relative Bioavailability of Orally Administered JNJ-42756493 Tablet Versus JNJ-42756493 Capsule in Healthy Participants, ClinicalTrials.gov, pp. 1-4 (2014).

Matsuda, Y., et al., Fibrolast Growth Factor Receptor-2 IIIc as a Novel Molecular Target in Colorectal Cancer, Current Colorectal Cancer Reports, vol. 10, No. 1, pp. 20-26 (2014).

Carneiro, B.A., et al., Engineering therapeutic targets in bladder cancer, Cancer Treatment Revies, vol. 41, No. 2, pp. 170-178 (2015).

Fujita, M., et al., Generation of Formaldehyde by Pharmaceutical Excipients and Its Absorption by Meglumine, Chem. Pharm. Bull, vol. 57, No. 10, pp. 1096-1099 (2009).

Adcock, J., et al., Diversity oriented synthesis: substitution at C5 in unreactive pyrimidines by Claisen rearrangement and reactivity in nucleophilic substition at C2 and C4 in pteridines and pyrido[2,3-d]pyrimidines, Tetrahedron, vol. 67, pp. 3226-3237 (2011).

\* cited by examiner

SUBSTITUTED QUINOXALINES AS FGFR KINASE INHIBITORS

CROSS REFERENCE TO RELATED APPLICATIONS

This application is a national stage filing under section 371 of International Application No. PCT/GB2011/052356, filed on Nov. 29, 2011, and published in English on Jun. 7, 2012, as WO/2012/073017, and claims priority to British Application No. 1020179.6 filed on Nov. 29, 2010, and to U.S. Provisional Application No. 61/417,744, filed on Nov. 29, 2010. The entire disclosures of each of the prior applications are hereby incorporated herein by reference.

FIELD OF THE INVENTION

The invention relates to new quinoxaline derivative compounds, to pharmaceutical compositions comprising said compounds, to processes for the preparation of said compounds and to the use of said compounds in the treatment of diseases, e.g. cancer.

SUMMARY OF THE INVENTION

According to a first aspect of the invention there is provided compounds of formula (I):

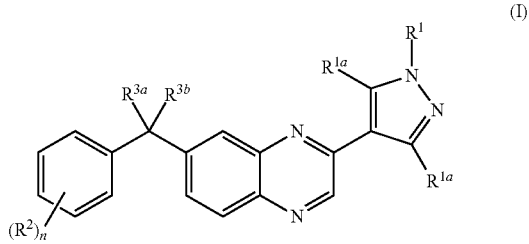

including any tautomeric or stereochemically isomeric form thereof, wherein
n represents an integer equal to 0, 1, 2, 3 or 4;
$R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;
each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms;
each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —$NR^7R^8$, $C_{1-4}$alkyl substituted with —C(=O)—$NR^7R^8$, $C_{1-4}$alkoxy substituted with —$NR^7R^8$, $C_{1-4}$alkoxy substituted with —C(=O)—$NR^7R^8$, —$NR^7R^8$ and —C(=O)—$NR^7R^8$; or when two $R^2$ groups are attached to adjacent carbon atoms they may be taken together to form a radical of formula:
—O—(C($R^{17}$)$_2$)$_p$—O—;
—X—CH=CH—; or
—X—CH=N—; wherein $R^{17}$ represents hydrogen or fluorine, p represents 1 or 2 and X represents O or S;
$R^{3a}$ represents —$NR^{10}R^{11}$, hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$;
$R^{3b}$ represents hydrogen or hydroxyl; provided that if $R^{3a}$ represents —$NR^{10}R^{11}$, then $R^{3b}$ represents hydrogen; or
$R^{3a}$ and $R^{3b}$ are taken together to form =O, to form =$NR^{10}$, to form cyclopropyl together with the carbon atom to which they are attached, to form =CH—$C_{0-4}$alkyl substituted with $R^{3c}$, or to form

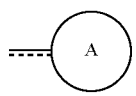

wherein ring A is a monocyclic 5 to 7 membered saturated heterocycle containing one heteroatom selected from N, O or S, said heteroatom not being positioned in alpha position of the double bond, wherein ring A is optionally being substituted with cyano, $C_{1-4}$alkyl, hydroxy$C_{1-4}$alkyl, $H_2N$—$C_{1-4}$alkyl, $(C_{1-4}$alkyl)NH—$C_{1-4}$alkyl, $(C_{1-4}$alkyl)$_2$N—$C_{1-4}$alkyl, halo$C_{1-4}$alkyl)NH—$C_{1-4}$alkyl, $C_{1-4}$alkoxy$C_{1-4}$alkyl, —C(=O)—$NH_2$, —C(=O)—NH($C_{1-4}$alkyl), —C(=O)—N($C_{1-4}$alkyl)$_2$;

$R^{3c}$ represents hydrogen, hydroxyl, $C_{1-6}$alkoxy, $R^9$, —$NR^{10}R^{11}$, cyano, —C(=O)—$C_{1-6}$alkyl or —CH(OH)—$C_{1-6}$alkyl;

$R^4$ and $R^5$ each independently represent hydrogen, $C_{1-6}$alkyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O or S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O or S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O or S;

$R^{10}$ and $R^{11}$ each independently represent hydrogen, carboxyl, $C_{1-6}$alkyl, cyano$C_{1-6}$alkyl, $C_{1-6}$alkyl substituted with —$NR^{14}R^{15}$, $C_{1-6}$alkyl substituted with —C(=O)—$NR^{14}R^{15}$, halo$C_{1-6}$alkyl, hydroxy$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —C(=O)—$R^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, —C(=O)—$C_{1-6}$alkyl, $C_{1-6}$alkoxy, or —$NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

$R^{16}$ represents hydroxyl, halogen, cyano, $C_{1-4}$alkyl, $C_{1-4}$alkoxy, —$NR^{14}R^{15}$ or —C(=O)$NR^{14}R^{15}$;

the N-oxides thereof, the pharmaceutically acceptable salts thereof or the solvates thereof.

In one embodiment there is provided compounds of formula (I$^0$):

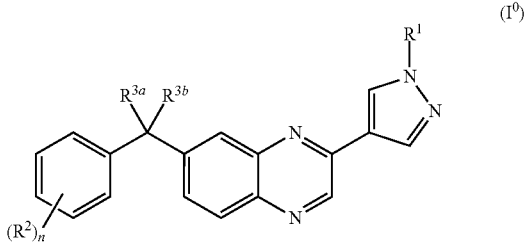

(I⁰)

including any tautomeric or stereochemically isomeric form thereof, wherein n represents an integer equal to 0, 1, 2, 3 or 4;

$R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;

each $R^2$ is independently selected from halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —$NR^7R^8$, $C_{1-4}$alkyl substituted with —C(=O)—$NR^7R^8$, $C_{1-4}$alkoxy substituted with —$NR^7R^8$, $C_{1-4}$alkoxy substituted with —C(=O)—$NR^7R^8$, —$NR^7R^8$ or —C(=O)—$NR^7R^8$;

$R^{3a}$ represents —$NR^{10}R^{11}$, hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo$C_{1-6}$alkyl, hydroxy$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups, $C_{2-6}$alkenyl substituted with $C_{1-6}$alkoxy, $C_{2-6}$alkynyl substituted with $C_{1-6}$alkoxy, $C_{1-6}$alkyl substituted with $R^9$, $C_{1-6}$alkyl substituted with hydroxyl and —C(=O)—$R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$;

$R^{3b}$ represents hydrogen or hydroxyl; provided that if $R^{3a}$ represents —$NR^{10}R^{11}$, then $R^{3b}$ represents hydrogen; or $R^{3a}$ and $R^{3b}$ are taken together to form =O, to form =$NR^{10}$, to form cyclopropyl together with the carbon atom to which they are attached, to form =CH—$C_{0-4}$alkyl substituted with $R^{3c}$, or to form

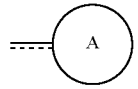

wherein ring A is a monocyclic 5 to 7 membered saturated heterocycle containing one heteroatom selected from N, O or S, said heteroatom not being positioned in alpha position of the double bond, wherein ring A is optionally being substituted with cyano, $C_{1-4}$alkyl, hydroxy$C_{1-4}$alkyl, $H_2N$—$C_{1-4}$alkyl, ($C_{1-4}$alkyl)NH—$C_{1-4}$alkyl, ($C_{1-4}$alkyl)$_2$N—$C_{1-4}$alkyl, halo$C_{1-4}$alkyl)NH—$C_{1-4}$alkyl, $C_{1-4}$alkoxy$C_{1-4}$alkyl, —C(=O)—$NH_2$, —C(=O)—NH($C_{1-4}$alkyl), —C(=O)—N($C_{1-4}$alkyl)$_2$;

$R^{3c}$ represents hydrogen, hydroxyl, $C_{1-6}$alkoxy, $R^9$, —$NR^{10}R^{11}$, cyano, —C(=O)—$C_{1-6}$alkyl or —CH(OH)—$C_{1-6}$alkyl;

$R^4$ and $R^5$ each independently represent hydrogen, $C_{1-6}$alkyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O or S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—NR$^{14}$R$^{15}$;

R$^7$ and R$^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

R$^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —NR$^{14}$R$^{15}$, —C(=O)—NR$^{14}$R$^{15}$, $C_{1-4}$alkyl substituted with —NR$^{14}$R$^{15}$, $C_{1-4}$alkyl substituted with —C(=O)—NR$^{14}$R$^{15}$, $C_{1-4}$alkoxy, —S(=O)$_2$—$C_{1-4}$alkyl, —S(=O)$_2$-halo$C_{1-4}$alkyl, —S(=O)$_2$—NR$^{14}$R$^{15}$, $C_{1-4}$alkyl substituted with —S(=O)$_2$—NR$^{14}$R$^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—NR$^{14}$R$^{15}$, R$^{13}$, —C(=O)—R$^{13}$, $C_{1-4}$alkyl substituted with R$^{13}$, phenyl optionally substituted with R$^{16}$, phenyl$C_{1-6}$alkyl wherein the phenyl is optionally substituted with R$^{16}$, a 5 or 6-membered aromatic monocyclic heterocyclyl containing at least one heteroatom selected from N, O or S wherein said heterocyclyl is optionally substituted with R$^{16}$;

or when two of the substituents of R$^9$ are attached to the same atom, they may be taken together to form a 4 to 7-membered saturated monocyclic heterocyclyl containing at least one heteroatom selected from N, O or S;

R$^{10}$ and R$^{11}$ each independently represent hydrogen, $C_{1-6}$alkyl, cyano$C_{1-6}$alkyl, $C_{1-6}$alkyl substituted with —NR$^{14}$R$^{15}$, halo$C_{1-6}$alkyl, hydroxy$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, R$^6$, $C_{1-6}$alkyl substituted with R$^6$, —C(=O)—R$^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—NR$^{14}$R$^{15}$;

R$^{12}$ represents hydrogen or $C_{1-4}$alkyl optionally substituted with $C_{1-4}$alkoxy;

R$^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, —C(=O)—$C_{1-6}$alkyl, $C_{1-6}$alkoxy, or —NR$^{14}$R$^{15}$;

R$^{14}$ and R$^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

R$^{16}$ represents hydroxyl, halogen, cyano, $C_{1-4}$alkyl, $C_{1-4}$alkoxy, —NR$^{14}$R$^{15}$ or —C(=O)NR$^{14}$R$^{15}$;

the N-oxides thereof, the pharmaceutically acceptable salts thereof or the solvates thereof.

WO 2008/141065, WO 2004/006355, WO2006/092430, WO2008/003702, WO01/68047, WO2005/007099, WO2004/098494, WO2009/141386, WO 2004/030635, WO 2008/141065, WO 2011/026579, WO 2011/028947, WO2011/135376 and WO 00/42026 which each disclose a series of heterocyclyl derivatives.

DETAILED DESCRIPTION OF THE INVENTION

Unless the context indicates otherwise, references to formula (I°) or (I) in all sections of this document (including the uses, methods and other aspects of the invention) include references to all other sub-formula (e.g. I-a, I'-a, I''-a, I'''-a, I-b, I'-b, I''-b, I'''-b, I-c, I'-c, I''-c, I'''-c, I-d, I'-d, I''-d, I'''-d, I-e), sub-groups, preferences, embodiments and examples as defined herein.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term 'halo' or 'halogen' as used herein refers to a fluorine, chlorine, bromine or iodine atom.

The term '$C_{1-4}$alkyl', or '$C_{1-6}$alkyl' as used herein as a group or part of a group refers to a linear or branched saturated hydrocarbon group containing from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{0-4}$alkyl' as used herein as a group or part of a group refers to a linear or branched saturated hydrocarbon group containing from 0 to 4 carbon atoms, wherein when the alkyl group contains zero carbon atoms it is absent, but the R$^{3a}$ substitutent will still be present as required to complete the valency of the atom to which it is attached.

The term '$C_{2-4}$alkenyl' or '$C_{2-6}$alkenyl' as used herein as a group or part of a group refers to a linear or branched hydrocarbon group containing from 2 to 4 or 2 to 6 carbon atoms and containing a carbon carbon double bond.

The term '$C_{2-4}$alkynyl' or '$C_{2-6}$alkynyl' as used herein as a group or part of a group refers to a linear or branched hydrocarbon group having from 2 to 4 or 2 to 6 carbon atoms and containing a carbon carbon triple bond.

The term '$C_{1-4}$alkoxy' or '$C_{1-6}$alkoxy' as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{1-4}$alkoxy$C_{1-4}$alkyl' or '$C_{1-6}$alkoxy$C_{1-6}$alkyl' as used herein as a group or part of a group refers to a $C_{1-4}$alkyl-O—$C_{1-4}$alkyl group or a $C_{1-6}$alkyl-O—$C_{1-6}$alkyl group wherein $C_{1-4}$alkyl and $C_{1-6}$alkyl are as defined herein. Examples of such groups include methoxyethyl, ethoxyethyl, propoxymethyl, butoxypropyl, and the like.

The term '$C_{3-8}$cycloalkyl' as used herein refers to a saturated monocyclic hydrocarbon ring of 3 to 8 carbon atoms.

Examples of such groups include cyclopropyl, cyclobutyl, cyclopentyl, cyclohexyl, cycloheptyl or cyclooctyl and the like.

The term '$C_{3-8}$cycloalkenyl' as used herein refers to a monocyclic hydrocarbon ring of 3 to 8 carbon atoms having a carbon carbon double bond.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$alkyl' or 'hydroxy$C_{1-6}$alkyl' therefore include monohydroxy$C_{1-4}$alkyl, monohydroxy$C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The term 'halo$C_{1-4}$alkyl' or 'halo$C_{1-6}$alkyl' therefore include monohalo$C_{1-4}$alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo$C_{1-4}$alkyl or halo$C_{1-6}$alkyl may have one, two, three or more halogens. Examples of such groups include fluoroethyl, fluoromethyl, trifluoromethyl or trifluoroethyl and the like.

The term 'hydroxyhalo$C_{1-4}$alkyl' or 'hydroxyhalo$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group and one or more than one hydrogen atom is replaced with a halogen. The term 'hydroxyhalo$C_{1-4}$alkyl' or 'hydroxyhalo$C_{1-6}$alkyl' therefore refers to a $C_{1-4}$alkyl or $C_{1-6}$alkyl group wherein one, two, three or more hydrogen atoms are replaced with a hydroxyl group and one, two, three or more hydrogen atoms are replaced with a halogen.

The term 'hydroxy$C_{1-4}$alkoxy' or 'hydroxy$C_{1-6}$alkoxy' as used herein as a group or part of a group refers to an —O—$C_{1-4}$alkyl group or an —O—$C_{1-6}$alkyl group wherein the $C_{1-4}$alkyl and $C_{1-6}$alkyl group is as defined above and one or more than one hydrogen atom of the $C_{1-4}$alkyl or $C_{1-6}$alkyl group is replaced with a hydroxyl group. The term 'hydroxy$C_{1-4}$alkoxy' or 'hydroxy$C_{1-6}$alkoxy' therefore include monohydroxy$C_{1-4}$alkoxy, monohydroxy$C_{1-6}$alkoxy and also polyhydroxy$C_{1-4}$alkoxy and polyhydroxy$C_{1-6}$alkoxy. There may be one, two, three or more hydrogen atoms replaced with a hydroxyl group so the hydroxy$C_{1-4}$alkoxy or hydroxy$C_{1-6}$alkoxy may have one, two, three or more hydroxyl groups. Examples of such groups include hydroxymethoxy, hydroxyethoxy, hydroxypropoxy and the like.

The term 'halo$C_{1-4}$alkoxy' or 'halo$C_{1-6}$alkoxy' as used herein as a group or part of a group refers to a —O—$C_{1-4}$alkyl group or a —O—$C_{1-6}$ alkyl group as defined herein wherein one or more than one hydrogen atom is replaced with a halogen. The terms 'halo$C_{1-4}$alkoxy' or 'halo$C_{1-6}$alkoxy' therefore include monohalo$C_{1-4}$alkoxy, monohalo$C_{1-6}$alkoxy and also polyhalo$C_{1-4}$alkoxy and polyhalo$C_{1-6}$alkoxy. There may be one, two, three or more hydrogen atoms replaced with a halogen, so the halo$C_{1-4}$alkoxy or halo$C_{1-6}$alkoxy may have one, two, three or more halogens. Examples of such groups include fluoroethyloxy, difluoromethoxy or trifluoromethoxy and the like.

The term 'hydroxyhalo$C_{1-4}$alkoxy' as used herein as a group or part of a group refers to an —O—$C_{1-4}$alkyl group wherein the $C_{1-4}$alkyl group is as defined herein and wherein one or more than one hydrogen atom is replaced with a hydroxyl group and one or more than one hydrogen atom is replaced with a halogen. The term 'hydroxyhalo$C_{1-4}$alkoxy' therefore refers to a —O—$C_{1-4}$alkyl group wherein one, two, three or more hydrogen atoms are replaced with a hydroxyl group and one, two, three or more hydrogen atoms are replaced with a halogen.

The term 'halo$C_{1-4}$alkoxy$C_{1-4}$alkyl' as used herein as a group or part of a group refers to a $C_{1-4}$alkyl-O—$C_{1-4}$alkyl group wherein $C_{1-4}$alkyl is as defined herein and wherein in one or both of the $C_{1-4}$alkyl groups one or more than one hydrogen atom is replaced with a halogen. The term 'halo$C_{1-4}$alkoxy$C_{1-4}$alkyl' therefore refers to a $C_{1-4}$alkyl-O—$C_{1-4}$alkyl group wherein in one or both of the $C_{1-4}$alkyl groups one, two, three or more hydrogen atoms are replaced with a halogen and wherein $C_{1-4}$ alkyl is as defined herein. Preferably, in one of the $C_{1-4}$alkyl groups one or more than one hydrogen atom is replaced with a halogen. Preferably, halo$C_{1-4}$alkoxy$C_{1-4}$alkyl means $C_{1-4}$alkyl substituted with halo$C_{1-4}$alkoxy.

The term 'hydroxyhalo$C_{1-4}$alkoxy$C_{1-4}$alkyl' as used herein refers to a $C_{1-4}$alkyl-O—$C_{1-4}$alkyl group wherein $C_{1-4}$alkyl is as defined herein and wherein in one or both of the $C_{1-4}$alkyl groups one or more than one hydrogen atom is replaced with a hydroxyl group and one or more than one hydrogen atom is replaced with a halogen. The terms 'hydroxyhalo$C_{1-4}$alkoxy$C_{1-4}$alkyl' therefore refers to a $C_{1-4}$alkyl-O—$C_{1-4}$alkyl group wherein in one or both of the $C_{1-4}$alkyl groups one, two, three or more hydrogen atoms are replaced with a hydroxyl group and one, two, three or more hydrogen atoms are replaced with a halogen and wherein $C_{1-4}$alkyl is as defined herein.

The term 'hydroxy$C_{2-6}$alkenyl' as used herein refers to a $C_{2-6}$alkenyl group wherein one or more than one hydrogen atom is replaced with a hydroxyl group and wherein $C_{2-6}$alkenyl is as defined herein.

The term 'hydroxy$C_{2-6}$alkynyl' as used herein refers to a $C_{2-6}$alkynyl group wherein one or more than one hydrogen atom is replaced with a hydroxyl group and wherein $C_{2-6}$alkynyl is as defined herein.

The term phenyl$C_{1-6}$alkyl as used herein refers to a $C_{1-6}$alkyl group as defined herein which is substituted with one phenyl group.

The term cyano$C_{1-4}$alkyl or cyano$C_{1-6}$alkyl as used herein refers to a $C_{1-4}$alkyl or $C_{1-6}$alkyl group as defined herein which is substituted with one cyano group.

The term "heterocyclyl" as used herein shall, unless the context indicates otherwise, include both aromatic and non-aromatic ring systems. Thus, for example, the term "heterocyclyl group" includes within its scope aromatic, non-aromatic, unsaturated, partially saturated and fully saturated heterocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to heterocyclyl groups, the heterocyclyl ring can, unless the context indicates otherwise, be optionally substituted (i.e. unsubstituted or substituted) by one or more substituents as discussed herein.

The heterocyclyl groups can be heteroaryl groups having from 5 to 12 ring members, more usually from 5 to 10 ring members. The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 0, 1, 2 or 3 ring heteroatoms;
  c) a pyrimidine ring fused to a 5- or 6-membered ring containing 0, 1 or 2 ring heteroatoms;
  d) a pyrrole ring fused to a 5- or 6-membered ring containing 0, 1, 2 or 3 ring heteroatoms;
  e) a pyrazole ring fused to a 5- or 6-membered ring containing 0, 1 or 2 ring heteroatoms;
  f) an imidazole ring fused to a 5- or 6-membered ring containing 0, 1 or 2 ring heteroatoms;
  g) an oxazole ring fused to a 5- or 6-membered ring containing 0, 1 or 2 ring heteroatoms;
  h) an isoxazole ring fused to a 5- or 6-membered ring containing 0, 1 or 2 ring heteroatoms;
  i) a thiazole ring fused to a 5- or 6-membered ring containing 0, 1 or 2 ring heteroatoms;
  j) an isothiazole ring fused to a 5- or 6-membered ring containing 0, 1 or 2 ring heteroatoms;
  k) a thiophene ring fused to a 5- or 6-membered ring containing 0, 1, 2 or 3 ring heteroatoms;
  l) a furan ring fused to a 5- or 6-membered ring containing 0, 1, 2 or 3 ring heteroatoms;
  m) a cyclohexyl ring fused to a 5- or 6-membered ring containing 1, 2 or 3 ring heteroatoms; and
  n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), indoline and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The heterocylic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof. Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

The heterocyclyl groups can each be unsubstituted or substituted by one or more substituent groups. For example, heterocyclyl groups can be unsubstituted or substituted by 1, 2, 3 or 4 substituents. Where the heterocyclyl group is monocyclic or bicyclic, typically it is unsubstituted or has 1, 2 or 3 substituents.

The term 'aryl' as used herein refers to carbocyclyl aromatic groups including phenyl, naphthyl, indenyl, and tetrahydronaphthyl groups.

In one embodiment $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —NR$^4$R$^5$, $C_{1-6}$alkyl substituted with —C(=O)—NR$^4$R$^5$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}$R$^{15}$, R$^6$, $C_{1-6}$alkyl substituted with R$^6$, $C_{1-6}$alkyl substituted with —C(=O)—R$^6$, hydroxy$C_{1-6}$alkyl substituted with R$^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(OC$_{1-6}$alkyl)$_2$.

In one embodiment $R^1$ represents hydrogen, $C_{1-6}$alkyl, $C_{2-4}$alkenyl, hydroxy$C_{1-6}$alkyl, halo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —NR$^4$R$^5$, $C_{1-6}$alkyl substituted with —C(=O)—NR$^4$R$^5$, —S(=O)$_2$—$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —NH—S(=O)$_2$—$C_{1-6}$alkyl, R$^6$, $C_{1-6}$alkyl substituted with R$^6$, $C_{1-6}$alkyl substituted with —C(=O)—R$^6$, hydroxy$C_{1-6}$alkyl substituted with R$^6$, or $C_{1-6}$alkyl substituted with —Si(CH$_3$)$_3$.

In one embodiment $R^1$ represents hydrogen.

In one embodiment $R^1$ represents $C_{1-6}$alkyl. $R^1$ may represent —CH$_3$, —CD$_3$, —CH$_2$CH$_3$, —CH$_2$CH$_2$CH$_3$, —CH$_2$CH(CH$_3$)$_2$, —CH(CH$_3$)$_2$, —CH$_2$CH(CH$_3$)$_2$. In one embodiment $R^1$ represents —CH$_3$. In another embodiment $R^1$ represents —CD$_3$.

In one embodiment $R^1$ represents $C_{2-4}$alkenyl. $R^1$ may represent —CH$_2$—CH=CH$_2$.

In one embodiment $R^1$ represents hydroxy$C_{1-6}$alkyl. $R^1$ may represent —CH$_2$CH$_2$OH, —CH$_2$C(CH$_3$)$_2$OH or CH$_2$CHOHCH$_2$OH.

In one embodiment $R^1$ represents halo$C_{1-6}$alkyl. $R^1$ may represent —CH$_2$CH$_2$F, CH$_2$CH$_2$CH$_2$C$_1$ or CH$_2$CH$_2$Br.

In one embodiment $R^1$ represents $C_{1-6}$alkoxy$C_{1-6}$alkyl wherein each $C_{1-6}$alkyl may optionally be substituted with one or two hydroxyl groups. $R^1$ may represent —CH$_2$CH$_2$OCH$_3$.

In one embodiment $R^1$ represents $C_{1-6}$alkyl substituted with —NR$^4$R$^5$.

In one embodiment when $R^1$ represents $C_{1-6}$alkyl substituted with —NR$^4$R$^5$, R$^4$ and R$^5$ each represent hydrogen. $R^1$ may represent —CH$_2$CH$_2$NH$_2$ or —CH$_2$CH$_2$CH$_2$NH$_2$.

In another embodiment when $R^1$ represents $C_{1-6}$alkyl substituted with —NR$^4$R$^5$, one of R$^4$ and R$^5$ represents hydrogen and the other represents $C_{1-6}$alkyl, for example —CH$_3$. $R^1$ may represent —CH$_2$CH$_2$NHCH$_3$.

In another embodiment when $R^1$ represents $C_{1-6}$alkyl substituted with —NR$^4$R$^5$, one of R$^4$ and R$^5$ represents hydrogen and the other represents —S(=O)$_2$—NR$^{14}$R$^{15}$ where R$^{14}$ and R$^{15}$ each represent $C_{1-4}$alkyl optionally substituted with hydroxyl, for example —CH$_3$. $R^1$ may represent —CH$_2$CH$_2$NHS(=O)$_2$N(CH$_3$)$_2$.

In another embodiment when $R^1$ represents $C_{1-6}$alkyl substituted with —NR$^4$R$^5$, one of R$^4$ and R$^5$ represents hydrogen and the other represents —S(=O)$_2$—$C_{1-6}$alkyl. $R^1$ may represent —CH$_2$CH$_2$NHS(=O)$_2$CH$_3$.

In one embodiment $R^1$ represents $C_{1-6}$alkyl substituted with —C(=O)—NR$^4$R$^5$.

In one embodiment when R$^1$ represents C$_{1-6}$alkyl substituted with —C(=O)—NR$^4$R$^5$, R$^4$ and R$^5$ each represent C$_{1-6}$alkyl, for example —CH$_3$. R$^1$ may represent —CH$_2$C(=O)N(CH$_3$)$_2$.

In another embodiment when R$^1$ represents C$_{1-6}$alkyl substituted with —C(=O)—NR$^4$R$^5$, one of R$^4$ and R$^5$ represents hydrogen and the other represents C$_{1-6}$alkyl, for example —CH$_3$. R$^1$ may represent —CH$_2$C(=O)NHCH$_3$ or —C(CH$_3$)$_2$C(=O)NHCH$_3$.

In another embodiment when R$^1$ represents C$_{1-6}$alkyl substituted with —C(=O)—NR$^4$R$^5$, one of R$^4$ and R$^5$ represents hydrogen and the other represents hydroxyC$_{1-6}$alkyl, for example —CH$_2$CH$_2$OH. R$^1$ may represent —C(CH$_3$)$_2$C(=O)NHCH$_2$CH$_2$OH or —CH$_2$C(=O)NHCH$_2$CH$_2$OH.

In another embodiment when R$^1$ represents C$_{1-6}$alkyl substituted with —C(=O)—NR$^4$R$^5$, one of R$^4$ and R$^5$ represents hydrogen and the other represents C$_{1-6}$alkoxyC$_{1-6}$alkyl wherein each C$_{1-6}$alkyl may optionally be substituted with one or two hydroxyl groups, for example —CH$_2$CH$_2$OCH$_3$. R$^1$ may represent —CH$_2$C(=O)NHCH$_2$CH$_2$OCH$_3$ or —C(CH$_3$)$_2$C(=O)NH—CH$_2$CH$_2$OCH$_3$.

In another embodiment when R$^1$ represents C$_{1-6}$alkyl substituted with —C(=O)—NR$^4$R$^5$, one of R$^4$ and R$^5$ represents hydrogen and the other represents C$_{1-6}$alkyl substituted with R$^{13}$. R$^{13}$ may represent a saturated 5 membered monocyclic heterocyclyl containing at least one nitrogen heteroatom, for example pyrrolidine. R$^1$ may represent —CH$_2$—C(=O)—NH—CH$_2$—CH$_2$— (pyrrolidin-1-yl).

In another embodiment when R$^1$ represents C$_{1-6}$alkyl substituted with —C(=O)—NR$^4$R$^5$, one of R$^4$ and R$^5$ represents hydrogen and the other represents C$_{1-6}$alkyl substituted with —S(=O)$_2$—C$_{1-6}$alkyl. R$^1$ may represent —CH$_2$CH$_2$CH$_2$NHCH$_2$CH$_2$—S(=O)$_2$—CH$_3$.

In one embodiment R$^1$ represents —S(=O)$_2$—C$_{1-6}$alkyl. R$^1$ may represent —S(=O)$_2$—CH$_3$.

In one embodiment R$^1$ represents —S(=O)$_2$—NR$^{14}$R$^{15}$. R$^{14}$ and R$^{15}$ may each represent C$_{1-4}$alkyl optionally substituted with hydroxyl, for example R$^{14}$ and R$^{15}$ may both represent —CH$_3$. R$^1$ may represent —S(=O)$_2$—N(CH$_3$)$_2$.

In one embodiment R$^1$ represents C$_{1-6}$alkyl substituted with —S(=O)$_2$—C$_{1-6}$alkyl. R$^1$ may represent —CH$_2$CH$_2$S(=O)$_2$—CH$_3$.

In one embodiment R$^1$ represents C$_{1-6}$alkyl substituted with —NH—S(=O)$_2$—C$_{1-6}$alkyl. R$^1$ may represent —CH$_2$CH$_2$NHS(=O)$_2$—CH$_3$.

In one embodiment R$^1$ represents R$^6$. R$^6$ may represent a saturated 4, 5 or 6 membered monocyclic heterocyclyl containing at least one heteroatom selected from N, O or S, which may optionally be substituted.

In one embodiment when R$^1$ represents R$^6$, R$^6$ represents piperidinyl, for example 4-piperidinyl.

In one embodiment when R$^1$ represents R$^6$, R$^6$ represents tetrahydropyranyl, for example 2-tetrahydropyranyl.

In another embodiment when R$^1$ represents R$^6$, R$^6$ represents azetidinyl substituted by one hydroxyC$_{1-6}$alkyl group. The hydroxyC$_{1-6}$alkyl group may be —CH$_2$CH$_2$OH. R$^6$ may represent

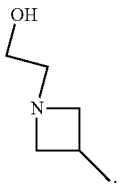

In another embodiment when R$^1$ represents R$^6$, R$^6$ represents piperidinyl substituted by one C$_{1-6}$alkyl-O—C(=O)— group. The C$_{1-6}$alkyl-O—C(=O)— group may be (CH$_3$)$_3$C—O—C(=O)—. R$^6$ may represent 4-piperidinyl substituted on the nitrogen atom with (CH$_3$)$_3$C—O—C(=O)—. In another embodiment when R$^1$ represents R$^6$, R$^6$ represents piperidinyl substituted by one —S(=O)$_2$—C$_{1-6}$alkyl group. The —S(=O)$_2$—C$_{1-6}$alkyl group may be —S(=O)$_2$CH$_3$. R$^6$ may represent 4-piperidinyl substituted on the nitrogen atom with —S(=O)$_2$CH$_3$.

In one embodiment R$^1$ represents C$_{1-6}$alkyl substituted with R$^6$. R$^6$ may represent a saturated 4, 5 or 6 membered monocyclic heterocyclyl containing at least one heteroatom selected from N, O or S, which may optionally be substituted. R$^6$ may represent pyrrolidinyl, thiophenyl, piperidinyl, morpholinyl, piperazinyl, tetrahydropyranyl. R$^1$ may represent methyl or ethyl each substituted with 4-piperidinyl, 4-piperazinyl, 1-pyrrolidinyl or 4-tetrahydropyranyl. R$^1$ may represent propyl substituted with morpholinyl where the morpholinyl is linked to the propyl through the N heteroatom. In another embodiment the heterocyclyl may be substituted by one substituent selected from halogen, C$_{1-6}$alkyl, hydroxyl, hydroxyC$_{1-6}$alkyl, C$_{1-6}$alkoxy, C$_{1-6}$alkyl-O—C(=O)—. The substituent may be —Cl, —CH$_3$, —OH, —CH$_2$CH$_2$OH, —CH$_2$CH$_2$CH$_2$OH, —OCH$_3$, (CH$_3$)$_3$C—O—C(=O)—.

R$^1$ may represent methyl, ethyl or propyl each substituted with 4-piperidinyl substituted on the nitrogen atom with (CH$_3$)$_3$C—O—C(=O)—, 4-piperidinyl substituted on the nitrogen atom with —CH$_3$, 4-piperazinyl substituted on the nitrogen atom with (CH$_3$)$_3$C—O—C(=O)—, 4-piperazinyl substituted on the nitrogen atom with —CH$_2$CH$_2$OH, 4-piperazinyl substituted on the nitrogen atom with —CH$_2$CH$_2$CH$_2$OH, 1-piperidinyl substituted in the 1 position by —OH, or 1-piperidinyl substituted in the 1 position by —O—CH$_3$. In another embodiment the heterocyclyl may be substituted by two substituents selected from hydroxyl, C$_{1-6}$alkoxy, C$_{1-6}$alkyl-O—C(=O)—. The substituent may be —OH, —OCH$_3$, (CH$_3$)$_3$C—O—C(=O)—. R$^1$ may represent methyl substituted with 4-piperidinyl substituted on the nitrogen atom with (CH$_3$)$_3$C—O—C(=O)— and in the 4 position by —OH.

In one embodiment R$^1$ represents C$_{1-6}$alkyl substituted with —C(=O)—R$^6$. R$^6$ may represent a saturated 4, 5 or 6 membered monocyclic heterocyclyl containing at least one heteroatom selected from N, O or S, which may optionally be substituted. R$^6$ may represent piperazinyl or pyrrolidinyl.

In one embodiment when R$^1$ represents C$_{1-6}$alkyl substituted with —C(=O)—R$^6$, R$^6$ represents piperazinyl. R$^1$ may represent —C(CH$_3$)$_2$—C(=O)-(piperazin-4-yl).

In another embodiment when R$^1$ represents C$_{1-6}$alkyl substituted with —C(=O)—R$^6$, R$^6$ represents piperazinyl substituted by one C$_{1-6}$alkyl-O—C(=O)— group, for example (CH$_3$)$_3$C—O—C(=O)—. R$^1$ may represent —C(CH$_3$)$_2$—C(=O)-(piperazin-4-yl) substituted on the nitrogen atom in the 1 position by (CH$_3$)$_3$C—O—C(=O)—.

In another embodiment when R$^1$ represents C$_{1-6}$alkyl substituted with —C(=O)—R$^6$, R$^6$ represents pyrrolidinyl substituted by one hydroxyl group. $R^1$ may represent —CH$_2$—C(=O)-(pyrrolidin-1-yl) substituted in the 3 position by —OH.

In one embodiment $R^1$ represents hydroxyC$_{1-6}$alkyl substituted with $R^6$, $R^6$ may represent a saturated 4, 5 or 6 membered monocyclic heterocyclyl containing at least one heteroatom selected from N, O or S, which may optionally be substituted. $R^6$ may represent piperidinyl, for example 1-piperidinyl. $R^1$ may represent —CH$_2$CHOHCH$_2$-piperidin-1-yl.

In one embodiment $R^1$ represents C$_{1-6}$alkyl substituted with —Si(CH$_3$)$_3$. $R^1$ may represent —CH$_2$Si(CH$_3$)$_3$.

In one embodiment each $R^{1a}$ represents hydrogen.

In one embodiment each $R^2$ is independently selected from halogen, cyano, C$_{1-4}$alkyl, C$_{2-4}$alkenyl, C$_{1-4}$alkoxy, hydroxyC$_{1-4}$alkyl, hydroxyC$_{1-4}$alkoxy, haloC$_{1-4}$alkoxy, C$_{1-4}$alkoxyC$_{1-4}$alkyl, $R^{13}$, C$_{1-4}$alkoxy substituted with $R^{13}$, —C(=O)—R$^{13}$, C$_{1-4}$alkyl substituted with NR$^7$R$^8$, C$_{1-4}$alkoxy substituted with NR$^7$R$^8$, —NR$^7$R$^8$ or —C(=O)—NR$^7$R$^8$.

In one embodiment one or more $R^2$ represents halogen, for example fluorine, chlorine or bromine.

In one embodiment one or more $R^2$ represents cyano.

In one embodiment one or more $R^2$ represents C$_{1-4}$alkyl, for example —CH$_3$.

In one embodiment one or more $R^2$ represents C$_{2-4}$alkenyl, for example —CH=CH$_2$.

In one embodiment one or more $R^2$ represents C$_{1-4}$alkoxy, for example CH$_3$O—, (CH$_3$)$_2$CHO—, CH$_3$CH$_2$O—, CD$_3$O—.

In one embodiment one or more $R^2$ represents hydroxyC$_{1-4}$alkyl, for example —CH$_2$OH.

In one embodiment one or more $R^2$ represents hydroxyC$_{1-4}$alkoxy, for example —OCH$_2$CH$_2$OH.

In one embodiment one or more $R^2$ represents haloC$_{1-4}$alkoxy, for example —OCH$_2$CH$_2$F or —O—CHF$_2$.

In one embodiment one or more $R^2$ represents C$_{1-4}$alkoxyC$_{1-4}$alkyl, for example —CH$_2$CH$_2$OCH$_3$.

In one embodiment one or more $R^2$ represents $R^{13}$. $R^{13}$ may represent a saturated 5 membered monocyclic heterocyclyl containing two oxygen heteroatoms, for example dioxolanyl, particularly 2-dioxolanyl.

In one embodiment one or more $R^2$ represents C$_{1-4}$alkoxy substituted with $R^{13}$. $R^{13}$ may represent C$_{3-8}$cycloalkyl, for example cyclopropyl. One or more $R^2$ may represent —OCH$_2$C$_3$H$_5$.

In one embodiment one or more $R^2$ represents —C(=O)—R$^{13}$. $R^{13}$ may represent a saturated 5 membered monocyclic heterocyclyl containing one nitrogen heteroatom, for example pyrrolidinyl. $R^2$ may represent —C(=O)-(1-pyrrolidinyl).

In one embodiment one or more $R^2$ represents C$_{1-4}$alkyl substituted with —NR$^7$R$^8$. In one embodiment $R^7$ and $R^8$ each represent hydrogen. One or more $R^2$ may represent —CH$_2$NH$_2$. In another embodiment $R^7$ and $R^8$ may each independently represent C$_{1-6}$alkyl, for example —CH$_2$CH$_3$ or —CH$_3$. One or more $R^2$ may represent —CH$_2$N(CH$_2$CH$_3$)$_2$, —CH$_2$N(CH$_3$)$_2$ or —CH$_2$N(CH$_2$CH$_3$)(CH$_3$).

In one embodiment one or more $R^2$ represents C$_{1-4}$alkoxy substituted with —NR$^7$R$^8$. In one embodiment one of $R^7$ and $R^8$ represents hydrogen and the other represents C$_{1-6}$alkyl, for example —CH$_3$. One or more $R^2$ may represent —OCH$_2$CH$_2$NHCH$_3$. In one embodiment $R^7$ and $R^8$ each represent hydrogen. One or more $R^2$ may represent —OCH$_2$CH$_2$NH$_2$.

In one embodiment one or more $R^2$ represents —NR$^7$R$^8$. In one embodiment one of $R^7$ and $R^8$ represents hydrogen and the other represents C$_{1-6}$alkyl, for example —CH$_3$.

In one embodiment one or more $R^2$ represents —C(=O)—NR$^7$R$^8$. In one embodiment one of $R^7$ and $R^8$ represents hydrogen and the other represents C$_{1-6}$alkyl, for example —CH$_3$.

In one embodiment n is 0, 1 or 2.

In one embodiment n is equal to 0.

In one embodiment n is equal to 1. $R^2$ may be at the 3-position. $R^2$ may represent
(i) haloC$_{1-4}$alkoxy, for example —O—CHF$_2$;
(ii) C$_{1-4}$alkoxy, for example CH$_3$O— or (CH$_3$)$_2$CHO—;
(iii) cyano; or
(iv) —NR$^7$R$^8$, for example —NHCH$_3$.

In one embodiment n is equal to 2. One $R^2$ may be at the 3-position and the other may be at the 5-position:
(i) each $R^2$ may represent C$_{1-4}$alkoxy, for example each $R^2$ may be CH$_3$O—, or the $R^2$ at the 3-position may be (CH$_3$)$_2$CHO— and the $R^2$ at the 5-position may be CH$_3$O—, or the $R^2$ at the 3-position may be CH$_3$O— and the $R^2$ at the 5-position may be CD$_3$O—;
(ii) the $R^2$ at the 3-position may represent halogen, for example fluorine, chlorine or bromine, and the $R^2$ at the 5-position may represent C$_{1-4}$alkoxy, for example CH$_3$O—, CD$_3$O— or CH$_3$CH$_2$O—;
(iii) the $R^2$ at the 3-position may represent C$_{1-4}$alkyl, for example —CH$_3$, and the $R^2$ at the 5-position may represent C$_{1-4}$alkoxy, for example CH$_3$O—;
(iv) the $R^2$ at the 3-position may represent cyano, and the $R^2$ at the 5-position may represent C$_{1-4}$alkoxy, for example CH$_3$O—;
(v) the $R^2$ at the 3-position may represent C$_{1-4}$alkyl substituted with NR$^7$R$^8$, for example —CH$_2$NH$_2$ or —CH$_2$N(CH$_3$)$_2$ or —CH$_2$N(CH$_2$CH$_3$)$_2$ or —CH$_2$N(CH$_2$CH$_3$)(CH$_3$), and the $R^2$ at the 5-position may represent C$_{1-4}$alkoxy, for example CH$_3$O—;
(vi) the $R^2$ at the 3-position may represent C$_{1-4}$alkoxy, for example CH$_3$O—, and the $R^2$ at the 5-position may represent —C(=O)—NR$^7$R$^8$, for example —C(=O)NHCH$_3$ or —C(=O)NH$_2$;
(vii) the $R^2$ at the 3-position may represent hydroxyC$_{1-4}$alkoxy, for example —OCH$_2$CH$_2$OH, and the $R^2$ at the 5-position may represent C$_{1-4}$alkoxy, for example CH$_3$O—;
(viii) the $R^2$ at the 3-position may represent —C(=O)—R$^{13}$, for example —C(=O)-(pyrrolidin-1-yl), and the $R^2$ at the 5-position may represent C$_{1-4}$alkoxy, for example CH$_3$O—;
(ix) the $R^2$ at the 3-position may represent C$_{1-4}$alkoxy substituted with $R^{13}$, for example —OCH$_2$C$_3$H$_5$, and the $R^2$ at the 5-position may represent C$_{1-4}$alkoxy, for example CH$_3$O—;
(x) the $R^2$ at the 3-position may represent C$_{1-4}$alkoxy, for example CH$_3$O—, and the $R^2$ at the 5-position may represent C$_{1-4}$alkoxy substituted with NR$^7$R$^8$, for example —OCH$_2$CH$_2$NHCH$_3$ or —OCH$_2$CH$_2$NH$_2$;
(xi) the $R^2$ at the 3-position may represent C$_{1-4}$alkoxy, for example CH$_3$O—, and the $R^2$ at the 5-position may represent C$_{2-4}$alkenyl, for example —CH=CH$_2$;
(xii) the $R^2$ at the 3-position may represent C$_{1-4}$alkoxy, for example CH$_3$O—, and the $R^2$ at the 5-position may represent C$_{1-4}$alkoxyC$_{1-4}$alkyl, for example —CH$_2$CH$_2$OCH$_3$;
(xiii) the $R^2$ at the 3-position may represent $R^{13}$, for example 2-dioxolanyl, and the $R^2$ at the 5-position may represent C$_{1-4}$alkoxy, for example CH$_3$O—;

(xiv) the $R^2$ at the 3-position may represent hydroxy$C_{1-4}$alkoxy, for example —OCH$_2$CH$_2$OH, and the $R^2$ at the 5-position may represent halogen, for example fluorine;

(xv) the $R^2$ at the 3-position may represent halo$C_{1-4}$alkoxy, for example —OCH$_2$CH$_2$F, and the $R^2$ at the 5-position may represent $C_{1-4}$alkoxy, for example CH$_3$O—;

(xvi) the $R^2$ at the 3-position may represent halogen, for example fluorine, and the $R^2$ at the 5-position may represent —C(═O)—NR$^7$R$^8$, for example —C(═O)NHCH$_3$;

(xvii) the $R^2$ at the 3-position may represent $C_{1-4}$alkoxy, for example CH$_3$O—, and the $R^2$ at the 5-position may represent halogen, for example fluorine; or (xviii) the $R^2$ at the 3-position may represent represents hydroxy$C_{1-6}$alkyl, for example —CH$_2$OH, and the $R^2$ at the 5-position may represent $C_{1-4}$alkoxy, for example CH$_3$O—.

In one embodiment n is equal to 2. One $R^2$ may be at the 3-position and the other may be at the 5-position. Each $R^2$ may represent $C_{1-4}$alkoxy, for example each $R^2$ may be CH$_3$O—, (CH$_3$)$_2$CHO—, CH$_3$CH$_2$O—, CD$_3$O—. In one embodiment both $R^2$ are for example CH$_3$O—, or CD$_3$O—. In one embodiment both $R^2$ are CH$_3$O—.

In one embodiment n is equal to 2. One $R^2$ may be at the 4-position and the other may be at the 5-position. Each $R^2$ may represent $C_{1-4}$alkoxy, for example each $R^2$ may be CH$_3$O—.

In one embodiment n is equal to 2. One $R^2$ may be at the 5-position and the other may be at the 6-position. Each $R^2$ may represent $C_{1-4}$alkoxy, for example each $R^2$ may be CH$_3$O—.

In one embodiment n is equal to 2. One $R^2$ may be at the 2-position and the other may be at the 5-position:

(i) each $R^2$ may represent $C_{1-4}$alkoxy, for example each $R^2$ may be CH$_3$O—; or (ii) the $R^2$ at the 2-position may be halogen, for example chlorine, and the $R^2$ at the 5 position may represent $C_{1-4}$alkoxy, for example CH$_3$O—.

In one embodiment n is equal to 3. One $R^2$ may be at the 2-position, one may be at the 3-position and one may be at the 5-position:

(i) the $R^2$ at the 2-position may represent halogen, for example chlorine, the $R^2$ at the 3-position and the 5-position may each represent $C_{1-4}$alkoxy, for example each of these $R^2$ may be CH$_3$O—; or (ii) the $R^2$ at the 2-position may represent $C_{1-4}$alkyl, for example —CH$_3$, the $R^2$ at the 3-position and the 5-position may each represent $C_{1-4}$alkoxy, for example each of these $R^2$ may be CH$_3$O—.

$R^{3a}$ may represent —NR$^{10}$R$^{11}$, hydroxyl, $C_{1-6}$alkyl, hydroxy$C_{1-6}$alkyl, hydroxyhalo$C_{1-6}$alkyl, halo$C_{1-6}$alkyl, $C_{1-6}$alkyl substituted with —C(═O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with R$^9$, $C_{1-6}$alkyl substituted with —NR$^{10}$R$^{11}$, $C_{1-6}$alkyl substituted with hydroxyl and —NR$^{10}$R$^{11}$, $C_{1-6}$alkyl substituted with one or two halogens and —NR$^{10}$R$^{11}$, $C_{1-6}$alkyl substituted with —C(═O)—O—$C_{1-6}$alkyl, $C_{1-6}$alkyl substituted with —O—C(═O)—NR$^{10}$R$^{11}$, $C_{1-6}$alkyl substituted with carboxyl, $C_{1-6}$alkyl substituted with —O—C(═O)—NR$^{10}$R$^{11}$, $C_{1-6}$alkyl substituted with —NR$^{12}$—S(═O)$_2$—$C_{1-6}$alkyl, $C_{1-6}$alkyl substituted with —NR$^{12}$—S(═O)$_2$—NR$^{14}$R$^{15}$, $C_{1-6}$alkyl substituted with hydroxyl and R$^9$, —$C_{1-6}$alkyl-C(R$^{12}$)═N—O—R$^{12}$, $C_{1-6}$alkyl substituted with —C(═O)—NR$^{10}$R$^{11}$, $C_{1-6}$alkyl substituted with —C(═O)—R$^9$, $C_{2-6}$alkynyl substituted with R$^9$, hydroxy$C_{1-6}$alkoxy, $C_{2-6}$alkenyl, $C_{2-6}$alkynyl, R$^{13}$ or $C_{1-6}$alkyl substituted with $C_{1-6}$alkoxy$C_{1-6}$alkyl-C(═O)—.

In one embodiment $R^{3a}$ is —NR$^{10}$R$^{11}$, hydroxyl, hydroxy$C_{1-6}$alkyl, cyano$C_{1-6}$alkyl, $C_{1-6}$alkyl substituted with —C(═O)—$C_{1-6}$alkyl, $C_{1-6}$alkyl substituted with —C(═O)—O—$C_{1-6}$alkyl, $C_{1-6}$alkyl substituted with R$^9$, $C_{1-6}$alkyl substituted with —NR$^{10}$R$^{11}$, $C_{1-6}$alkyl substituted with hydroxyl and —NR$^{10}$R$^{11}$, $C_{1-6}$alkyl substituted with —C(═O)—NR$^{10}$R$^{11}$.

In one embodiment $R^{3a}$ represents —NR$^{10}$R$^{11}$. In one embodiment one of R$^{10}$ and R$^{11}$ represents hydrogen and the other represents $C_{1-6}$alkyl substituted with —NR$^{14}$R$^{15}$. One of R$^{14}$ and R$^{15}$ may represent hydrogen and the other may represent $C_{1-4}$alkyl. $R^{3a}$ may represent —NHCH$_2$CH$_2$NHCH(CH$_3$)$_2$.

In one embodiment R$^{10}$ and R$^{11}$ each independently represent hydrogen, $C_{1-6}$alkyl, $C_{1-6}$alkyl substituted with —NR$^{14}$R$^{15}$ or halo$C_{1-6}$alkyl.

In one embodiment $R^{3a}$ represents hydroxyl.

In one embodiment $R^{3a}$ represents $C_{1-6}$alkyl. $R^{3a}$ may represent —CH$_3$, —CH$_2$CH$_3$, —CH$_2$CH$_2$CH$_3$ or —CH$_2$CH(CH$_3$)$_2$.

In one embodiment $R^{3a}$ represents hydroxy$C_{1-6}$alkyl. $R^{3a}$ may represent —CH$_2$CH$_2$OH, —CH$_2$CH$_2$CH$_2$OH, —CH$_2$CHOHCH$_3$, —CH$_2$CHOHCH$_2$CH$_3$, —CH$_2$CHOHCH(CH$_3$)$_2$, —CH$_2$CH$_2$C(OH)(CH$_3$)$_2$, —CH$_2$CHOHCH$_2$OH or —CH$_2$C(CH$_3$)$_2$OH. In one embodiment $R^{3a}$ represents —CH$_2$CH$_2$OH.

In one embodiment $R^{3a}$ represents halo$C_{1-6}$alkyl. $R^{3a}$ may represent —CH$_2$CH$_2$CH$_2$Cl or —CH$_2$CH$_2$CH$_2$CH$_2$Cl.

In one embodiment $R^{3a}$ represents hydroxyhalo$C_{1-6}$alkyl, for example $R^{3a}$ may represent —CH$_2$CHOHCF$_3$.

In one embodiment $R^{3a}$ represents $C_{1-6}$alkyl substituted with —C(═O)—$C_{1-6}$alkyl, for example $R^{3a}$ may represent CH$_3$—C(═O)—CH$_2$—, (CH$_3$)$_2$CH—C(═O)—CH$_2$—. In one embodiment $R^{3a}$ represents CH$_3$—C(═O)—CH$_2$—.

In one embodiment $R^{3a}$ represents $C_{1-6}$alkoxy$C_{1-6}$alkyl wherein each $C_{1-6}$alkyl may optionally be substituted with one or two hydroxyl groups. $R^{3a}$ may represent —CH$_2$CH$_2$OCH$_3$, —CH$_2$CH$_2$OCH$_2$CH$_3$ or —CH$_2$CHOHCH$_2$OCH$_3$.

In one embodiment $R^{3a}$ represents $C_{1-6}$alkyl substituted with R$^9$.

In one embodiment when $R^{3a}$ represents $C_{1-6}$alkyl substituted with R$^9$, R$^9$ represents optionally substituted $C_{3-8}$cycloalkyl, for example cyclopropyl or cyclopentyl. $R^{3a}$ may represent —CH$_2$—C$_3$H$_5$ or —CH$_2$C$_5$H$_9$.

In one embodiment where the $C_{3-8}$cycloalkyl is cyclopropyl it is substituted by one hydroxy$C_{1-4}$alkyl, for example —CH$_2$OH.

In another embodiment where the $C_{3-8}$cycloalkyl is cyclopropyl it is substituted by one $C_{1-6}$alkyl-O—C(═O)—, for example CH$_3$CH$_2$—O—C(═O)—.

In one embodiment when $R^{3a}$ represents $C_{1-6}$alkyl substituted with R$^9$, R$^9$ represents an optionally substituted aromatic 5 membered monocyclic heterocyclyl containing a nitrogen and an oxygen heteroatom, for example isoxazolyl. In one embodiment the heterocyclyl is substituted with one or two $C_{1-4}$alkyl groups, for example —CH$_3$ groups. $R^{3a}$ may represent methyl substituted with 5-isoxazoyl substituted in the 3 position with —CH$_3$ or methyl substituted with 3-isoxazoyl substituted in the 5 position with —CH$_3$.

In one embodiment when $R^{3a}$ represents $C_{1-6}$alkyl substituted with R$^9$, R$^9$ represents an optionally substituted saturated 6 membered monocyclic heterocyclyl containing a nitrogen and an oxygen heteroatom, for example morpholinyl. R$^3$ may represent ethyl or propyl substituted by 4-morpholinyl.

In one embodiment the heterocyclyl is substituted with one or two $C_{1-4}$alkyl groups, for example —$CH_3$ groups. $R^{3a}$ may represent ethyl or propyl substituted by 4-morpholinyl substituted in the 2 and 6 positions by —$CH_3$.

In another embodiment the heterocyclyl is substituted with phenyl$C_{1-6}$alkyl, wherein the phenyl is optionally substituted with $R^{16}$, for example —$CH_2$—$C_6H_5$. $R^3$ may represent methyl substituted by 2-morpholinyl substituted in the 4 position by —$CH_2$—$C_6H_5$.

In one embodiment when $R^{3a}$ represents $C_{1-6}$alkyl substituted with $R^9$, $R^9$ represents a saturated or an aromatic 3, 4, 5 or 6 membered monocyclic heterocyclyl containing one or two oxygen heteroatoms, for example ethylene oxide, trimethylene oxide, tetrahydrofuranyl, dioxolanyl, tetrahydropyranyl or furanyl. $R^{3a}$ may be methyl substituted with 2-tetrahydrofuranyl, 2-dioxolane, ethylene oxide, 2-furanyl or 4-tetrahydropyranyl.

In one embodiment when $R^{3a}$ represents $C_{1-6}$alkyl substituted with $R^9$, $R^9$ represents a saturated or an aromatic 3, 4, 5 or 6 membered monocyclic heterocyclyl containing one or two oxygen heteroatoms, for example oxiranyl (ethylene oxide, epoxide). The heterocyclyl may be substituted by $C_{1-4}$alkyl. $R^{3a}$ may be

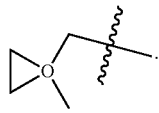

In one embodiment when $R^{3a}$ represents $C_{1-6}$alkyl substituted with $R^9$, $R^9$ represents an optionally substituted 4 membered heterocyclyl containing one oxygen heteroatom, for example oxetanyl, and the heterocyclyl may be substituted with one $C_{1-4}$alkyl group, for example —$CH_3$. $R^{3a}$ may be methyl substituted with 3-oxetanyl substituted in the 3 position by —$CH_3$.

In one embodiment when $R^{3a}$ represents $C_{1-6}$alkyl substituted with $R^9$, $R^9$ represents an optionally substituted aromatic 6 membered monocyclic heterocycle containing one or two nitrogen heteroatoms, for example pyridinyl or pyrazinyl. $R^{3a}$ may represent methyl substituted with 3-pyridinyl or 2-pyrazinyl.

In one embodiment when $R^{3a}$ represents $C_{1-6}$alkyl substituted with $R^9$, $R^9$ represents an optionally substituted aromatic 6 membered monocyclic heterocyclyl containing one nitrogen heteroatom, for example pyridinyl, substituted with one halogen, for example chlorine or bromine. $R^{3a}$ may represent methyl substituted with 3-pyridinyl substituted in the 6 position by chlorine or 2-pyridinyl substituted in the 6 position by bromine.

In one embodiment when $R^{3a}$ represents $C_{1-6}$alkyl substituted with $R^9$, $R^9$ represents an optionally substituted saturated 6 membered monocyclic heterocyclyl containing two nitrogen heteroatoms, for example piperazinyl substituted with $R^{13}$, for example said $R^{13}$ representing piperidinyl being substituted with one $C_{1-4}$alkyl-C(=O)—, for example —C(=O)—$CH_3$. $R^{3a}$ may represent ethyl substituted with 1-piperazinyl substituted in the 4 position with 4-piperidinyl substituted in the 1 position with —C(=O)—$CH_3$.

In one embodiment when $R^{3a}$ represents $C_{1-6}$alkyl substituted with $R^9$, $R^9$ represents a partially saturated 6 membered monocyclic heterocyclyl containing one nitrogen heteroatom which may optionally be substituted. $R^{3a}$ may represent ethyl or propyl substituted with 1,2,3,6-tetrahydropyridine.

In another embodiment when $R^{3a}$ represents $C_{1-6}$alkyl substituted with $R^9$, $R^9$ represents an optionally substituted saturated 4 membered monocyclic heterocyclyl containing one nitrogen heteroatom, for example azetidinyl. The heterocyclyl may be substituted for example with one or two halogens, for example fluorine. $R^{3a}$ may represent propyl substituted with 1-azetidinyl substituted in the 3 position by two fluorines. The heterocyclyl may also be substituted with one hydroxyl group. $R^{3a}$ may represent propyl substituted by 1-azetidinyl substituted in the 3 position by one —OH.

In another embodiment when $R^{3a}$ represents $C_{1-6}$alkyl substituted with $R^9$, $R^9$ represents a saturated 5 membered monocyclic heterocyclyl containing one nitrogen heteroatom, for example pyrrolidinyl. $R^{3a}$ may represent ethyl or propyl substituted with 1-pyrrolidinyl or 2-pyrrolidinyl. The heterocyclyl may be substituted. For example the heterocyclyl is substituted with:

a) one or two halogens, for example fluorine. $R^{3a}$ may represent propyl substituted with 1-pyrrolidinyl substituted in the 3 position with one or two fluorines;
b) one halo$C_{1-4}$alkyl, for example —$CH_2Cl$. $R^{3a}$ may represent propyl substituted with 1-pyrrolidinyl substituted in the 2 position with —$CH_2Cl$;
c) one hydroxyl group. $R^{3a}$ may represent ethyl or propyl substituted with 1-pyrrolidinyl substituted in the 3 position with —OH;
d) one =O group. $R^{3a}$ may represent ethyl or propyl substituted with 1-pyrrolidinyl substituted in the 2 position with =O;
e) one —S(=O)$_2$—$C_{1-4}$alkyl group and the $C_{1-4}$alkyl may be —$CH_3$. $R^{3a}$ may represent propyl substituted with 1-pyrrolidinyl substituted in the 3 position with —S(=O)$_2$—$CH_3$;
f) one —$NR^{14}R^{15}$ group. In one embodiment $R^{14}$ and $R^{15}$ each represent hydrogen. $R^3$ may represent ethyl or propyl substituted with 1-pyrrolidinyl substituted in the 3 position with —$NH_2$. In another embodiment $R^{14}$ and $R^{15}$ each independently represent $C_{1-4}$alkyl optionally substituted with hydroxyl, for example —$CH_3$. $R^3$ may represent ethyl substituted with 1-pyrrolidinyl substituted in the 3 position with —N($CH_3$)$_2$. In another embodiment one of $R^{14}$ and $R^{15}$ is hydrogen and the other is $C_{1-4}$alkyl optionally substituted with hydroxyl, for example —$CH_3$. $R^3$ may represent propyl substituted with 1-pyrrolidinyl substituted in the 3 position with —$NHCH_3$;
g) one or two $C_{1-4}$alkyl groups, for example —$CH_3$ or —CH($CH_3$)$_2$. $R^{3a}$ may represent ethyl or propyl substituted with 1-pyrrolidinyl substituted in the 2 position with —$CH_3$, 1-pyrrolidinyl substituted in the 2 and the 5 position with —$CH_3$ or 1-pyrrolidinyl substituted in the 2 position with two —$CH_3$;
h) one carboxyl group. $R^{3a}$ may represent ethyl substituted with 1-pyrrolidinyl substituted in the 2 position with —C(=O)OH;
i) one hydroxy$C_{1-4}$alkyl, for example —$CH_2OH$, —C($CH_3$)$_2OH$ or —$CH_2CH_2OH$. $R^{3a}$ may represent ethyl or propyl substituted with 1-pyrrolidinyl substituted in the 2 position with —$CH_2OH$;
j) $R^{13}$. In one embodiment $R^{13}$ represents a saturated 6-membered monocyclic heterocyclyl containing one nitrogen heteroatom. In another embodiment $R^{13}$ represents a saturated 6-membered monocyclic heterocyclyl containing one nitrogen and one oxygen heteroatom. In a further embodiment $R^{13}$ represents a saturated 6-membered monocyclic heterocyclyl containing one nitrogen and one oxygen heteroatom, and the heterocyclyl is substituted, for example substituted with two $C_{1-6}$alkyl groups, for example two —CH$_3$ groups. R$^{3a}$ may represent propyl substituted with 1-pyrrolidinyl substituted in the 3 position by 1-piperidinyl, or propyl substituted with 1-pyrrolidinyl substituted in the 3 position by 4-morpholinyl substituted in positions 2 and 6 by —CH$_3$;

k) one cyano group. R$^{3a}$ may represent ethyl or propyl substituted with 1-pyrrolidinyl substituted in the 3 position with —CN;

l) one cyanoC$_{1-4}$alkyl, for example —CH$_2$CN. R$^3$ may represent propyl substituted with 1-pyrrolidinyl substituted in the 2 position with —CH$_2$CN;

m) one C$_{1-4}$alkyl substituted with —NH—S(=O)$_2$-haloC$_{1-4}$alkyl, for example —CH$_2$NH—S(=O)$_2$—CF$_3$. R$^{3a}$ may represent propyl substituted with 1-pyrrolidinyl substituted in the 2 position with —CH$_2$NH—S(=O)$_2$—CF$_3$; or n) one C$_{1-6}$alkyl-O—C(=O)—, for example (CH$_3$)$_3$C—O—C(=O)— or CH$_3$—O—C(=O)—. R$^{3a}$ may represent methyl or ethyl substituted by 2-pyrrolidinyl substituted in the 1 position by (CH$_3$)$_3$C—O—C(=O)— or substituted by 1-pyrrolidinyl substituted in the 2 position by CH$_3$—O—C(=O)—.

In another embodiment when R$^{3a}$ represents ethyl substituted with R$^9$, R$^9$ represents a saturated 5 membered monocyclic heterocyclyl containing one nitrogen heteroatom, for example 1-pyrrolidinyl, and the pyrrolidinyl is substituted with one =O group in the 2 position.

In another embodiment when R$^{3a}$ represents C$_{1-6}$alkyl substituted with R$^9$, R$^9$ represents a saturated 6 membered monocyclic heterocyclyl containing one nitrogen heteroatom, for example piperidinyl. R$^{3a}$ may represent methyl, ethyl or propyl substituted by 4-piperidinyl or 1-piperidinyl. The heterocyclyl may be substituted. For example the heterocyclyl is substituted with:

a) one or two halogens, for example fluorine. R$^{3a}$ may represent ethyl substituted with 1-piperidinyl substituted in the 4 position with two fluorines;

b) one hydroxyl group. R$^{3a}$ may represent methyl or ethyl substituted with 1-piperidinyl substituted in the 4 position with one —OH or 4-piperidinyl substituted in the 4 position with one —OH;

c) one —NR$^{14}$R$^{15}$ group. In one embodiment R$^{14}$ and R$^{15}$ each represent hydrogen. R$^{3a}$ may represent ethyl substituted with 1-piperidinyl substituted at the 3 position or the 4 position with —NH$_2$. In another embodiment R$^{14}$ and R$^{15}$ each independently represent C$_{1-4}$alkyl optionally substituted with hydroxyl, for example —CH$_3$. R$^{3a}$ may represent ethyl substituted with 1-piperidinyl substituted in the 4 position with —N(CH$_3$)$_2$;

d) one or two C$_{1-4}$alkyl groups, for example —CH$_3$ or —CH(CH$_3$)$_2$. R$^{3a}$ may represent methyl, ethyl or propyl substituted with 1-piperidinyl substituted in the 2 position with —CH$_3$, 1-piperidinyl substituted in the 2 and the 6 position with —CH$_3$, 4-piperidinyl substituted in the 1 position with —CH(CH$_3$)$_2$, 4-piperidinyl substituted in the 1 position with —CH$_3$, 1-piperidinyl substituted in the 3 and the 5 position with —CH$_3$;

e) one hydroxyC$_{1-4}$alkyl, for example —CH$_2$OH, —C(CH$_3$)$_2$OH or —CH$_2$CH$_2$OH. R$^{3a}$ may represent ethyl substituted with 1-piperidinyl substituted in the 4 position with —C(CH$_3$)$_2$OH, 1-piperidinyl substituted in the 4 position with —CH$_2$CH$_2$OH; 1-piperidinyl substituted in the 4 position with —CH$_2$OH;

f) one cyano group. R$^{3a}$ may represent ethyl or propyl substituted with 1-piperidinyl substituted in the 3 position with —CN;

g) one C$_{1-6}$alkyl-O—C(=O)—, for example CH$_3$CH$_2$—O—C(=O)—, (CH$_3$)$_3$C—O—C(=O)— or CH$_3$—O—C(=O)—. R$^{3a}$ may represent methyl or ethyl substituted with 1-piperidinyl substituted in the 4 position with CH$_3$CH$_2$—O—C(=O)—, 4-piperidinyl substituted in the 1 position with (CH$_3$)$_3$C—O—C(=O)—;

h) one C$_{1-6}$alkyl-O—C(=O)—, for example (CH$_3$)$_3$C—O—C(=O)—, and one hydroxyl group. R$^{3a}$ may represent methyl substituted with 4-piperidinyl substituted in the 4 position with —OH and in the 1 position with (CH$_3$)$_3$C—O—C(=O)—;

i) one C$_{1-6}$alkyl-O—C(=O)—, for example (CH$_3$)$_3$C—O—C(=O)—, and one C$_{1-4}$alkoxy group, for example —OCH$_3$. R$^{3a}$ may represent methyl substituted with 4-piperidinyl substituted in the 4 position with —OCH$_3$ and in the 1 position with (CH$_3$)$_3$C—O—C(=O)—;

j) one C$_{1-4}$alkoxy group, for example —OCH$_3$. R$^{3a}$ may represent methyl or ethyl substituted with 1-piperidinyl substituted in the 4 position with —OCH$_3$ or 4-piperidinyl substituted in the 4 position with —OCH$_3$;

k) one haloC$_{1-4}$alkyl group, for example —CF$_3$. R$^{3a}$ may represent propyl substituted with 1-piperidinyl substituted in the 4 position with —CF$_3$; or l) one —C(=O)—NR$^{14}$R$^{15}$ where R$^{14}$ and R$^{15}$ both represent hydrogen. R$^{3a}$ may represent ethyl substituted with 1-piperidinyl substituted in the 3 position with —C(=O)—NH$_2$.

In another embodiment when R$^{3a}$ represents C$_{1-6}$alkyl substituted with R$^9$, R$^9$ represents a bicyclic heterocyclyl containing a benzene ring fused to a 5- or 6-membered ring containing 1, 2 or 3 ring heteroatoms. In one embodiment the bicyclic heterocyclyl contains a benzene ring fused to a 5-membered ring containing 1 ring heteroatom. In one embodiment the ring heteroatom is a nitrogen heteroatom. In one embodiment the bicyclic heterocyclyl is substituted with two =O groups on the 5-membered ring containing one ring heteroatom. R$^{3a}$ may represent ethyl, propyl or butyl substituted with isoindolyl-1,3,-dione (e.g. isoindol-2-yl-1,3-dione, also known as phtalimidyl).

In one embodiment when R$^{3a}$ represents C$_{1-6}$alkyl (for example ethyl or propyl) substituted with R$^9$, R$^9$ represents an optionally substituted monocyclic heterocyclyl containing at least one heteroatom selected from N, O or S. In one embodiment R$^9$ represents a 4, 5 or 6 membered monocyclic saturated heterocycle substituted with two substituents which are attached to the same atom and which are taken together to form a 4 to 7-membered saturated monocyclic heterocyclyl containing at least one heteroatom selected from N, O or S; For example R$^{3a}$ may represent ethyl substituted with 2-oxa-6-aza-spiro[3.3]heptane or R$^{3a}$ may represent ethyl substituted with 1-piperidyl substituted on the 4 position by 1,4-dioxolane e.g. to form 1,4-dioxa-8-aza-spiro[4.5]decane.

In another embodiment when R$^{3a}$ represents C$_{1-6}$alkyl substituted with R$^9$, R$^9$ represents an optionally substituted aromatic 5 membered monocyclic heterocyclyl containing one sulphur heteroatom, for example thiophenyl. R$^{3a}$ may represent methyl substituted with 2-thiophenyl. In one embodiment the aromatic 5 membered monocyclic heterocyclyl containing one sulphur heteroatom is substituted with one chlorine. R$^{3a}$ may represent methyl substituted with 2-thiophenyl substituted in the 5 position with chlorine.

In another embodiment when R$^{3a}$ represents C$_{1-6}$alkyl substituted with R$^9$, R$^9$ represents an optionally substituted aromatic 5 membered monocyclic heterocyclyl containing one sulphur and one nitrogen heteroatom, for example thiazolyl. The 5-membered heterocyclyl may be substituted with for example one C$_{1-4}$alkyl, for example —CH$_3$. R$^{3a}$ may represent methyl substituted with 4-thiazolyl substituted in the 2 position with —CH$_3$.

In another embodiment when $R^{3a}$ represents $C_{1-6}$alkyl substituted with $R^9$, $R^9$ represents a saturated 6 membered monocyclic heterocyclyl containing two nitrogen heteroatoms, for example piperazinyl. $R^{3a}$ may represent ethyl or propyl substituted with 1-piperazinyl. The heterocyclyl may be substituted. For example the heterocyclyl is substituted with:
a) one $C_{1-4}$alkyl-C(=O)—, for example $CH_3$—C(=O)—. $R^{3a}$ may represent ethyl substituted with 1-piperazinyl substituted in the 4 position with $CH_3$—C(=O)—;
b) one hydroxy$C_{1-4}$alkyl, for example —$CH_2CH_2OH$. $R^{3a}$ may represent ethyl substituted with 1-piperazinyl substituted in the 4 position with —$CH_2CH_2OH$;
c) one or two $C_{1-4}$alkyl, for example —$CH_3$. $R^{3a}$ may represent ethyl or propyl substituted with 1-piperazinyl substituted in the 3 and 5 positions with —$CH_3$ or 1-piperazinyl substituted in the 4 position with —$CH_3$;
d) one =O. $R^{3a}$ may represent ethyl substituted with 1-piperazinyl substituted in the 3 position with =O; or
e) one —C(=O)—$R^{13}$. $R^{13}$ may be $C_{3-8}$cycloalkyl, for example cyclopropyl. $R^{3a}$ may represent ethyl substituted with 1-piperazinyl substituted in the 4 position with —C(=O)—$C_3H_5$.

In another embodiment when $R^{3a}$ represents $C_{1-6}$alkyl substituted with $R^9$, $R^9$ represents an aromatic 5 membered monocyclic heterocyclyl containing four nitrogen heteroatoms, for example tetrazolyl. $R^3$ may represent ethyl substituted with 5-tetrazolyl.

In another embodiment when $R^{3a}$ represents $C_{1-6}$alkyl substituted with $R^9$, $R^9$ represents an aromatic 5 membered monocyclic heterocyclyl containing one oxygen and two nitrogen heteroatoms, for example 1,3,4-oxadiazolyl. The heterocyclyl may be substituted. For example the heterocyclyl may be substituted with one —$NR^{14}R^{15}$ group, where each of $R^{14}$ and $R^{15}$ is hydrogen. Alternatively one of $R^{14}$ and $R^{15}$ may be hydrogen and the other may represent $C_{1-4}$alkyl optionally substituted with hydroxyl, for example —$CH_2CH_2OH$. $R^{3a}$ may represent methyl substituted with 2-(1,3,4-oxadiazolyl) substituted in the 5 position with —$NH_2$ or 2-(1,3,4-oxadiazoyl) substituted in the 5 position with —NH—$CH_2CH_2OH$.

In another embodiment when $R^{3a}$ represents $C_{1-6}$alkyl substituted with $R^9$, $R^9$ represents an optionally substituted aromatic 5 membered monocyclic heterocyclyl containing two nitrogen heteroatoms, for example pyrazolyl or imidazolyl. $R^{3a}$ may represent methyl, ethyl or propyl substituted with 1-pyrazoyl or 2-imidazoyl. The heterocyclyl may be substituted. For example the heterocyclyl may be substituted with one or two $C_{1-4}$alkyl, for example —$CH_3$ or —$CH_2CH_3$. $R^{3a}$ may represent methyl, ethyl or propyl substituted with 1-imidazolyl substituted in the 2 position with —$CH_3$, 3-pyrazolyl substituted in the 1 and 5 positions with —$CH_3$, 1-imidazolyl substituted in the 2 and 5 positions with —$CH_3$, 1-imidazolyl substituted in the 2 and 4 positions with —$CH_3$, 2-imidazolyl substituted in the 1 position with —$CH_3$ or 2-imidazolyl substituted in the 1 position with —$CH_2CH_3$ In one embodiment when $R^{3a}$ represents $C_{1-6}$alkyl substituted with $R^9$, $R^9$ represents an optionally substituted aromatic 5 membered monocyclic heterocyclyl containing two nitrogen heteroatoms, for example imidazolyl. The heterocyclyl may be substituted. For example the heterocyclyl is substituted with —$S(=O)_2$—$NR^{14}R^{15}$. $R^{14}$ and $R^{15}$ may each represent $C_{1-4}$alkyl optionally substituted with a substituent selected from hydroxyl, $C_{1-4}$alkoxy, amino or mono- or di($C_{1-4}$alkyl)amino, for example —$CH_3$. $R^{3a}$ may represent methyl substituted with 2-imidazoyl substituted in the 1 position with —$S(=O)_2$—$N(CH_3)_2$.

In another embodiment when $R^{3a}$ represents $C_{1-6}$alkyl substituted with $R^9$, $R^9$ represents an optionally substituted aromatic 5 membered monocyclic heterocyclyl containing three nitrogen heteroatoms, for example triazolyl. $R^3$ may represent methyl substituted with 4-(1,2,3-triazolyl). The heterocyclyl may be substituted. For example
the heterocyclyl is substituted with
a) one hydroxy$C_{1-4}$alkyl group, for example —$CH_2CH_2OH$. $R^{3a}$ may represent methyl substituted with 4-(1,2,3-triazolyl) substituted in the 1 position with —$CH_2CH_2OH$ or 4-(1,2,3-triazolyl) substituted in the 2 position with —$CH_2OH$;
b) one $C_{1-4}$alkyl substituted with $C_{1-6}$alkyl-O—C(=O)— group, for example —$CH_2$—C(=O)—$OCH_2CH_3$. $R^{3a}$ may represent methyl substituted with 4-(1,2,3-triazolyl) substituted in the 1 position with —$CH_2$—C(=O)—$OCH_2CH_3$.

In another embodiment when $R^{3a}$ represents $C_{1-6}$alkyl substituted with $R^9$, $R^9$ represents a saturated 5 membered monocyclic heterocyclyl containing one nitrogen and one oxygen heteroatom, for example oxazolidinyl. The heterocyclyl may be substituted, for example substituted with one =O. $R^{3a}$ may represent ethyl or propyl substituted with 3-oxazolidinyl substituted in the 2 position with =O.

In another embodiment when $R^{3a}$ represents $C_{1-6}$alkyl substituted with $R^9$, $R^9$ represents a saturated 6 membered monocyclic heterocyclyl containing one nitrogen and one sulphur heteroatom, for example thiomorpholinyl. The heterocyclyl may be substituted, for example substituted with two =O groups on the sulphur heteroatom. $R^{3a}$ may represent propyl substituted with 4-thiomorpholinyl substituted in the 1 position by two =O groups.

In another embodiment when $R^{3a}$ represents $C_{1-6}$alkyl substituted with $R^9$, $R^9$ represents a saturated 7 membered monocyclic heterocyclyl containing two nitrogen heteroatoms, for example homopiperazinyl. $R^{3a}$ may represent ethyl substituted with 1-homopiperazinyl.

In another embodiment when $R^{3a}$ represents $C_{1-6}$alkyl substituted with $R^9$, $R^9$ represents phenyl or naphthyl, in particular phenyl. $R^{3a}$ may represent —$CH_2$—$C_6H_5$. When $R^9$ represents phenyl or naphthyl, in particular phenyl, the phenyl or naphthyl group may be substituted, for example by one chlorine. $R^{3a}$ may represent methyl substituted with phenyl substituted in the 2, 3 or 4 position with chlorine.

In one embodiment $R^{3a}$ represents cyano$C_{1-6}$alkyl, for example —$CH_2CN$, —$CH_2CH_2CN$ or —$CH_2CH_2CH_2CN$. In one embodiment $R^{3a}$ represents —$CH_2CN$ or —$CH_2CH_2CN$.

In one embodiment $R^{3a}$ represents $C_{1-6}$alkyl substituted with hydroxyl, halo or —$NR^{10}R^{11}$. In a further embodiment $R^{3a}$ represents $C_{1-6}$alkyl substituted with hydroxyl or —$NR^{10}R^{11}$. In a yet further embodiment $R^{3a}$ represents $C_{1-6}$alkyl substituted with —$NR^{10}R^{11}$.

In one embodiment when $R^{3a}$ represents $C_{1-6}$alkyl substituted with —$NR^{10}R^{11}$, $R^{10}$ and $R^{11}$ have the following meanings:
a) each of $R^{10}$ and $R^{11}$ represent hydrogen. $R^{3a}$ may represent —$CH_2CH_2NH_2$, —$CH_2CH_2CH_2NH_2$ or —$CH_2CH_2CH_2CH_2NH_2$;
b) one of $R^{10}$ and $R^{11}$ represents hydrogen and the other represents $C_{1-6}$alkyl, for example —$CH_3$, —$CH_2CH_3$ or —$CH(CH_3)_2$. $R^{3a}$ may represent —$CH_2NHCH_3$, —$CH_2CH_2NHCH_3$, —$CH_2CH_2CH_2NHCH_3$, —$CH_2CH_2NHCH_2CH_3$, —$CH_2CH_2NHCH(CH_3)_2$, —CD2-CD2-NHCH(CH$_3$)$_2$ or —$CH_2CH_2CH_2NHCH(CH_3)_2$;

c) each of $R^{10}$ and $R^{11}$ independently represent $C_{1-6}$alkyl, for example —$CH_3$, —$CH_2CH_3$ or —$CH(CH_3)_2$. $R^{3a}$ may represent —$CH_2CH_2N(CH_3)_2$, —$CH_2CH_2N(CH_2CH_3)_2$, —$CH_2CH_2N(CH_2CH_3)(CH(CH_3)_2)$;

d) one of $R^{10}$ and $R^{11}$ represents hydrogen and the other represents halo$C_{1-6}$alkyl, for example —$CH_2CF_3$, —$CH_2CHF_2$ or —$CH_2CH_2F$. $R^{3a}$ may represent —$CH_2CH_2NHCH_2CF_3$, —$CH_2CH_2CH_2NHCH_2CF_3$, —$CH_2CH_2NHCH_2CHF_2$ or —$CH_2CH_2NHCH_2CH_2F$;

e) one of $R^{10}$ and $R^{11}$ represents hydrogen and the other represents —$C(=O)$—$C_{1-6}$alkyl, for example —$C(=O)$-Me. $R^{3a}$ may represent —$CH_2CH_2NH$—$C(=O)$—$CH_3$;

f) one of $R^{10}$ and $R^{11}$ represents hydrogen and the other represents —$S(=O)_2$—$C_{1-6}$alkyl, for example —$S(=O)_2$—$CH_3$, —$S(=O)_2$—$CH_2CH_3$ or —$S(=O)_2$—$CH(CH_3)_2$. $R^{3a}$ may represent —$CH_2CH_2NH$—$S(=O)_2$—$CH_3$, —$CH_2CH_2CH_2NH$—$S(=O)_2$—$CH_3$, —$CH_2CH_2NH$—$S(=O)_2$—$CH_2CH_3$ or —$CH_2CH_2NH$—$S(=O)_2$—$CH(CH_3)_2$;

g) one of $R^{10}$ and $R^{11}$ represents hydrogen and the other represents —$S(=O)_2$—$NR^{14}R^{15}$, where $R^{14}$ and $R^{15}$ each represent $C_{1-4}$alkyl optionally substituted with hydroxyl, for example —$CH_3$. $R^{3a}$ may represent —$CH_2CH_2NH$—$S(=O)_2$—$N(CH_3)_2$ or —$CH_2CH_2CH_2NH$—$S(=O)_2$—$N(CH_3)_2$;

h) one of $R^{10}$ and $R^{11}$ represents hydrogen and the other represents hydroxy$C_{1-6}$alkyl, for example —$CH_2CH_2OH$. $R^{3a}$ may represent —$CH_2CH_2NHCH_2CH_2OH$;

i) one of $R^{10}$ and $R^{11}$ represents hydrogen and the other represents —$C(=O)$-hydroxyhalo$C_{1-6}$alkyl, for example —$C(=O)$—$C(OH)(CH_3)CF_3$. $R^{3a}$ may represent —$CH_2CH_2CH_2NH$—$C(=O)$—$C(OH)(CH_3)CF_3$ or —$CH_2CH_2NH$—$C(=O)$—$C(OH)(CH_3)CF_3$;

j) one of $R^{10}$ and $R^{11}$ represents hydrogen and the other represents —$C(=O)$—$R^6$. $R^6$ may represent $C_{3-8}$cycloalkyl, for example cyclopropyl. $R^{3a}$ may represent —$CH_2CH_2NH$—$C(=O)$—$C_3H_5$. Alternatively, $R^6$ may represent a saturated 6-membered monocyclic heterocyclyl containing one nitrogen heteroatom, for example piperidinyl. The heterocyclyl may be substituted, for example substituted by one $C_{1-6}$alkyl group, for example —$CH_3$ to form N-methyl piperidinyl. $R^{3a}$ may represent —$CH_2CH_2NH$—$C(=O)$-(piperidin-3-yl) where the piperidinyl is substituted at the 1 position by —$CH_3$;

k) one of $R^{10}$ and $R^{11}$ represents hydrogen and the other represents cyano$C_{1-6}$alkyl, for example —$CH_2CH_2CN$. $R^{3a}$ may represent —$CH_2CH_2NHCH_2CH_2CN$;

l) one of $R^{10}$ and $R^{11}$ represents hydrogen and the other represents $R^6$. $R^6$ may represent $C_{3-8}$cycloalkyl, for example cyclopropyl or cyclopentyl, or $R^6$ may represent a saturated 6-membered monocyclic heterocyclyl containing one nitrogen heteroatom, for example piperidinyl. The heterocyclyl may be substituted, for example substituted with four $C_{1-6}$alkyl groups, for example —$CH_3$ to form for example 2,2,6,6-tetramethyl-piperidinyl. $R^{3a}$ may represent —$CH_2CH_2NHC_3H_5$, —$CH_2CH_2NHC_5H_9$ or —$CH_2CH_2NH$-(2,2,6,6-tetramethyl-piperidin-4-yl). Or, the heterocyclyl may be substituted by one —$S(=O)_2NR^{14}R^{15}$, for example —$S(=O)_2NH_2$. $R^{3a}$ may represent —$CH_2CH_2NH$-(piperidin-4-yl) where the piperidnyl is substituted in the 1 position by —$S(=O)_2NH_2$;

m) one of $R^{10}$ and $R^{11}$ represents hydrogen and the other represents $C_{1-6}$alkyl substituted with $R^6$. $R^6$ may represent $C_{3-8}$cycloalkyl, for example cyclopropyl. $R^{3a}$ may represent —$CH_2CH_2NHCH_2C_3H_5$. Alternatively $R^6$ may represent a saturated, 5-membered monocyclic heterocyclyl containing one oxygen heteroatom. $R^{3a}$ may represent —$CH_2CH_2NHCH_2$—(tetrahydrofuran-2-yl);

n) one of $R^{10}$ and $R^{11}$ represents hydrogen and the other represents —$C(=O)$-halo$C_{1-6}$alkyl, for example —$C(=O)$—$CF_3$. $R^{3a}$ may represent —$CH_2CH_2NHC(=O)$—$CF_3$ or —$CH_2CH_2CH_2NHC(=O)$—$CF_3$;

o) one of $R^{10}$ and $R^{11}$ represents hydrogen and the other represents $C_{1-6}$alkyl substituted with —$Si(CH_3)_3$. $R^{3a}$ may represent —$CH_2CH_2NHCH_2Si(CH_3)_3$;

p) one of $R^{10}$ and $R^{11}$ represents $C_{1-6}$alkyl and the other represents $C_{1-6}$alkyl substituted with $R^6$. $R^6$ may represent phenyl. In one embodiment one of $R^{10}$ and $R^{11}$ represents —$CH_3$ and the other represents —$CH_2$—$C_6H_5$. $R^{3a}$ may represent —$CH_2CH_2N(CH_3)CH_2$—$C_6H_5$.

or q) one of $R^{10}$ and $R^{11}$ represents hydrogen and the other represents $C_{1-6}$alkyl substituted with —$NR^{14}R^{15}$. One of $R^{14}$ and $R^{15}$ may represent hydrogen and the other may represent $C_{1-4}$alkyl, for example —$CH(CH_3)_2$. $R^{3a}$ may represent —$CH_2NHCH_2CH_2NHCH(CH_3)_2$ In one embodiment $R^{10}$ and $R^{11}$ each independently represent hydrogen, $C_{1-6}$alkyl, $C_{1-6}$alkyl substituted with —$NR^{14}R^{15}$ or halo$C_{1-6}$alkyl.

In one embodiment $R^{3a}$ represents —$CH_2CH_2NH_2$, —$CH_2CH_2CH_2NH_2$, —$CH_2NHCH_3$, —$CH_2CH_2NHCH(CH_3)_2$, —$CH_2CH_2N(CH_3)_2$, —$CH_2CH_2NHCH_2CF_3$ or —$CH_2NHCH_2CH_2NHCH(CH_3)_2$.

In one embodiment $R^{10}$ represents hydrogen or $C_{1-6}$alkyl, for example hydrogen, —$CH_3$, —$CH_2CH_3$ or —$CH(CH_3)_2$. In one embodiment $R^{10}$ is hydrogen.

In one embodiment $R^{11}$ represents hydrogen, $C_{1-6}$alkyl, halo$C_{1-6}$alkyl, —$C(=O)$—$C_{1-6}$alkyl, —$S(=O)_2$—$C_{1-6}$alkyl, —$S(=O)_2$—$NR^{14}R^{15}$, hydroxy$C_{1-6}$alkyl, —$C(=O)$-hydroxyhalo$C_{1-6}$alkyl, —$C(=O)$—$R^6$, cyano$C_{1-6}$alkyl, $R^6$, —$C(=O)$—$R^6$, $C_{1-6}$alkyl substituted with $R^6$, —$C(=O)$-halo$C_{1-6}$alkyl, $C_{1-6}$alkyl substituted with —$Si(CH_3)_3$.

In one embodiment $R^{11}$ represents hydrogen, —$CH_3$, —$CH_2CH_3$, —$CH(CH_3)_2$, —$CH_2CF_3$, —$CH_2CHF_2$, —$CH_2CH_2F$, —$C(=O)$—$CH_3$, —$S(=O)_2$—$CH_3$, —$S(=O)_2$—$CH_2CH_3$, —$S(=O)_2$—$CH(CH_3)_2$, —$S(=O)_2$—$N(CH_3)_2$, —$CH_2CH_2OH$, —$C(=O)$—$C(OH)(CH_3)CF_3$, —$C(=O)$— cyclopropyl, —$CH_2CH_2CN$, cyclopropyl, cyclopentyl, 2,2,6,6-tetramethyl-piperidinyl, —$CH_2C_3H_5$, —$CH_2$-tetrahydrofuranyl, —$C(=O)$-(1-methyl-piperidin-3-yl), —$C(=O)$—$CF_3$, —$CH_2Si(CH_3)_3$, —$CH_2$—$C_6H_5$.

In one embodiment $R^{3a}$ represents —$CH_2CH_2NH_2$, —$CH_2CH_2CH_2NH_2$, —$CH_2CH_2CH_2CH_2NH_2$, —$CH_2CH_2NHCH_3$, —$CH_2CH_2CH_2NHCH_3$, —$CH_2CH_2NHCH_2CH_3$, —$CH_2CH_2NHCH(CH_3)_2$, —$CH_2CH_2CH_2NHCH(CH_3)_2$, —$CH_2CH_2N(CH_2CH_3)_2$, —$CH_2CH_2N(CH_2CH_3)(CH(CH_3)_2)$, —$CH_2CH_2CH_2NHCH_2CF_3$, —$CH_2CH_2NHCH_2CHF_2$ or —$CH_2CH_2NHCH_2CH_2F$, —$CH_2CH_2NH$—$C(=O)$—$CH_3$, —$CH_2CH_2NH$—$S(=O)_2$—$CH_3$, $CH_2CH_2CH_2NH$—$S(=O)_2$—$CH_3$, —$CH_2CH_2NH$—$S(=O)_2$—$CH_2CH_3$, —$CH_2CH_2NH$—$S(=O)_2$—$CH(CH_3)_2$, —$CH_2CH_2NH$—$S(=O)_2$—$N(CH_3)_2$, —$CH_2CH_2CH_2NH$—$S(=O)_2$—$N(CH_3)_2$, —$CH_2CH_2NHCH_2CH_2OH$, —$CH_2CH_2CH_2NH$—$C(=O)$—$C(OH)(CH_3)CF_3$, —$CH_2CH_2NH$—$C(=O)$—$C(OH)(CH_3)CF_3$, —$CH_2CH_2NH$—$C(=O)$—$C_3H_5$, —$CH_2CH_2NHCH_2CH_2CN$, $CH_2CH_2NHC_3H_5$, —$CH_2CH_2NHC_5H_9$, —$CH_2CH_2$—NHCO-(piperidin-3-yl) where the piperidin-3-yl is substituted in the 1 position with —$CH_3$, —$CH_2CH_2NHCH_2C_3H_5$, —$CH_2CH_2NHCH_2$(tetrahydrofuran-2-yl), —$CH_2CH_2NHC(=O)$—$CF_3$, —$CH_2CH_2CH_2NHC(=O)$—$CF_3$, —$CH_2CH_2NH$-(2,2,6,6- tetramethyl-piperidin-4-yl), —CH$_2$CH$_2$NHCH$_2$Si(CH$_3$)$_3$, —CH$_2$CH$_2$N(CH$_3$)CH$_2$—C$_6$H$_5$.

In one embodiment R$^{3a}$ represents C$_{1-6}$alkyl substituted with hydroxyl and —NR$^{10}$R$^{11}$.

In one embodiment when R$^{3a}$ represents C$_{1-6}$alkyl substituted with hydroxyl and —NR$^{10}$R$^{11}$, each of R$^{10}$ and R$^{11}$ represents hydrogen. R$^{3a}$ may represent —CH$_2$CHOHCH$_2$NH$_2$.

In one embodiment when R$^{3a}$ represents C$_{1-6}$alkyl substituted with hydroxyl and —NR$^{10}$R$^{11}$, one of R$^{10}$ and R$^{11}$ represents hydrogen and the other represents C$_{1-6}$alkyl, for example —CH$_3$, —CH(CH$_3$)$_2$. R$^{3a}$ may represent —CH$_2$C(CH$_3$)(OH)CH$_2$NHCH(CH$_3$)$_2$, —CH$_2$CHOHCH$_2$NHCH$_3$ or —CH$_2$CHOHCH$_2$NHCH(CH$_3$)$_2$. In one embodiment R$^{3a}$ represents —CH$_2$C(CH$_3$)(OH)CH$_2$NHCH(CH$_3$)$_2$.

In one embodiment when R$^{3a}$ represents C$_{1-6}$alkyl substituted with hydroxyl and —NR$^{10}$R$^{11}$, one of R$^{10}$ and R$^{11}$ represents hydrogen and the other represents haloC$_{1-6}$alkyl, for example —CH$_2$CF$_3$. R$^{3a}$ may represent —CH$_2$CHOHCH$_2$NHCH$_2$CF$_3$.

In one embodiment R$^{3a}$ represents C$_{1-6}$alkyl substituted with one or two halo atoms and —NR$^{10}$R$^{11}$. In one embodiment each of R$^{10}$ and R$^{11}$ represents hydrogen. R$^{3a}$ may represent —CH$_2$CHFCH$_2$NH$_2$.

In one embodiment R$^{3a}$ represents C$_{1-6}$alkyl substituted with —C(=O)—O—C$_{1-6}$alkyl. R$^3$ may represent —CH$_2$C(=O)—O—CH$_3$, —CH$_2$C(=O)—O—CH$_2$CH$_3$ or —CH$_2$CH$_2$—C(=O)—O—CH$_2$CH$_3$. In one embodiment R$^{3a}$ represents CH$_2$C(=O)—O—CH$_3$, or —CH$_2$C(=O)—O—CH$_2$CH$_3$.

In one embodiment R$^{3a}$ represents C$_{1-6}$alkyl (for example methyl) substituted with C$_{1-6}$alkoxyC$_{1-6}$alkyl-C(=O)—. R$^{3a}$ represents —CH$_2$—C(=O)—CH$_2$OCH$_3$.

In one embodiment R$^{3a}$ represents C$_{1-6}$alkyl substituted with —C(=O)—NR$^{10}$R$^{11}$. In one embodiment when R$^{3a}$ represents C$_{1-6}$alkyl substituted with —C(=O)—NR$^{10}$R$^{11}$, R$^{10}$ and R$^{11}$ have the following meanings:
a) R$^{10}$ and R$^{11}$ each represent hydrogen. R$^{3a}$ may represent —CH$_2$C(=O)NH$_2$;
b) one of R$^{10}$ and R$^{11}$ represents hydrogen and the other represents C$_{1-6}$alkyl, e.g. —CH$_3$ or —CH(CH$_3$)$_2$. R$^{3a}$ may represent —CH$_2$C(=O)NHCH$_3$ or —CH$_2$C(=O)NHCH(CH$_3$)$_2$;
c) one of R$^{10}$ and R$^{11}$ represents hydrogen and the other represents C$_{1-6}$alkoxyC$_{1-6}$alkyl wherein each C$_{1-6}$alkyl may optionally be substituted with one or two hydroxyl groups, for example —CH$_2$CH$_2$OCH$_3$. R$^{3a}$ may represent —CH$_2$C(=O)—NHCH$_2$CH$_2$OCH$_3$;
d) one of R$^{10}$ and R$^{11}$ represents hydrogen and the other represents C$_{1-6}$alkyl substituted with R$^6$. R$^6$ may be a saturated 5-membered monocyclic heterocycle containing one nitrogen heteroatom, for example pyrrolidinyl. Alternatively R$^6$ may be an aromatic 5-membered monocyclic heterocycle containing two nitrogen heteroatoms, for example imidazolyl. R$^{3a}$ may represent —CH$_2$C(=O)—NH—CH$_2$CH$_2$— (pyrrolidin-1-yl) or —CH$_2$C(=O)—NH—CH$_2$CH$_2$— (imidazol-2-yl);
e) one of R$^{10}$ and R$^{11}$ represents hydrogen and the other represents hydroxyC$_{1-6}$alkyl, for example —CH$_2$CH$_2$OH. R$^{3a}$ may represent —CH$_2$C(=O)—NHCH$_2$CH$_2$OH; or
f) one of R$^{10}$ and R$^{11}$ represents hydrogen and the other represents C$_{1-6}$alkyl substituted with —NR$^{14}$R$^{15}$ where R$^{14}$ and R$^{15}$ are both hydrogen. R$^{3a}$ may represent —CH$_2$C(=O)—NHCH$_2$CH$_2$NH$_2$.

In one embodiment R$^{3a}$ represents —CH$_2$C(=O)NHCH(CH$_3$)$_2$.

In one embodiment R$^{3a}$ represents C$_{1-6}$alkyl substituted with carboxyl. R$^{3a}$ may represent —CH$_2$C(=O)OH or —CH$_2$CH$_2$C(=O)OH.

In one embodiment R$^{3a}$ represents C$_{1-6}$alkyl substituted with —O—C(=O)—NR$^{10}$R$^{11}$. In one embodiment one of R$^{10}$ and R$^{11}$ represents hydrogen and the other represents C$_{1-6}$alkyl, for example —CH$_3$. R$^{3a}$ may represent —CH$_2$CH$_2$—O—C(=O)—NHCH$_3$.

In one embodiment R$^{3a}$ represents C$_{1-6}$alkyl substituted with —NR$^{12}$—S(=O)$_2$—C$_{1-6}$alkyl. In one embodiment R$^{12}$ represents hydrogen. R$^{3a}$ may represent —CH$_2$CH$_2$NH—S(=O)$_2$—CH$_3$, —CH$_2$CH$_2$CH$_2$NH—S(=O)$_2$—CH$_3$, —CH$_2$CH$_2$NH—S(=O)$_2$—CH(CH$_3$)$_2$ or —CH$_2$CH$_2$NH—S(=O)$_2$—CH$_2$CH$_3$.

In one embodiment R$^{3a}$ represents C$_{1-6}$alkyl substituted with —NR$^{12}$—S(=O)$_2$—NR$^{14}$R$^{15}$. In one embodiment R$^{12}$ represents hydrogen and R$^{14}$ and R$^{15}$ each represent —CH$_3$. R$^{3a}$ may represent —CH$_2$CH$_2$NH—S(=O)$_2$—N(CH$_3$)$_2$ or —CH$_2$CH$_2$CH$_2$NH—S(=O)$_2$—N(CH$_3$)$_2$.

In one embodiment R$^{3a}$ represents C$_{1-6}$alkyl substituted with hydroxyl and R$^9$. In one embodiment when R$^{3a}$ represents C$_{1-6}$alkyl substituted with hydroxyl and R$^9$, R$^9$ represents a saturated 5 membered monocyclic heterocyclyl containing one nitrogen heteroatom, for example pyrrolidinyl. R$^{3a}$ may represent propyl substituted with —OH and 1-pyrrolidinyl. The heterocyclyl may be substituted. For example the heterocyclyl is substituted with
a) two halogens, for example two fluorines. R$^{3a}$ may represent propyl substituted with —OH and 1-pyrrolidinyl where the 1-pyrrolidinyl is substituted in the 3 position with two fluorines; or
b) a cyano group. R$^{3a}$ may represent propyl substituted with —OH and 1-pyrrolidinyl where the 1-pyrrolidinyl is substituted in the 3 position with a cyano group.

In one embodiment when R$^{3a}$ represents C$_{1-6}$alkyl substituted with hydroxyl and R$^9$, R$^9$ represents a saturated 6 membered monocyclic heterocycle containing one nitrogen and one oxygen heteroatom, for example morpholinyl. R$^{3a}$ may represent propyl substituted with —OH and 4-morpholinyl.

In one embodiment when R$^{3a}$ represents C$_{1-6}$alkyl substituted with hydroxyl and R$^9$, R$^9$ represents a saturated 6 membered monocyclic heterocycle containing one nitrogen heteroatom, for example piperidinyl. R$^{3a}$ may represent propyl substituted with —OH and 1-piperidinyl.

In one embodiment when R$^{3a}$ represents C$_{1-6}$alkyl substituted with hydroxyl and R$^9$, R$^9$ represents an optionally substituted bicyclic heterocyclyl containing one nitrogen heteroatom, said bicyclic heterocyclyl may be substituted for example with two =O groups. R$^{3a}$ may represent propyl substituted with hydroxyl and isoindole-1,3-dione.

In one embodiment R$^{3a}$ represents —C$_{1-6}$alkyl-C(R$^{12}$)=N—O—R$^{12}$. R$^{12}$ may independently be chosen from hydrogen and C$_{1-4}$alkyl optionally substituted with C$_{1-4}$alkoxy, for example —CH$_3$ or —CH(CH$_3$)$_2$ or CH$_2$OCH$_3$. R$^{3a}$ may represent —CH$_2$C(CH$_3$)=N—O—H, —CH$_2$C(CH$_2$OCH$_3$)=N—O—H or —CH$_2$C(CH(CH$_3$)$_2$)=N—O—H.

In one embodiment R$^{3a}$ represents C$_{1-6}$alkyl substituted with —C(=O)—R$^9$. R$^9$ may represent a saturated 5-membered monocyclic heterocycle containing one nitrogen heteroatom, for example pyrrolidinyl. R$^{3a}$ may represent —CH$_2$—C(=O)—R$^9$ and R$^9$ is 1-pyrrolidinyl.

In one embodiment R$^{3a}$ represents C$_{2-6}$alkynyl substituted with R$^9$. R$^9$ may represent an aromatic 5-membered monocyclic heterocycle containing two nitrogen heteroatoms, for example imidazolyl. The heterocyclyl may be substituted, for example substituted with one C$_{1-4}$alkyl, for example —CH$_3$.

$R^{3a}$ may represent —CH$_2$—C≡C-(2-imidazolyl) wherein the 2-imidazolyl is substituted in the 1 position with —CH$_3$ or —CH$_2$—C≡C-(5-imidazolyl) wherein the 5-imidazolyl is substituted in the 1 position with —CH$_3$.

In one embodiment $R^9$ is a monocyclic heterocyclyl containing at least one heteroatom selected from N, O or S, said monocyclic heterocyclyl optionally being substituted with 1 substituent selected from =O or C$_{1-4}$alkyl.

In one embodiment $R^{3a}$ represents C$_{1-6}$alkyloxyC$_{1-6}$alkyl wherein each C$_{1-6}$alkyl may optionally be substituted with one or two hydroxyl groups. $R^{3a}$ may represent —CH$_2$CHOHCH$_2$OCH$_3$.

In one embodiment $R^{3a}$ represents C$_{2-6}$alkenyl. $R^{3a}$ may represent —CH$_2$—CH=CH$_2$.

In one embodiment $R^{3a}$ represents C$_{2-6}$alkynyl. $R^{3a}$ may represent —CH$_2$—C≡C—H In one embodiment $R^{3a}$ represents $R^{13}$.

In one embodiment when $R^{3a}$ represents $R^{13}$, $R^{13}$ represents a saturated 4 membered monocyclic heterocycle containing one oxygen heteroatom. $R^{3a}$ may represent 3-oxetanyl. In another embodiment when $R^{3a}$ represents $R^{13}$, $R^{13}$ represents an optionally substituted C$_{3-8}$cycloalkyl. For example the C$_{3-8}$cycloalkyl may be substituted with one NR$^{14}$R$^{15}$ where one of R$^{14}$ and R$^{15}$ represents hydrogen and the other represents C$_{1-4}$alkyl optionally substituted with hydroxyl, for example —CH(CH$_3$)$_2$. $R^{3a}$ may represent cyclohexanyl substituted in the 4 position with —NH—CH(CH$_3$)$_2$.

In one embodiment $R^{14}$ and $R^{15}$ each independently represent hydrogen or C$_{1-4}$alkyl.

In one embodiment $R^{3a}$ represents C$_{1-6}$alkyl substituted with $R^9$, wherein $R^9$ is a saturated heterocyclyl substituted with $R^{13}$, wherein $R^{13}$ is a saturated heterocyclyl which is optionally substituted, for example substituted with —C(=O)—C$_{1-6}$alkyl. In one embodiment $R^9$ is piperazinyl substituted with $R^{13}$, wherein $R^{13}$ is piperidinyl substituted with —C(=O)—C$_{1-6}$alkyl.

In one embodiment $R^{3b}$ represents hydrogen.

In one embodiment $R^{3b}$ represents hydroxyl.

In one embodiment $R^{3a}$ represents hydroxyl and $R^{3b}$ represents hydrogen.

In one embodiment $R^{3a}$ and $R^{3b}$ are taken together to form =O, to form =NR$^{10}$, to form cyclopropyl together with the carbon atom to which they are attached, to form =CH—C$_{0-4}$alkyl substituted with $R^{3c}$, or to form

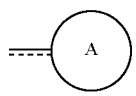

wherein ring A is a monocyclic 5 to 7 membered saturated heterocycle containing one heteroatom selected from N, O or S, said heteroatom not being positioned in alpha position of the double bond, wherein ring A is optionally being substituted with cyano, C$_{1-4}$alkyl, hydroxyC$_{1-4}$alkyl, H$_2$N—C$_{1-4}$alkyl, (C$_{1-4}$alkyl)NH—C$_{1-4}$alkyl, (C$_{1-4}$alkyl)$_2$N—C$_{1-4}$alkyl, (haloC$_{1-4}$alkyl)NH—C$_{1-4}$alkyl, C$_{1-4}$alkoxyC$_{1-4}$alkyl, —C(=O)—NH$_2$, —C(=O)—NH(C$_{1-4}$alkyl), —C(=O)—N(C$_{1-4}$alkyl)$_2$.

In one embodiment $R^{3a}$ and $R^{3b}$ are taken together to form =O, to form cyclopropyl together with the carbon atom to which they are attached, to form =CH—C$_{0-4}$alkyl substituted with $R^{3c}$, or to form

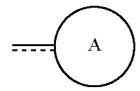

wherein ring A is a monocyclic 5 to 7 membered saturated heterocycle containing one heteroatom selected from N, O or S, said heteroatom not being positioned in alpha position of the double bond.

In one embodiment $R^{3a}$ and $R^{3b}$ are taken together to form =O.

In one embodiment $R^{3a}$ and $R^{3b}$ are taken together to form cyclopropyl together with the carbon atom to which they are attached.

In one embodiment $R^{3a}$ and $R^{3b}$ are taken together to form =CH—C$_{0-4}$alkyl substituted with $R^{3c}$. $R^{3c}$ has the following meaning:
a) $R^{3c}$ may represent cyano. $R^{3a}$ and $R^{3b}$ may be taken together to form =CH—CN;
b) $R^{3c}$ may represent —C(=O)—C$_{1-6}$alkyl. $R^{3a}$ and $R^{3b}$ may be taken together to form =CH—C(=O)—CH$_3$;
c) $R^{3c}$ may represent hydroxyl. $R^{3a}$ and $R^{3b}$ may be taken together to form =CHCH$_2$OH.

In one embodiment $R^{3c}$ represents hydroxyl, C$_{1-6}$alkoxy, $R^9$, —NR$^{10}$R$^{11}$, cyano, —C(=O)—C$_{1-6}$alkyl or —CH(OH)—C$_{1-6}$alkyl.

In one embodiment $R^{3c}$ represents hydroxyl, —NR$^{10}$R$^{11}$, cyano, or —C(=O)—C$_{1-6}$alkyl.

In one embodiment $R^{3a}$ and $R^{3b}$ are taken together to form =CH—C$_{0-4}$alkyl in the Z configuration.

In one embodiment $R^{3c}$ represents —NR$^{10}$R$^{11}$. In one embodiment $R^{10}$ and $R^{11}$ each independently represent C$_{1-6}$alkyl, for example —CH$_3$. $R^{3a}$ and $R^{3b}$ may be taken together to form =CHCH$_2$N(CH$_3$)$_2$.

In one embodiment one of R$^{10}$ and R$^{11}$ represents hydrogen and the other represents C$_{1-6}$alkyl, for example —CH(CH$_3$)$_2$, $R^{3a}$ and $R^{3b}$ may be taken together to form =CHCH$_2$NHCH(CH$_3$)$_2$.

In one embodiment one of R$^{10}$ and R$^{11}$ represents hydrogen and the other represents haloC$_{1-6}$alkyl, for example —CH$_2$CF$_3$. $R^{3a}$ and $R^{3b}$ may be taken together to form =CHCH$_2$NHCH$_2$CF$_3$.

In one embodiment $R^{10}$ and $R^{11}$ each independently represent hydrogen, C$_{1-6}$alkyl, C$_{1-6}$alkyl substituted with —NR$^{14}$R$^{15}$ or haloC$_{1-6}$alkyl.

In one embodiment $R^{14}$ and $R^{15}$ each independently represent hydrogen or C$_{1-4}$alkyl.

In one embodiment $R^{3a}$ and $R^{3b}$ are taken together to form

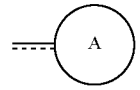

wherein ring A is a monocyclic 5 to 7 membered saturated heterocycle containing one heteroatom selected from N, O or S, said heteroatom not being positioned in alpha position of the double bond. The ring A may represent a monocyclic 6 membered saturated heterocycle containing one nitrogen heteroatom, for example piperidin-3-yl.

In one embodiment $R^{3c}$ represents hydrogen.

In a further embodiment the compound of formula (I) as defined herein is selected from the following compounds or is one of the following compounds:

{(Z)-3-(3,5-Dimethoxy-phenyl)-3-[3-(1-methyl-1H-pyrazol-4-yl)-quinoxalin-6-yl]-allyl}-dimethyl-amine;
{(Z)-3-(3,5-Dimethoxy-phenyl)-3-[3-(1-methyl-1H-pyrazol-4-yl)-quinoxalin-6-yl]-allyl}-isopropyl-amine;
{(Z)-3-(3,5-Dimethoxy-phenyl)-3-[3-(1-methyl-1H-pyrazol-4-yl)-quinoxalin-6-yl]-allyl}-(2,2,2-trifluoro-ethyl)-amine;
{(S)-3-(3,5-Dimethoxy-phenyl)-3-[3-(1-methyl-1H-pyrazol-4-yl)-quinoxalin-6-yl]-propyl}-isopropyl-amine;
{3-(3,5-Dimethoxy-phenyl)-3-[3-(1-methyl-1H-pyrazol-4-yl)-quinoxalin-6-yl]-propyl}-isopropyl-amine;
a N-oxide thereof, a pharmaceutically acceptable salt thereof or a solvate thereof.

In a further embodiment the compound of formula (I) as defined herein is selected from compound 10, 8, 14, 19a and 29 (see Table A1).

According to a further aspect of the invention there is provided compounds of formula (I):

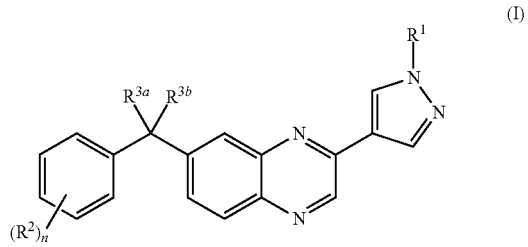

(I)

including any tautomeric or stereochemically isomeric form thereof, wherein
n represents an integer equal to 0, 1, or 2;
$R^1$ represents $C_{1-6}$alkyl;
$R^2$ represents $C_{1-4}$alkoxy;
$R^{3a}$ represents —$NR^{10}R^{11}$, hydroxyl, hydroxy$C_{1-6}$alkyl, $C_{1-6}$alkyl substituted with —C(=O)—$C_{1-6}$alkyl, $C_{1-6}$alkyl substituted with $R^9$, cyano$C_{1-6}$alkyl, $C_{1-6}$alkyl substituted with —$NR^{11}R^{11}$, $C_{1-6}$alkyl substituted with hydroxyl and —$NR^{10}R^{11}$, $C_{1-6}$alkyl substituted with —C(=O)—O—$C_{1-6}$alkyl, $C_{1-6}$alkyl substituted with —C(=O)—$NR^{10}R^{11}$;
$R^{3b}$ represents hydrogen or hydroxyl; or
$R^{3a}$ and $R^{3b}$ are taken together to form =O, to form cyclopropyl together with the carbon atom to which they are attached, to form =CH—$C_{0-4}$alkyl substituted with $R^{3c}$, or to form

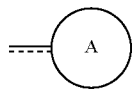

wherein ring A is a monocyclic 5 to 7 membered saturated heterocycle containing one heteroatom selected from N, O or S, said heteroatom not being positioned in alpha position of the double bond, wherein ring A is optionally being substituted with cyano, $C_{1-4}$alkyl, hydroxy$C_{1-4}$alkyl, $H_2N$—$C_{1-4}$alkyl, $H(C_{1-4}alkyl)N$—$C_{1-4}$alkyl, $(C_{1-4}alkyl)_2N$—$C_{1-4}$alkyl, $C_{1-4}$alkoxy$C_{1-4}$alkyl, —C(=O)—$NH_2$, —C(=O)—$NH(C_{1-4}alkyl)$, —C(=O)—$N(C_{1-4}alkyl)_2$;
$R^{3c}$ represents hydroxyl, $C_{1-6}$alkoxy, $R^9$, —$NR^{10}R^{11}$, cyano, —C(=O)—$C_{1-6}$alkyl;
$R^6$ represents $C_{3-8}$cycloalkyl, $C_{3-8}$cycloalkenyl, phenyl, 4, 5, 6 or 7-membered monocyclic heterocyclyl containing at least one heteroatom selected from N, O or S; said $C_{3-8}$cycloalkyl, $C_{3-8}$cycloalkenyl, phenyl, 4, 5, 6 or 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^9$ represents $C_{3-8}$cycloalkyl, $C_{3-8}$cycloalkenyl, phenyl or a 3 to 12 membered monocyclic or bicyclic heterocyclyl containing at least one heteroatom selected from N, O or S, said $C_{3-8}$cycloalkyl, $C_{3-8}$cycloalkenyl, aryl or a 3 to 12 membered monocyclic or bicyclic heterocyclyl each optionally and each independently being substituted with 1 to 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-6}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O or S wherein said heterocyclyl is optionally substituted with $R^{16}$;
or when two of the substituents of $R^9$ are attached to the same atom, they may be taken together to form a 4, 5, 6 or 7-membered saturated monocyclic heterocyclyl containing at least one heteroatom selected from N, O or S;
$R^{10}$ and $R^{11}$ each independently represent hydrogen, $C_{1-6}$alkyl, cyano$C_{1-6}$alkyl, $C_{1-6}$alkyl substituted with —$NR^{14}R^{15}$, halo$C_{1-6}$alkyl, hydroxy$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —C(=O)—$R^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, —(C=O)—$C_{1-6}$alkyl, $C_{1-6}$alkoxy, or —$NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

$R^{16}$ represents hydroxyl, halogen, cyano, $C_{1-4}$alkyl, $C_{1-4}$alkoxy, —$NR^{14}R^{15}$ or —C(=O)$NR^{14}R^{15}$;

a N-oxide thereof, a pharmaceutically acceptable salt thereof or a solvate thereof.

According to a still further aspect of the invention there is provided compounds of formula (I):

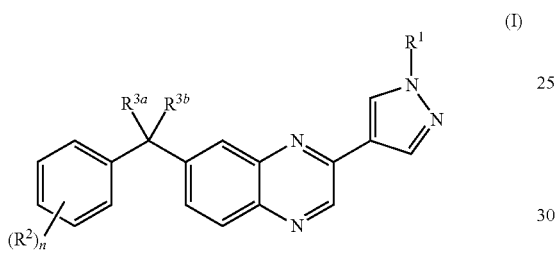

(I)

including any tautomeric or stereochemically isomeric form thereof, wherein n represents an integer equal to 0 or 2;

$R^1$ represents methyl;

$R^2$ represents $C_{1-4}$alkoxy, for example $CH_3O$—;

$R^{3a}$ represents
- —$NR^{10}R^{11}$, for example —$NHCH_2CH_2NHCH(CH_3)_2$,
- hydroxyl,
- hydroxy$C_{1-6}$alkyl, for example —$CH_2CH_2OH$,
- $C_{1-6}$alkyl substituted with —C(=O)—$C_{1-6}$alkyl, for example $CH_3$—C(=O)—$CH_2$—,
- $C_{1-6}$alkyl substituted with $R^9$, for example methyl substituted with ethylene oxide through the 2 position of the ethylene oxide, wherein the ethylene oxide is substituted in the 2 position with —$CH_3$,
  - ethyl substituted with 1-pyrrolidinyl which is substituted in the 2 position with =O,
  - cyano$C_{1-6}$alkyl, for example —$CH_2CN$ or —$CH_2CH_2CN$,
- $C_{1-6}$alkyl substituted with —$NR^{10}R^{11}$, for example —$CH_2CH_2NH_2$, —$CH_2CH_2CH_2NH_2$, —$CH_2NHCH_3$, —$CH_2CH_2NHCH(CH_3)_2$—$CH_2CH_2N(CH_3)_2$, —$CH_2CH_2NHCH_2CF_3$, or —$CH_2NHCH_2CH_2NHCH(CH_3)_2$,
- $C_{1-6}$alkyl substituted with hydroxyl and —$NR^{10}R^{11}$, for example —$CH_2C(CH_3)(OH)CH_2NHCH(CH_3)_2$,
- $C_{1-6}$alkyl substituted with —C(=O)—O—$C_{1-6}$alkyl, for example —$CH_2C(=O)$—O—$CH_3$, or —$CH_2$—C(=O)—O—$CH_2CH_3$,
- $C_{1-6}$alkyl substituted with —C(=O)—$NR^{10}R^{11}$, for example —$CH_2C(=O)NHCH(CH_3)_2$;

$R^{3b}$ represents hydrogen or hydroxyl;

$R^{3a}$ and $R^{3b}$ are taken together to form:
- =O;
- cyclopropyl together with the carbon atom to which they are attached;
- =CH—$C_{0-4}$alkyl substituted with $R^{3c}$, for example =CH—CN, =CH—C(=O)—$CH_3$, =CH—$CH_2OH$, =CH—$CH_2N(CH_3)_2$, =CH—$CH_2NCH(CH_3)_2$, or =CH—$CH_2NHCH_2CF_3$; or

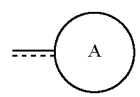

wherein ring A represents piperidin-3-yl;

a N-oxide thereof, a pharmaceutically acceptable salt thereof or a solvate thereof.

In one embodiment the compound of formula (I) is a compound of formula (I-a):

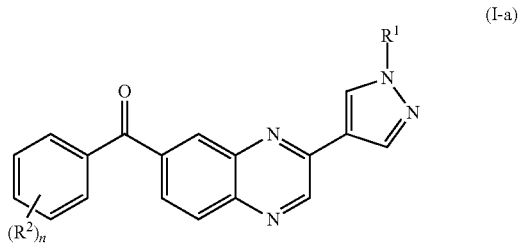

(I-a)

including any tautomeric or stereochemically isomeric form thereof;

and a N-oxide thereof, a pharmaceutically acceptable salt thereof or a solvate thereof, wherein n, $R^1$ and $R^2$ are as defined herein.

In one embodiment the compound of formula (I) is a compound of formula (I'-a):

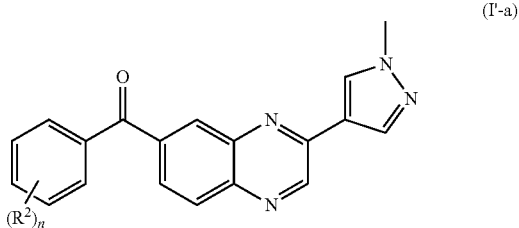

(I'-a)

including any tautomeric or stereochemically isomeric form thereof;

and a N-oxide thereof, a pharmaceutically acceptable salt thereof or a solvate thereof, wherein n and $R^2$ are as defined herein.

In one embodiment the compound of formula (I) is a compound of formula (I"-a)

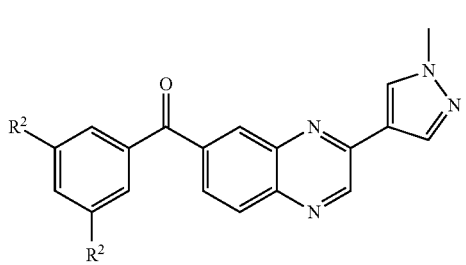
(I'''-a)

including any tautomeric or stereochemically isomeric form thereof;

and a N-oxide thereof, a pharmaceutically acceptable salt thereof or a solvate thereof, wherein $R^2$ is as defined herein.

In one embodiment the compound of formula (I) is the compound of formula (I'''-a)

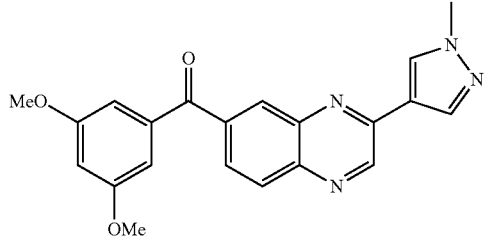
(I'''-a)

including any tautomeric form thereof;

and a N-oxide thereof, a pharmaceutically acceptable salt thereof or a solvate thereof.

In one embodiment the compound of formula (I) is a compound of formula (I-b):

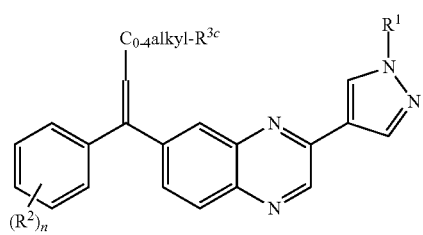
(I-b)

including any tautomeric or stereochemically isomeric form thereof;

and a N-oxide thereof, a pharmaceutically acceptable salt thereof or a solvate thereof, wherein n, $R^1$, $R^2$ and $R^{3c}$ are as defined herein.

In one embodiment the compound of formula (I) is a compound of formula (I'-b):

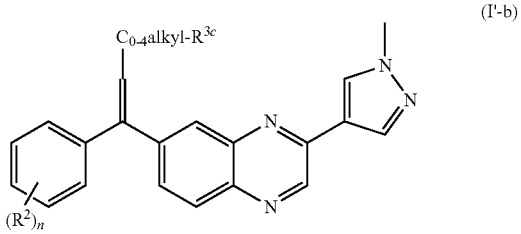
(I'-b)

including any tautomeric or stereochemically isomeric form thereof;

and a N-oxide thereof, a pharmaceutically acceptable salt thereof or a solvate thereof, wherein n, $R^2$ and $R^{3c}$ are as defined herein.

In one embodiment the compound of formula (I) is a compound of formula (I''-b)

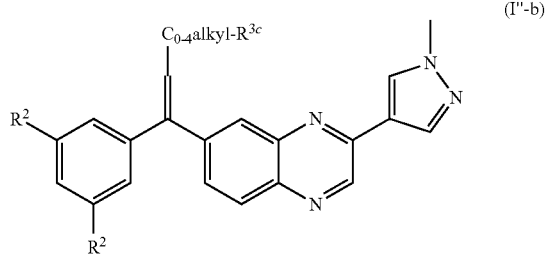
(I''-b)

including any tautomeric or stereochemically isomeric form thereof;

and a N-oxide thereof, a pharmaceutically acceptable salt thereof or a solvate thereof, wherein $R^2$ and $R^{3c}$ are as defined herein.

In one embodiment the compound of formula (I) is a compound of formula (I'''-b)

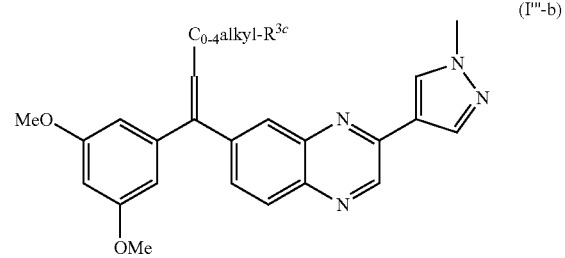
(I'''-b)

including any tautomeric or stereochemically isomeric form thereof;

and a N-oxide thereof, a pharmaceutically acceptable salt thereof or a solvate thereof, wherein $R^{3c}$ is as defined herein.

The compound of formula (I'-b), (I''-b) or (I'''-b) may be in the E or Z configuration, preferably in the Z configuration.

A preferred subgroup of the compounds of formula (I-b), (I'-b), (I''-b) or (I'''-b) are those compounds having the following geometry at the double bond as shown in (I'-b'), (I''-b') and (I'''-b') below:

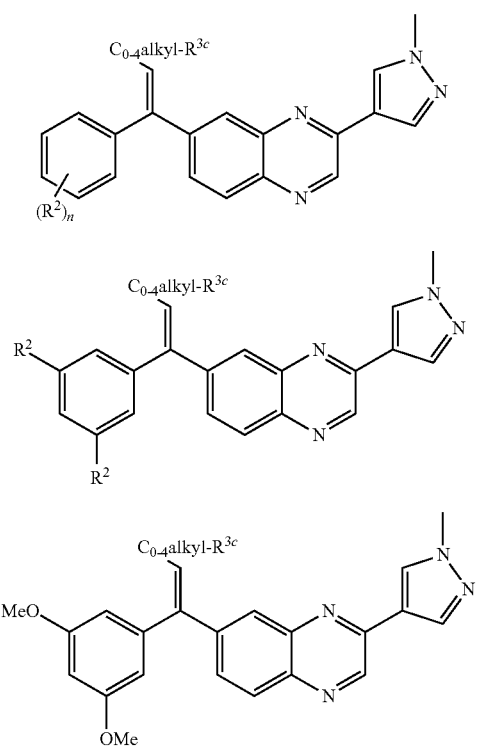

In one embodiment the compound of formula (I) is a compound of formula (I-c):

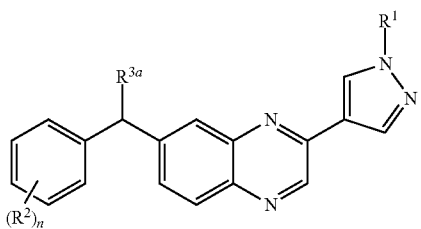

including any tautomeric or stereochemically isomeric form thereof;
and a N-oxide thereof, a pharmaceutically acceptable salt thereof or a solvate thereof, wherein n, $R^1$, $R^2$ and $R^{3a}$ are as defined herein.

In one embodiment the compound of formula (I) is a compound of formula (I'-c):

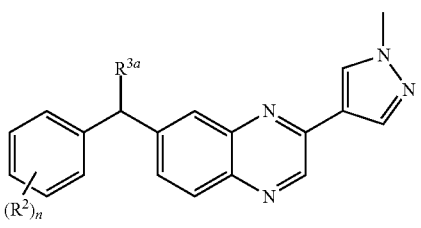

including any tautomeric or stereochemically isomeric form thereof;

and a N-oxide thereof, a pharmaceutically acceptable salt thereof or a solvate thereof, wherein n, $R^2$ and $R^{3a}$ are as defined herein.

In one embodiment the compound of formula (I) is a compound of formula (I"-c)

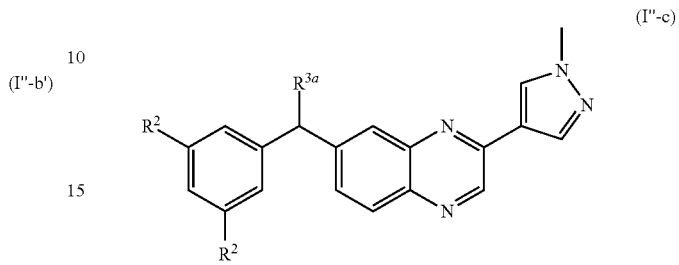

including any tautomeric or stereochemically isomeric form thereof;

and a N-oxide thereof, a pharmaceutically acceptable salt thereof or a solvate thereof, wherein $R^2$ and $R^{3a}$ are as defined herein.

In one embodiment the compound of formula (I) is a compound of formula (I'''-c)

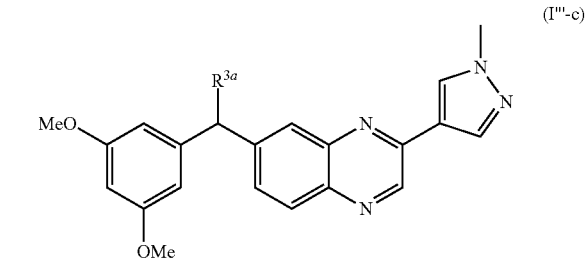

including any stereochemically isomeric form thereof;

and a N-oxide thereof, a pharmaceutically acceptable salt thereof or a solvate thereof, wherein $R^{3a}$ is as defined herein.

In one embodiment the compound of formula (I) is a compound of formula (I-d):

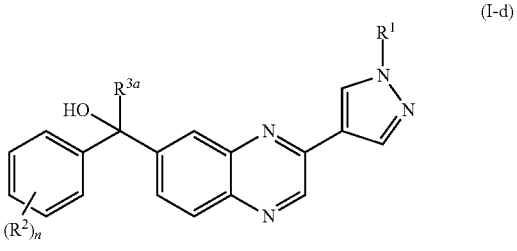

including any tautomeric or stereochemically isomeric form thereof;

and a N-oxide thereof, a pharmaceutically acceptable salt thereof or a solvate thereof, wherein n, $R^1$, $R^2$ and $R^{3a}$ are as defined herein.

In one embodiment the compound of formula (I) is a compound of formula (I'-d):

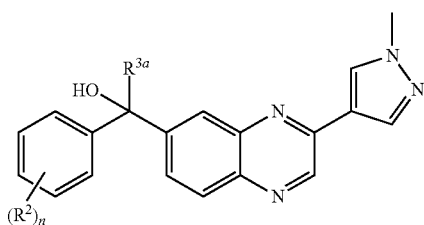

(I'-d)

including any tautomeric or stereochemically isomeric form thereof;
and a N-oxide thereof, a pharmaceutically acceptable salt thereof or a solvate thereof, wherein n, $R^2$ and $R^{3a}$ are as defined herein.

In one embodiment the compound of formula (I) is a compound of formula (I"-d)

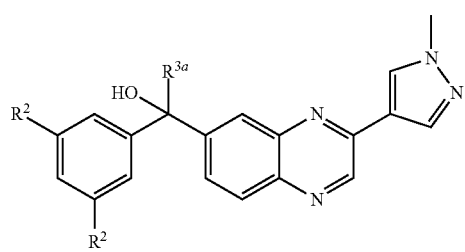

(I"-d)

including any tautomeric or stereochemically isomeric form thereof;
and a N-oxide thereof, a pharmaceutically acceptable salt thereof or a solvate thereof, wherein $R^2$ and $R^{3a}$ are as defined herein.

In one embodiment the compound of formula (I) is a compound of formula (I'''-d)

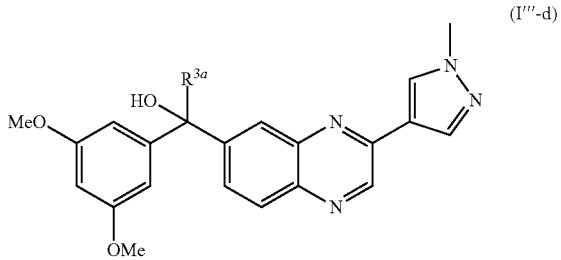

(I'''-d)

including any tautomeric or stereochemically isomeric form thereof;
and a N-oxide thereof, a pharmaceutically acceptable salt thereof or a solvate thereof, wherein $R^{3a}$ is as defined herein.

For the avoidance of doubt, it is to be understood that each general and specific preference, embodiment and example for one substituent may be combined with each general and specific preference, embodiment and example for one or more, preferably, all other substituents as defined herein and that all such embodiments are embraced by this application.

Methods for the Preparation of Compounds of Formula (I)

In this section, as in all other sections of this application unless the context indicates otherwise, references to formula (I) also include all other sub-groups and examples thereof as defined herein.

In general, compounds of formula (I) can be prepared according to the following reaction Scheme 1.

Scheme 1

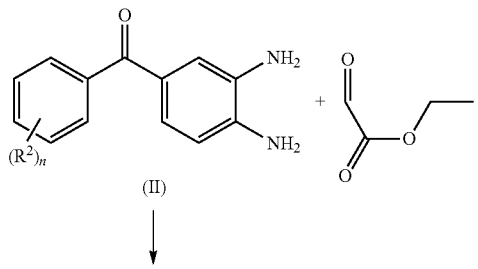

(II)

↓

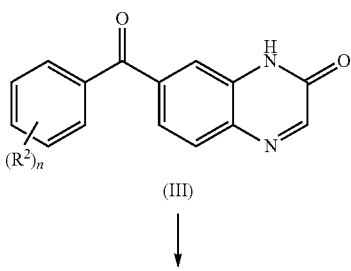

(III)

↓

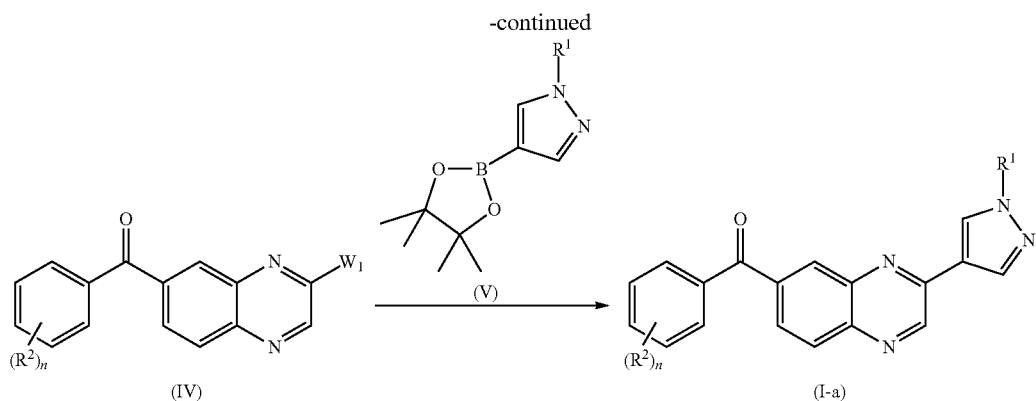

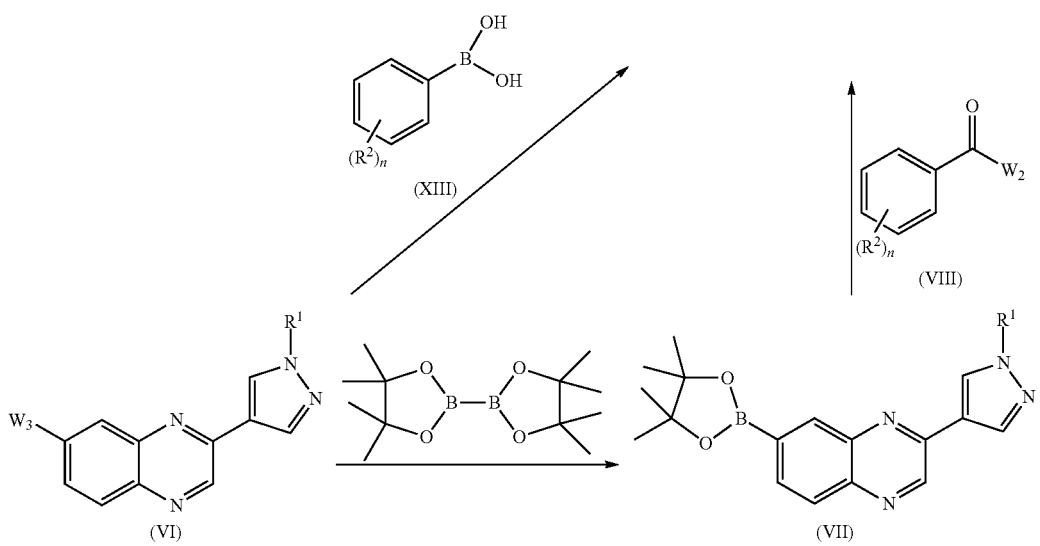

In scheme 1, an intermediate of formula (II) is reacted with an ethylglyoxalate solution, in the presence of a suitable solvent, such as for example an alcohol, e.g. ethanol and the like, resulting in an intermediate of formula (III). The intermediate of formula (III) is further reacted with a leaving group introducing agent, such as for example phosphorus oxychloride, resulting in an intermediate of formula (IV), which is further reacted with an intermediate of formula (V) in the presence of a suitable catalyst, such as for example tetrakis(triphenylphosphine)palladium (0), a suitable base, such as for example $Na_2CO_3$, and a suitable solvent or solvent mixture, such as for example ethylene glycol dimethylether and water, to give a compound of formula (I-a). Compounds of formula (I-a) can also be prepared by reacting an intermediate of formula (VI) wherein $W_3$ represents a suitable group, such as for example halo, e.g. bromo and the like, with bis (pinacolato)diboron in the presence of a suitable catalyst, such as for example $PdCl_2$, and a suitable ligand, such as for example 1,1-bis(diphenylphosphino)ferrocene, in the presence of a salt, such as for example potassium acetate, and a suitable solvent, such as for example dioxane, followed by reacting the resulting intermediate of formula (VII) with an intermediate of formula (VIII) wherein $W_2$ represents a suitable leaving group, such as for example halo, e.g. chloro and the like, in the presence of a catalyst, such as for example dichlorobis(triphenylphosphine)palladium, a suitable base, such as for example $Na_2CO_3$, and a suitable solvent, such as for example tetrahydrofuran. A compound of formula (I-a) can also be prepared by reacting an intermediate of formula (VI) with an intermediate of formula (XIII) in the presence of CO as a reactant, a suitable catalyst, such as for example palladium(II)acetate, a suitable ligand, such as for example tricyclohexylphosphine, a suitable base, such as for example triethylamine, and a suitable solvent, such as for example toluene.

Scheme 2

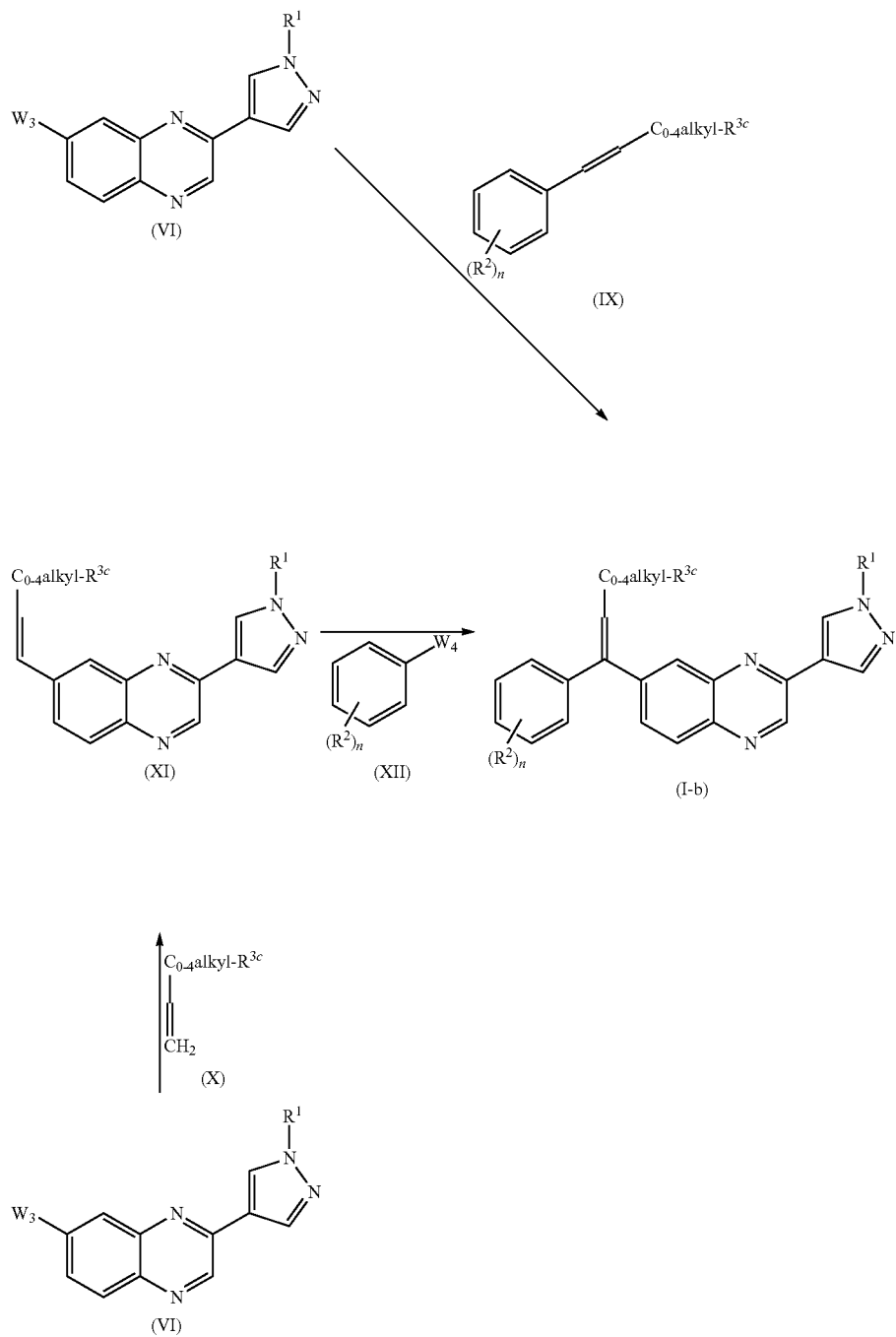

In Scheme 2, intermediates of formula (VI) are reacted with an intermediate of formula (IX) in the presence of a suitable catalyst, such as for example palladium(II)acetate, a suitable base, such as for example potassium acetate, and tetrabutylammonium bromide as solid base, and a suitable solvent, such as for example N,N-dimethylformamide, to give a compound of formula (I-b). Compounds of formula (I-b) can also be prepared by reacting an intermediate of formula (VI) with an intermediate of formula (X) in the presence of a suitable catalyst, such as for example palladium (II)acetate, a suitable ligand, such as for example tri-o-tolylphosphine, a suitable base, such as for example triethylamine, and a suitable solvent, such as for example acetonitrile, resulting in an intermediate of formula (XI), which can then be reacted with an intermediate of formula (XII) wherein $W_4$ represents a suitable leaving group, such as for example halo, e.g. bromo, in the presence of a suitable catalyst, such as for example palladium(II)acetate, a suitable base, such as for example potassium acetate, and tetrabutylammonium bromide as solid base, and a suitable solvent, such as for example N,N-dimethylformamide.

Scheme 3
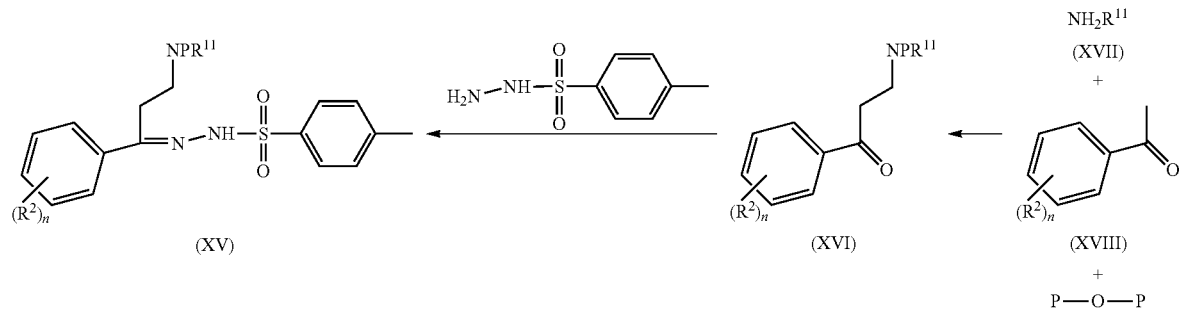
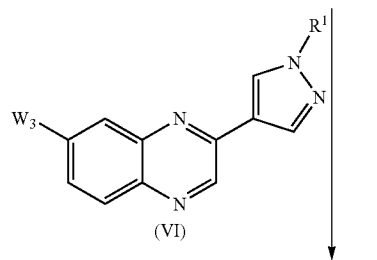
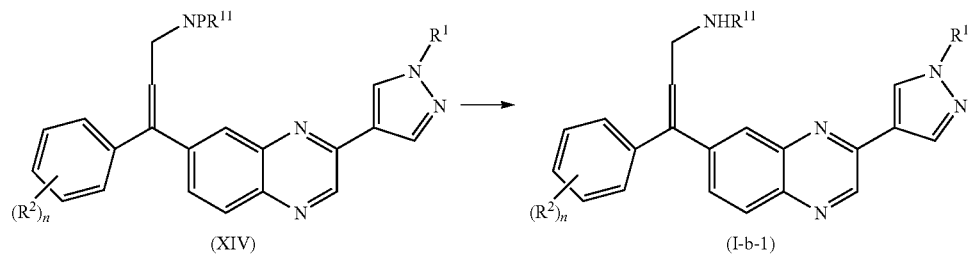
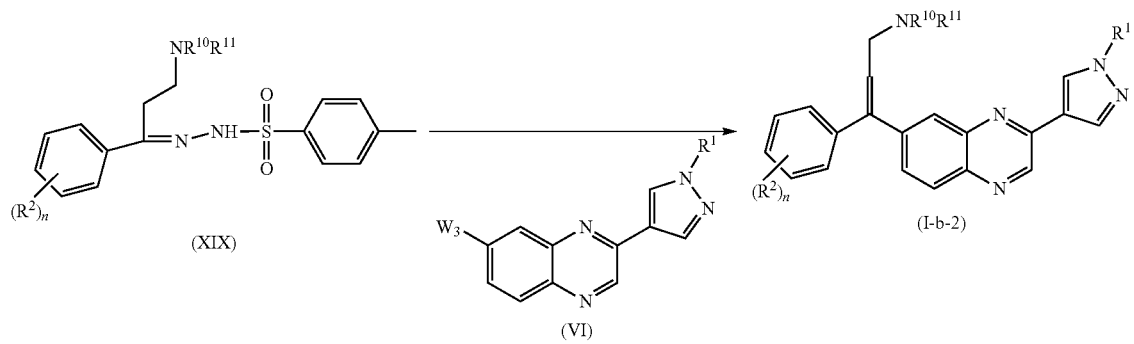

-continued

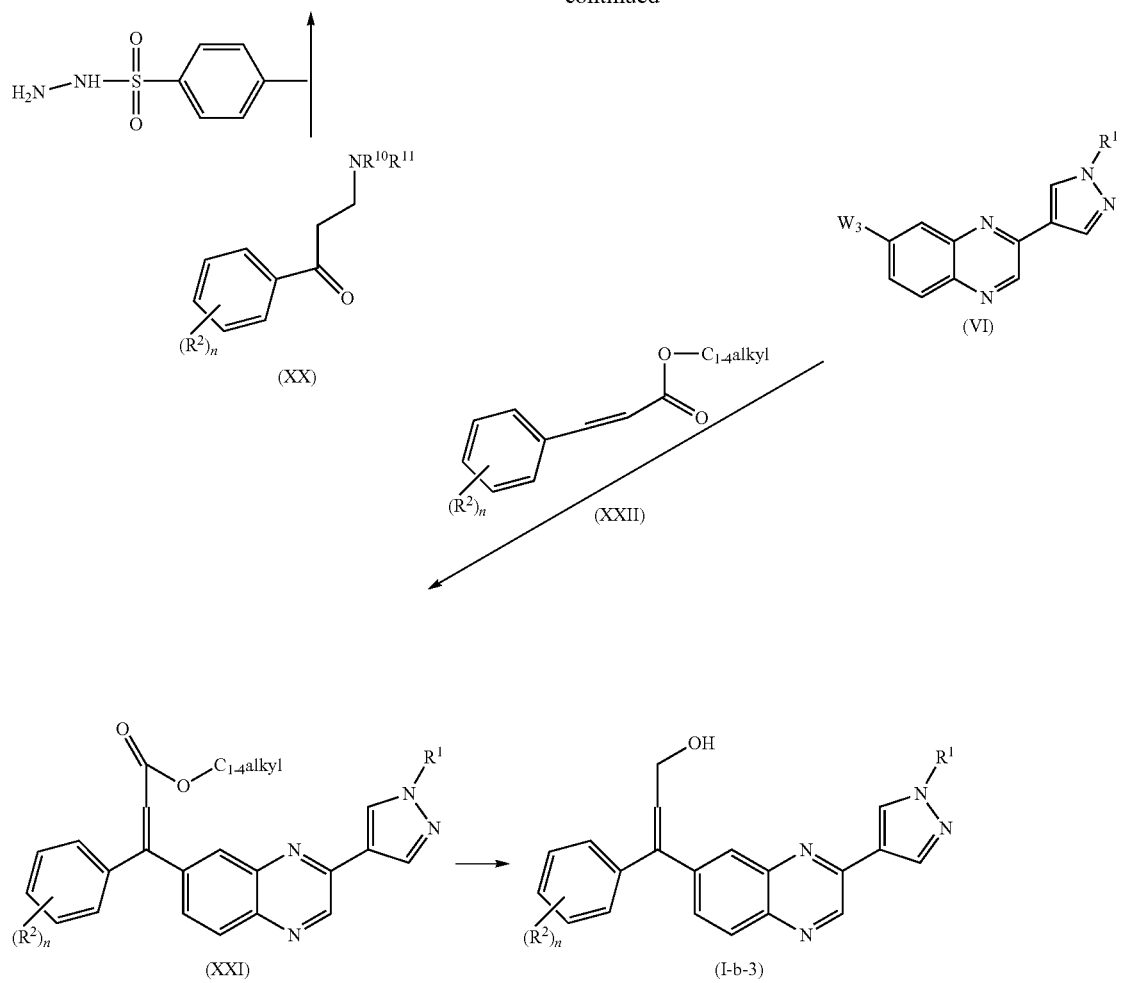

In Scheme 3, an intermediate of formula (XVII) preferably in its salt form, e.g. HCl salt form, and (XVIII) is reacted with paraformaldehyde in the presence of a suitable solvent, such as for example an alcohol, e.g. ethanol, then a suitable agent P—O—P to introduce a suitable protective group P, such as for example —C(=O)—C(CH$_3$)$_3$ wherein P—O—P is (CH$_3$)$_3$—O—C(=O)—O—C(=O)—O—C(CH$_3$)$_3$), is added in the presence of a suitable base, such as for example triethylamine, and a suitable solvent, such as for example dichloromethane, resulting in an intermediate of formula (XVI), which is further reacted with p-toluenesulfonhydrazide in the presence of a suitable solvent, such as for example an alcohol, e.g. ethanol, to give an intermediate of formula (XV). The intermediate of formula (XV) is then further reacted with an intermediate of formula (VI) in the presence of a suitable catalyst, such as for example tris(dibenzylideneacetone)dipalladium (0), a suitable ligand, such as for example 2-dicyclohexylphosphino-2',4',6'-tri-isopropyl-1,1'-biphenyl a suitable base, such as for example lithium tert-butoxide, and a suitable solvent, such as for example dioxane, resulting in an intermediate of formula (XIV), the E and Z isomers of which can be separated by appropriate separation techniques such as column chromatography. The intermediate of formula (XIV) can then be converted into a compound of formula (I-b-1) by deprotection in the presence of a suitable acid, such as for example HCl, and a suitable solvent, such as for example an alcohol, e.g. methanol. A compound of formula (I-b-2) is prepared by reacting an intermediate of formula (XX) with p-toluenesulfonhydrazide in the presence of a suitable acid, such as for example hydrochloric acid, and a suitable solvent, such as for example diethylether and water, resulting in an intermediate of formula (XIX), the E and Z isomers of which can be separated by appropriate separation techniques such as column chromatography. The intermediate of formula (XIX) can then be reacted with an intermediate of formula (VI) in the presence of a suitable catalyst, such as for example tris(dibenzylideneacetone)dipalladium (0), a suitable ligand, such as for example 2-dicyclohexylphosphino-2',4',6'-tri-isopropyl-1,1'-biphenyl a suitable base, such as for example lithium tert-butoxide, and a suitable solvent, such as for example dioxane, resulting in a compound of formula (I-b-2). A compound of formula (I-b-3) is prepared by reacting an intermediate of formula (XXI) with a suitable reducing agent, such as for example diisobutylaluminium hydride, and a suitable solvent, such as for example tetrahydrofuran. The intermediate of formula (XXI) is prepared by reacting an intermediate of formula (VI) with an intermediate of formula (XXII) in the presence of a suitable catalyst, such as for example palladium (II)acetate, a suitable ligand, such as for example tri-o-tolylphosphine, a suitable base, such as for example triethylamine, and a suitable solvent, such as for example acetonitrile.

Scheme 4

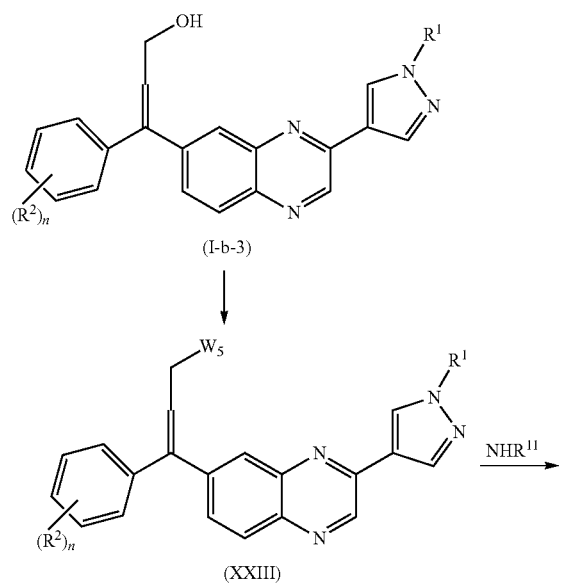

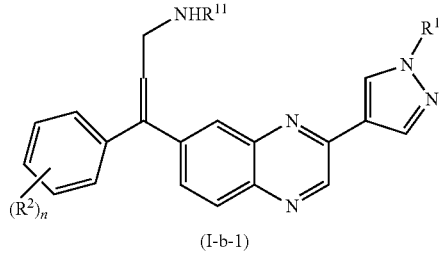

In Scheme 4, a compound of formula (I-b-3) is reacted with a leaving group introducing agent, such as for example methanesulfonyl chloride, in the presence of a suitable base, such as for example triethylamine, and a suitable solvent, such as for example dichloromethane, resulting in an an intermediate of formula (XXIII) wherein $W_5$ represents a suitable leaving group, such as for example halo, e.g. chloro, which is then further reacted with NHR11 in the presence of a suitable solvent, such as for example acetonitrile, to give a compound of formula (I-b-1).

Scheme 5

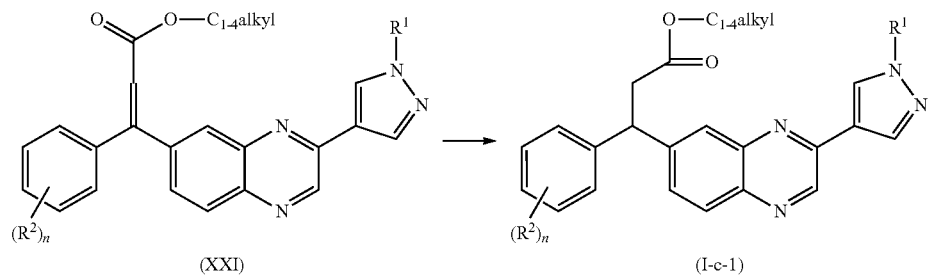

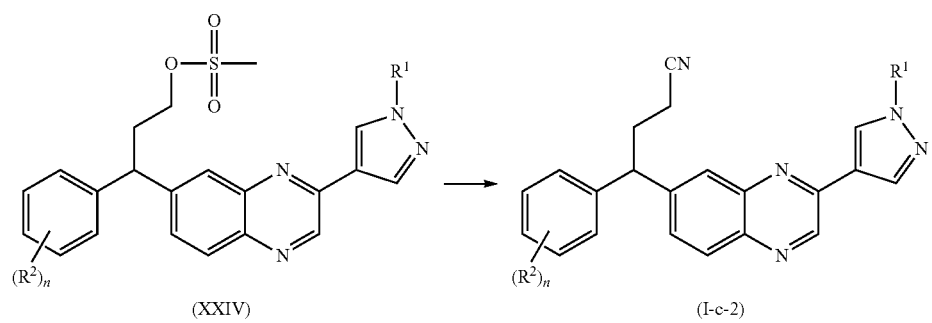

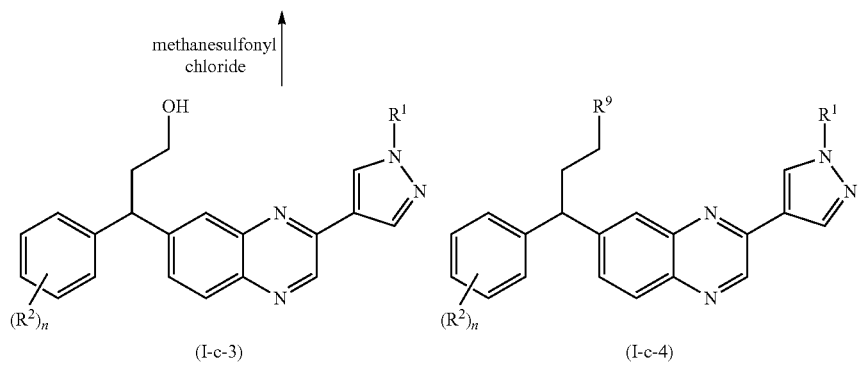

In Scheme 5, a compound of formula (I-c-1) is prepared by reacting an intermediate of formula (XXI) with magnesium in the presence of a suitable solvent, such as for example tetrahydrofuran and an alcohol, e.g. methanol and the like. A compound of formula (I-c-2) is prepared by reacting an intermediate of formula (XXIV) with potassium cyanide in the presence of a suitable solvent, such as for example N,N-dimethylformamide. The intermediate of formula (XXIV) is prepared by reacting a compound of formula (I-c-3) with methanesulfonyl chloride in the presence of a suitable base, such as for sample triethylamine, and a suitable solvent, such as for example acetonitrile. (I-c-3) can be prepared by reduction of (I-b-3) for example using LiAlH$_4$, in an aprotic solvent such as THF. The intermediate of formula (XXIV) is converted into a compound of formula (I-c-4) by reaction with HR$^9$ in the presence of a suitable base, such as for example sodium hydride, and a suitable solvent, such as for example N,N-dimethylformamide.

Scheme 6

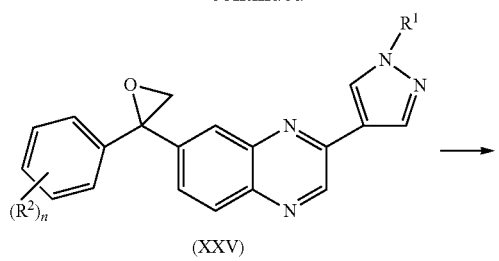

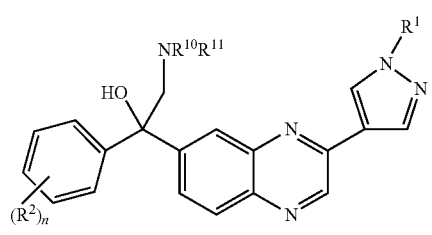

In Scheme 6, a compound of formula (I-a) is reacted with trimethylsulphoxonium iodide in the presence of a suitable base, such as for example potassium tert butoxide, and a suitable solvent, such as for example dimethoxymethane and dimethylsulfoxide resulting in an intermediate of formula (XXV), which can be converted into a compound of formula (I-d-1) by reaction with NHR$^{10}$R$^{11}$ in the presence of a suitable solvent, such as for example an alcohol, e.g. ethanol and the like.

Scheme 7

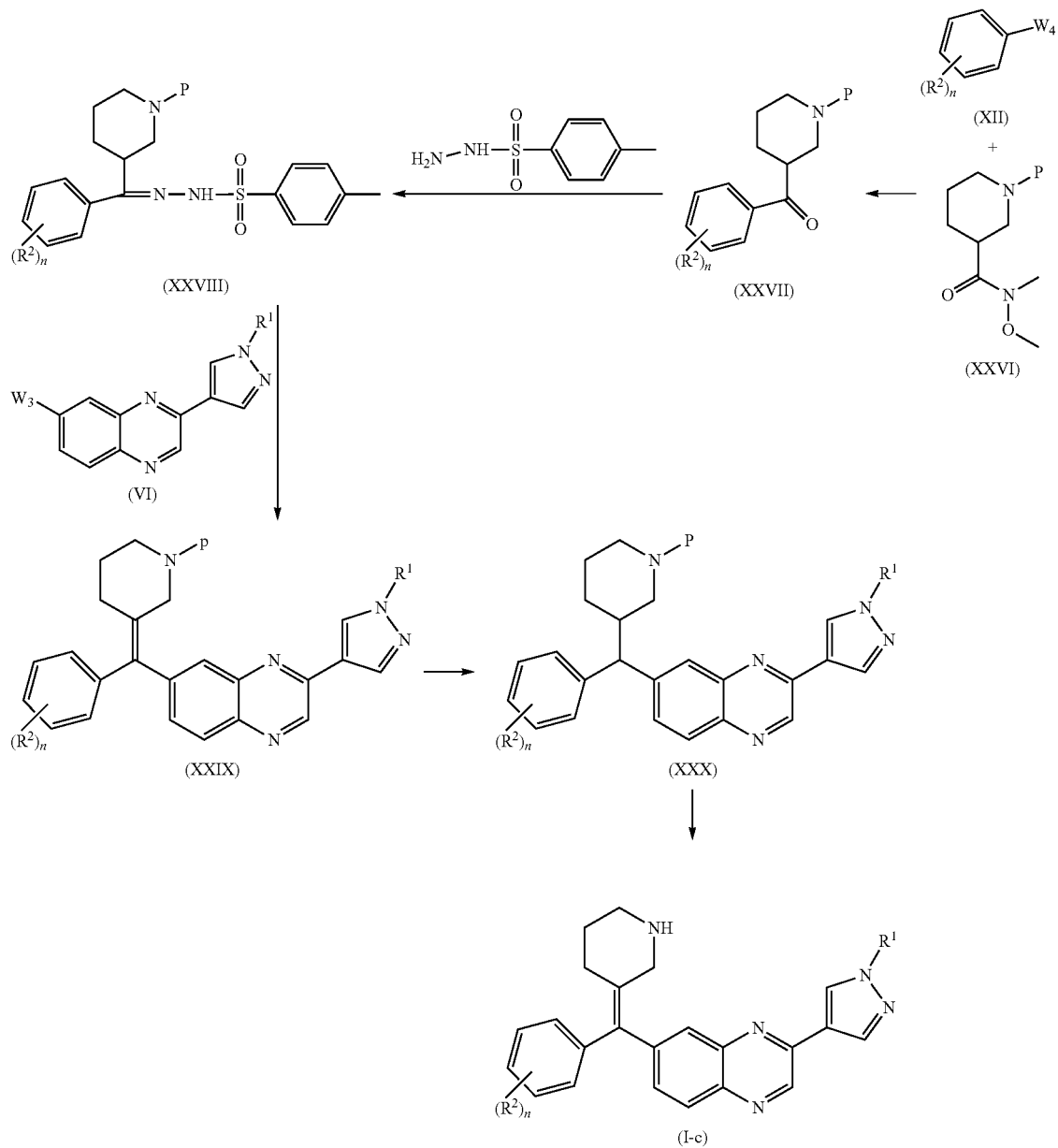

In Scheme 7, an intermediate of formula (XII) as defined above, and (XXVI) wherein P represents a suitable protective group as defined above, is reacted with butyllithium in hexane in the presence of a suitable solvent, such as for example tetrahydrofuran, diethylether or mixtures thereof resulting in an intermediate of formula (XXVII), which is further reacted with p-toluenesulfonhydrazide in the presence of a suitable solvent, such as for example an alcohol, e.g. ethanol, to give an intermediate of formula (XXVIII). The intermediate of formula (XXVIII) is then further reacted with an intermediate of formula (VI) in the presence of a suitable catalyst, such as for example tris(dibenzylideneacetone)dipalladium (0), a suitable ligand, such as for example 2-dicyclohexylphosphino-2',4',6'-tri-isopropyl-1,1'-biphenyl, a suitable base, such as for example lithium tert-butoxide, and a suitable solvent, such as for example dioxane, resulting in an intermediate of formula (XXIX). The intermediate of formula (XXIX) is then converted into an intermediate of formula (XXX) by hydrogenation in the presence of a suitable catalyst, such as for example palladium on charcoal, and a suitable solvent, such as for example an alcohol, e.g. methanol. The intermediate of formula (XXX) can then be converted into a compound of formula (I-e) by reaction with a suitable acid, such as for example hydrochloric acid, in the presence of a suitable solvent, such as for example an alcohol, e.g. methanol.

Compounds of formula (I) can also be prepared according to the above described reactions but starting from the below intermediate of formula (VI') prepared according to Scheme 8.

Scheme 8

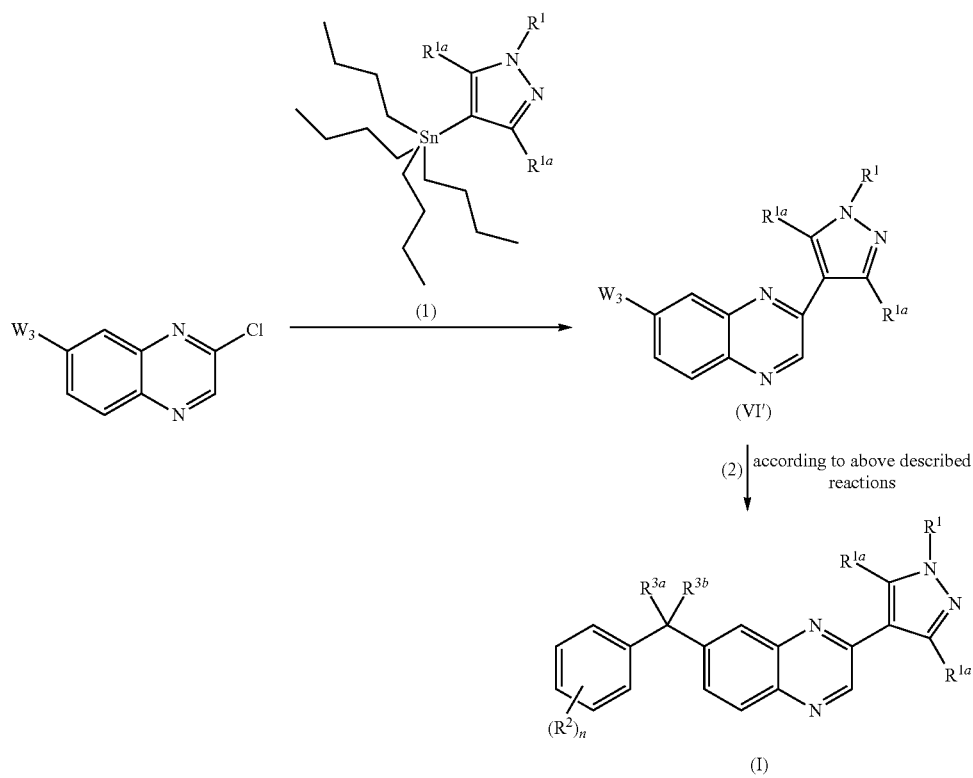

In Scheme 8, step 1 is performed in the presence of a suitable catalyst, such as for example tetrakis(triphenylphisphine)palladium (0), and a suitable solvent, such as for example toluene. For step 2, reactions can be applied as described above starting from an intermediate of formula (VI). It is considered to be within the knowledge of the person skilled in the art to recognize in which condition and for which definition of $R^{1a}$ a protective group is appropriate in step 1 as well as in step 2.

In general, it is considered to be within the knowledge of the person skilled in the art to recognize in which condition and on which part of the molecule a protective group may be appropriate. For instance, protective group on the $R^1$ substituent or on the pyrrazole moiety, or on the $R^2$ substituent or combinations thereof. The skilled person is also considered to be able to recognize the most feasible protective group, such as for example —C(=O)—O—$C_{1-4}$alkyl or

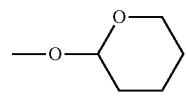

or O—Si(CH$_3$)$_2$(C(CH$_3$)$_3$).

The present invention also comprises deuterated compounds. These deuterated compounds may be prepared by using the appropriate deuterated intermediates during the synthesis process. For instance an intermediate of formula (XII-a)

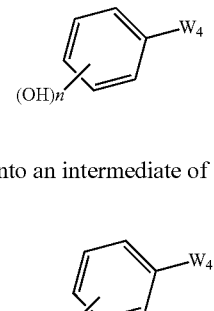

can be converted into an intermediate of formula (XII-b)

by reaction with iodomethane-D3 in the presence of a suitable base, such as for example cesium carbonate, and a suitable solvent, such as for example acetonitrile.

The compounds of formula (I) may also be converted into each other via art-known reactions or functional group transformations. For instance, compounds of formula (I) wherein $R^{3a}$ and $R^{3b}$ are taken together to form =O, can be converted into a compound of formula (I) wherein $R^{3a}$ represents hydroxyl and $R^{3b}$ represents hydrogen, by reaction with a suitable reducing agent, such as for example sodium borohydride and the like, in the presence of a suitable solvent, such as for example tetrahydrofuran or an alcohol, such as for example methanol and the like, or mixtures thereof. Compounds of formula (I) wherein $R^{3a}$ and $R^{3b}$ are taken together to form =O, can be also be converted into a compound of formula (I) wherein $R^{3a}$ represents NR$^{10}$R$^{11}$, by reaction with NHR$^{10}$R$^{11}$ in the presence of a suitable reducing agent, such as for example sodium borohydride, in the presence of a suitable solvent, such as for example an alcohol, e.g. methanol.

Compounds of formula (I) wherein $R^{3a}$ and $R^{3b}$ are taken together to form =CH—$C_{0-4}$alkyl substituted with $R^{3c}$ can be converted into a compound of formula (I) wherein $R^{3a}$ represents —$CH_2$—$C_{0-4}$alkyl substituted with $R^{3c}$ and $R^{3b}$ represents hydrogen by reaction with magnesium in the presence of a suitable solvent, such as for example tetrahydrofuran or an alcohol, such as for example methanol and the like, or mixtures thereof, or by hydrogenation in the presence of a suitable catalyst, such as for example palladium, in the presence of a suitable solvent, such as for example an alcohol, e.g. methanol and the like.

Compounds of formula (I) wherein $R^{3a}$ represents $C_{1-6}$alkyl substituted with hydroxyl, can be converted into a compound of formula (I) wherein $R^{3a}$ represents $C_{1-6}$alkyl substituted with $NR^{10}R^{11}$, by reaction with $NHR^{10}R^{11}$ in the presence of methanesulfonyl chloride, a suitable base, such as for example triethylamine, and a suitable solvent, such as for example acetonitrile.

Compounds of formula (I) wherein $R^{3a}$ represents $C_{1-5}$alkyl substituted with cyano, can be converted into a compound of formula (I) wherein $R^{3a}$ represents $C_{2-6}$alkyl substituted with amino, by reaction with ammonia in the presence of Nickel and a suitable solvent, such as for example tetrahydrofuran.

Compounds of formula (I) wherein $R^{3a}$ represents $C_{1-6}$alkyl substituted with —C(=O)—O—$C_{1-6}$alkyl, can be converted into a compound of formula (I) wherein $R^{3a}$ represents $C_{1-6}$alkyl substituted with hydroxyl, by reaction with lithium aluminiumhydride in the presence of a suitable solvent, such as for example tetrahydrofuran. Compounds of formula (I) wherein $R^{3a}$ represents $C_{1-6}$alkyl substituted with —C(=O)—O—$C_{1-6}$alkyl and $R^{3b}$ represents hydrogen, can also be converted into a compound of formula (I) wherein $R^{3a}$ represents $C_{1-6}$alkyl substituted with —C(=O)—$NR^{10}R^{11}$ and $R^{3b}$ represents hydrogen, by reaction with $NHR^{10}R^{11}$.

Compounds of formula (I) wherein $R^{3a}$ represents $C_{1-5}$alkyl substituted with oxiranyl, can be converted into a compound of formula (I) wherein $R^{3a}$ represents $C_{1-6}$alkyl substituted with hydroxyl and $NR^{10}R^{11}$, by reaction with $NHR^{10}R^{11}$ in the presence of a suitable solvent, such as for example N,N-dimethylformamide and an alcohol, e.g. ethanol.

Compounds of formula (I) wherein $R^{3a}$ represents $C_{1-5}$alkyl substituted with —C(=O)—$C_{1-6}$alkyl, e.g —$CH_2$—C(=O)—$CH_3$, can be converted into a compound of formula (I) wherein $R^{3a}$ represents $C_{1-6}$alkyl substituted with oxiranyl, by reaction with trimethylsulphoxonium iodide in the presence of a suitable base, such as for example potassium tert butoxide, and a suitable solvent, such as for example dimethoxymethane and dimethylsulfoxide.

Compounds of formula (I) wherein $R^1$ represents tetrahydropyranyl can be converted into a compound of formula (I) wherein $R^1$ represents hydrogen, by reaction with a suitable acid, such as for example HCl or trifluoroacetic acid, in the presence of a suitable solvent, such as for example dichloromethane, dioxane, or an alcohol, e.g. methanol, isopropanol and the like.

Compounds of formula (I) wherein $R^1$ or $R^{3a}$ represent $C_{1-6}$alkyl-OH, can be converted into a compound of formula (I) wherein $R^1$ or $R^{3a}$ represent $C_{1-6}$alkyl-F by reaction with diethylaminosulfur trifluoride in the presence of a suitable solvent, such as for example dichloromethane and in the presence of catalytic amounts of an alcohol, such as for example ethanol. Likewise, a compound of formula (I) wherein $R^1$ or $R^{3a}$ represent $C_{1-6}$alkyl substituted with $R^6$ or $R^9$ wherein said $R^6$ or $R^9$ is substituted with OH, can be converted into a compound of formula (I) wherein $R^1$ or $R^{3a}$ represent $C_{1-6}$alkyl substituted with $R^6$ or $R^9$ wherein said $R^6$ or $R^9$ is substituted with F, by reaction with diethylaminosulfur trifluoride in the presence of a suitable solvent, such as for example dichloromethane.

Compounds of formula (I) wherein $R^1$ or $R^{3a}$ represent $C_{1-6}$alkyl substituted with $R^6$ or $R^9$ wherein said $R^6$ or $R^9$ is substituted with —C(=O)—O—$C_{1-6}$alkyl, can be converted into a compound of formula (I) wherein $R^1$ or $R^{3a}$ represent $C_{1-6}$alkyl substituted with $R^6$ or $R^9$ wherein said $R^6$ or $R^9$ is substituted with —$CH_2$—OH, by reaction with $LiAlH_4$ in the presence of a suitable solvent, such as for example tetrahydrofuran.

Compounds of formula (I) wherein $R^{3a}$ represents $C_{1-6}$alkyl substituted with 1,3-dioxo-2H-isoindol-2-yl, can be converted into a compound of formula (I) wherein $R^{3a}$ represents $C_{1-6}$alkyl substituted with amino, by reaction with hydrazine monohydrate in the presence of a suitable solvent, such as for example an alcohol, e.g. ethanol.

Compounds of formula (I) wherein $R^1$ or $R^{3a}$ represent $C_{1-6}$alkyl substituted with amino, can be converted into a compound of formula (I) wherein $R^1$ or $R^{3a}$ represents $C_{1-6}$alkyl substituted with —NH—S(=O)$_2$—$C_{1-6}$alkyl, by reaction with Cl—S(=O)$_2$—$C_{1-6}$alkyl in the presence of a suitable base, such as for example triethylamine, and a suitable solvent, such as for example dichloromethane.

Compounds of formula (I) wherein $R^1$ or $R^{3a}$ represents $C_{1-6}$alkyl substituted with halo, can be converted into a compound of formula (I) wherein $R^1$ or $R^{3a}$ represent $C_{1-6}$alkyl substituted with $NR^4R^5$ or $NR^{10}R^{11}$, by reaction with $NHR^4R^5$ or $NHR^{10}R^{11}$, either using such amino in large excess or in the presence of a suitable base, such as for example $K_2CO_3$, and a suitable solvent, such as for example acetonitrile, N,N-dimethylacetamide or 1-methyl-pyrrolidinone.

Compounds of formula (I) wherein $R^1$ represents hydrogen, can be converted into a compound of formula (I) wherein $R^1$ represents polyhalo$C_{1-6}$alkyl or polyhydroxy$C_{1-6}$alkyl or $C_{1-6}$alkyl or —S(=O)$_2$—$NR^{14}R^{15}$ or —S(=O)$_2$—$C_{1-6}$alkyl, by reaction with polyhalo$C_{1-6}$alkyl-W or polyhydroxy$C_{1-6}$alkyl-W or $C_{1-6}$alkyl-W or W—S(=O)$_2$—$NR^{14}R^{15}$ or W—S(=O)$_2$—$C_{1-6}$alkyl, wherein W represents a suitable leaving group, such as for example halo, e.g. bromo and the like, in the presence of a suitable base, such as for example sodium hydride or $K_2CO_3$ or triethylamine or 4-dimethylamino-pyridine or diisopropylamine, and a suitable solvent, such as for example N,N-dimethylformamide or acetonitrile or dichloromethane.

Compounds of formula (I) wherein $R^1$ represents hydrogen can also be converted into a compound of formula (I) wherein $R^1$ represents $C_{1-6}$alkyl-OH, by reaction with W—$C_{1-6}$alkyl-O—$Si(CH_3)_2(C(CH_3)_3)$ in the presence of a suitable base, such as for example sodium hydride, and a suitable solvent, such as for example N,N-dimethylformamide.

Compounds of formula (I) wherein $R^1$ represents hydrogen, can also be converted into a compound of formula (I) wherein $R^1$ represents ethyl substituted with —S(=O)$_2$—$C_{1-6}$alkyl, by reaction with $C_{1-6}$alkyl-vinylsulfone, in the presence of a suitable base, such as for example triethylamine, and a suitable solvent, such as for example an alcohol, e.g. methanol or by reaction with $C_{1-6}$alkyl-2-bromoethylsulfone in the presence of a suitable deprotonating agent, such as for example NaH, and a suitable solvent, such as for example dimethylormamide.

Compounds of formula (I) wherein $R^1$ represents hydrogen can also be converted into a compound of formula (I) wherein $R^1$ represents

by reaction with

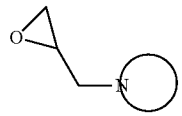

in the presence of a suitable base, such as for example sodium hydride, and a suitable solvent, such as for example N,N-dimethylformamide.

Compounds of formula (I) wherein $R^1$ represents $C_{1-6}$alkyl substituted with $R^6$ wherein said $R^6$ is substituted with —C(=O)—O—$C_{1-6}$alkyl or —S(=O)$_2$—NR$^{14}$R$^{15}$ or wherein $R^{3a}$ represents $C_{1-6}$alkyl substituted with $R^9$ wherein said $R^9$ is substituted with —C(=O)—O—$C_{1-6}$alkyl or —S(=O)$_2$—NR$^{14}$R$^{15}$, can be converted into a compound of formula (I) wherein the $R^6$ or $R^9$ is unsubstituted, by reaction with a suitable acid, such as for example HCl and a suitable solvent, such as for example dioxane, acetonitrile or an alcohol, e.g. isopropylalcohol. Compounds of formula (I) wherein $R^1$ represents $C_{1-6}$alkyl substituted with $R^6$ wherein said $R^6$ is a ring moiety comprising a nitrogen atom which is substituted with —CH$_2$—OH or wherein $R^{3a}$ represents $C_{1-6}$alkyl substituted with $R^9$ wherein said $R^9$ is a ring moiety comprising a nitrogen atom which is substituted with —CH$_2$—OH, can be converted into a compound of formula (I) wherein the $R^6$ or $R^9$ is unsubstituted, by reaction with sodium hydroxide, in the presence of a suitable solvent, such as for example tetrahydrofuran.

Compounds of formula (I) wherein $R^1$ represents $C_{1-6}$alkyl substituted with $R^6$ or $R^{3a}$ represents $C_{1-6}$alkyl substituted with $R^9$, wherein said $R^6$ or said $R^9$ is unsubstituted, can be converted into a compound of formula (I) wherein said $R^6$ or said $R^9$ is substituted with $C_{1-6}$alkyl, by reaction with W—$C_{1-6}$alkyl wherein W is as defined above, in the presence of a suitable base. Such as for example sodium hydride, and a suitable solvent, such as for example N,N-dimethylformamide.

Compounds of formula (I) wherein $R^1$ or $R^{3a}$ represent hydroxy$C_{1-6}$alkyl, can be converted into the corresponding carbonyl compound, by reaction with dess-Martin-periodinane, in the presence of a suitable solvent, such as for example dichloromethane.

Compounds of formula (I) wherein $R^1$ represents $C_{1-6}$alkyl substituted with $R^6$ or $R^{3a}$ represents $C_{1-6}$alkyl substituted with $R^9$, wherein said $R^6$ or said $R^9$ is substituted with $C_{1-6}$alkyl-halo, can be converted into a compound of formula (I) wherein said $R^6$ or said $R^9$ is substituted with $C_{1-6}$alkyl-CN, by reaction with sodium cyanide, in the presence of a suitable solvent, such as for example water or an alcohol, e.g. ethanol.

Compounds of formula (I) wherein $R^1$ represents $C_{1-6}$alkyl substituted with $R^6$ wherein said $R^6$ is unsubstituted or wherein $R^{3a}$ represents $C_{1-6}$alkyl substituted with $R^9$ wherein said $R^9$ is unsubstituted, can be converted into a compound of formula (I) wherein $R^6$ or $R^9$ is substituted with —CH$_3$ or —CH(CH$_3$)$_2$, by reaction with formaldehyde or acetone and NaBH$_3$CN, in the presence of a suitable solvent, such as for example tetrahydrofuran or an alcohol, e.g. methanol.

Compounds of formula (I) wherein $R^1$ contains a $R^6$ substituent substituted with OH or wherein $R^{3a}$ contains a $R^9$ substituent substituted with OH, can be converted into a compound of formula (I) wherein the $R^6$ or $R^9$ substituent is substituted with $C_{1-6}$alkyloxy, by reaction with W—$C_{1-6}$alkyl, in the presence of a suitable base, such as for example sodium hydride, and a suitable solvent, such as for example N,N-dimethylformamide.

Compounds of formula (I) wherein $R^{3a}$ represents $C_{1-6}$alkyl substituted with —C(=O)—O—$C_{1-6}$alkyl, can be converted into a compound of formula (I) wherein $R^{3a}$ represents $C_{1-6}$alkyl substituted with COOH, by reaction with LiOH in the presence of a suitable solvent, such as for example tetrahydrofuran. Said compounds of formula (I) wherein $R^{3a}$ represents $C_{1-6}$alkyl substituted with COOH, can be converted into a compound of formula (I) wherein $R^{3a}$ represents $C_{1-6}$alkyl substituted with —C(=O)—NH$_2$ or —C(=O)—NHCH$_3$, by reaction with NH(Si(CH$_3$)$_3$)$_2$ or MeNH$_3^+$Cl$^-$ in the presence of suitable peptide coupling reagents such as for example 1-(3-dimethylaminopropyl)-3-ethylcarbodiimide HCl and 1-hydroxybenzotriazole, a suitable base, such as for example triethylamine and a suitable solvent such as for example dichloromethane. Compounds of formula (I) wherein $R^{3a}$ represents $C_{1-6}$alkyl substituted with —C(=O)—O—$C_{1-6}$alkyl, can also be converted into a compound of formula (I) wherein $R^{3a}$ represents $C_{1-6}$alkyl substituted with 2-imidazolyl, by reaction under N$_2$ with ethylenediamine and trimethylaluminium in the presence of a suitable solvent, such as for example toluene and heptane. This compound of formula (I) wherein $R^{3a}$ represents $C_{1-6}$alkyl substituted with 2-imidazolyl, can be converted into a compound of formula (I) wherein $R^{3a}$ represents $C_{1-6}$alkyl substituted with —C(=O)—NH—(CH$_2$)$_2$—NH$_2$ by reaction with sodium hydroxide.

Compounds of formula (I) wherein $R^{3a}$ represents $C_{1-6}$alkyl substituted with

can be converted into a compound of formula (I) wherein $R^{3a}$ represents $C_{1-6}$alkyl substituted with 2 OH's, by reaction with a suitable acid, such as for example trifluoroacetic acid, and a suitable solvent, such as for example dioxane or water. These compounds of formula (I) wherein $R^{3a}$ represents $C_{1-6}$alkyl substituted with

can also be converted into a compound of formula (I) wherein $R^{3a}$ represents $C_{1-6}$alkyl substituted with OH and NR$^{10}$R$^{11}$, by reaction with NH$_2$R$^{10}$R$^{11}$ optionally in salt form, such as for example NHR$^{10}$R$^{11+}$Cl$^-$, optionally in the presence of a suitable base, such as for example sodium hydride or Na$_2$CO$_3$ or triethylamine or KI, and in the presence of a suitable solvent, such as for example N,N-dimethylformamide or an alcohol, e.g. 1-butanol or ethanol.

Compounds of formula (I) wherein $R^{3a}$ represents $C_{1-3}$alkyl substituted with —C(=O)—O—$C_{1-6}$alkyl, can be converted into a compound of formula (I) wherein $R^{3a}$ represents $C_{1-3}$alkyl substituted with —C(CH$_3$)$_2$—OH, by reaction with iodomethane and Mg powder, in the presence of a suitable solvent, such as for example diethylether or tetrahydrofuran.

Compounds of formula (I) wherein $R^{3a}$ represents —CH$_2$—CH=CH$_2$, can be converted into a compound of formula (I) wherein $R^{3a}$ represents —CH$_2$—CHOH—CH$_2$—OH, by reaction with potassium permanganate, and a suitable solvent, such as for example acetone or water.

Compounds of formula (I) wherein $R^{3a}$ represents $C_{1-6}$alkyl substituted with —C(=O)—$C_{1-4}$alkyl, can be converted into a compound of formula (I) wherein $R^{3a}$ represents $C_{1-6}$alkyl substituted with —C($C_{1-4}$alkyl)=N—OH, by reaction with hydroxylamine, in the presence of a suitable base, such as for example pyridine, and a suitable solvent, such as for example an alcohol, e.g. ethanol.

Compounds of formula (I) wherein $R^{3a}$ represents $C_{1-6}$alkyl substituted with NH$_2$, can be converted into a compound of formula (I) wherein $R^{3a}$ represents $C_{1-6}$alkyl substituted with —NH—C(=O)—$R^6$ or with —NH—C(=O)—$C_{1-6}$alkyl or with —NH—C(=O)-polyhydroxy$C_{1-6}$alkyl or with —NH—C(=O)-polyhalo$C_{1-6}$alkyl or with —NH—C(=O)-polyhydroxypolyhaloCvalkyl, by reaction with the corresponding COOH analogue, e.g. $R^6$—COOH or CF$_3$—C(CH$_3$)(OH)—COOH and the like, in the presence of suitable peptide coupling reagents such as 1-hydroxy-benzotriazole and 1-(3-dimethylamino)propyl)carbodiimide optionally in the presence of a suitable base, such as for example triethylamine. Said compounds of formula (I) wherein $R^{3a}$ represents $C_{1-6}$alkyl substituted with NH$_2$, can also be converted into a compound of formula (I) wherein $R^{3a}$ represents $C_{1-6}$alkyl substituted with NH—C(=O)—CF$_3$, by reaction with trifluoroacetic anhydride, in the presence of a suitable base, such as for example triethylamine, and a suitable solvent, such as for example tetrahydrofuran. Said compounds of formula (I) wherein $R^{3a}$ represents $C_{1-6}$alkyl substituted with NH$_2$, can also be converted into a compound of formula (I) wherein $R^{3a}$ represents $C_{1-6}$alkyl substituted with —NH-polyhalo$C_{1-6}$alkyl, e.g. —NH—CH$_2$—CH$_2$—F, by reaction with polyhalo$C_{1-6}$alkyl-W, with W as defined above, e.g. iodo-2-fluoroethane, in the presence of a suitable base, such as for example K$_2$CO$_3$, and a suitable solvent, such as for example N,N-dimethylformamide or dioxane.

Compounds of formula (I) wherein $R^{3a}$ represents $C_{1-6}$alkyl substituted with cyano, can be converted into a compound of formula (I) wherein $R^{3a}$ represents $C_{1-6}$alkyl substituted with tetrazolyl by reaction with sodium azide, and NH$_4^+$Cl$^-$ in the presence of a suitable solvent, such as for example N,N-dimethylformamide.

Compounds of formula (I) wherein $R^{3a}$ represents —CH$_2$—C≡CH, can be converted into a compound of formula (I) wherein $R^{3a}$ represents

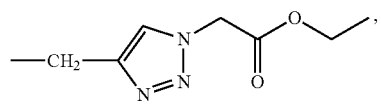

by reaction with ethyl azidoacetate in the presence of CuI and a suitable base, such as for example diisopropylamine, and a suitable solvent, such as for example tetraydrofuran.

Compounds of formula (I) wherein $R^{3a}$ represents —CH$_2$—C≡CH, can be converted into a compound of formula (I) wherein $R^{3a}$ represents

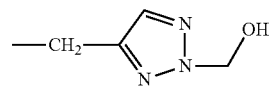

by reaction with sodium azide and formaldehyde, in the presence of a suitable catalyst, such as for example CuSO$_4$ and sodium L ascorbate, a suitable acid, such as for example acetic acid, and a suitable solvent, such as for example dioxane.

Compounds of formula (I) wherein $R^{3a}$ represent $C_{2-6}$alkynyl, can be converted into a compound of formula (I) wherein $R^{3a}$ represents $C_{2-6}$alkynyl substituted with $R^9$, by reaction with W—$R^9$ wherein W is as defined above, in the presence of a suitable catalyst, such as for example dichlorobis(triphenylphosphine)palladium, a suitable co-catalyst such as CuI, a suitable base, such as for example triethylamine, and a suitable solvent, such as for example dimethylsulfoxide.

Compounds of formula (I) wherein $R^{3a}$ represents $C_{1-6}$alkyl substituted with NR$^{10}$(benzyl) can be converted into a compound of formula (I) wherein $R^{3a}$ represents $C_{1-6}$alkyl substituted with NHR$^{10}$, by reaction with 1-chloroethylchloroformate in the presence of a suitable solvent, such as for example dichloromethane Compounds of formula (I) wherein $R^2$ represents halo, e.g. bromo, can be converted into a compound of formula (I) wherein $R^2$ represents cyano, by reaction with zinc cyanide, in the presence of a suitable catalyst, such as for example Pd$_2$(dba)$_3$ and a suitable ligand, such as for example 1,1-bis(diphenylphosphino)ferrocene, in the presence of a suitable solvent, such as for example N,N-dimethylformamide. Said $R^2$ substituent being cyano can be converted into —CH$_2$—NH$_2$ by hydrogenation in the presence of NH$_3$ and Nickel.

A further aspect of the invention is a process for the preparation of a compound of formula (I) as defined herein, which process comprises:

(I) reacting an intermediate of formula (IV) wherein W$_1$ represents a suitable leaving group, with an intermediate of formula (V) in the presence of a suitable catalyst, a suitable base, and a suitable solvent or solvent mixture,

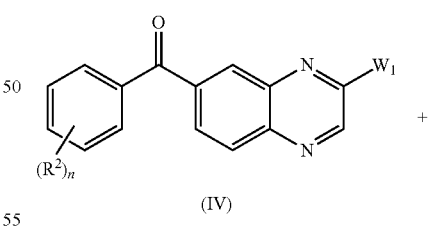

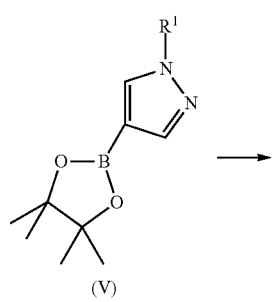

-continued

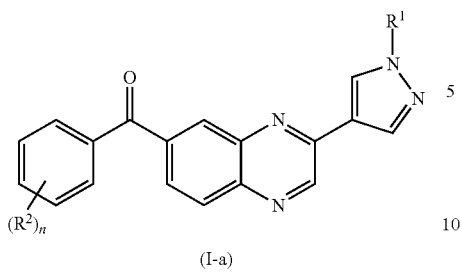
(I-a)

With $R^1$, $R^2$ and n as defined herein;

(IIa) reacting an intermediate of formula (VI) wherein $W_3$ represents a suitable leaving group, with an intermediate of formula (XIII) in the presence of CO, a suitable catalyst, a suitable ligand, a suitable base, and a suitable solvent,

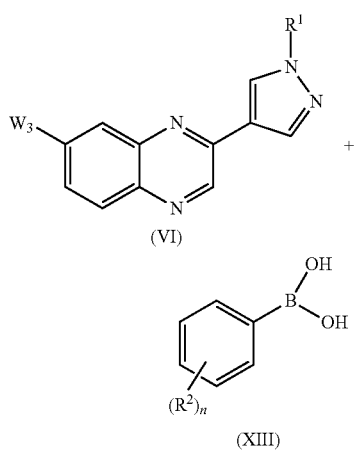

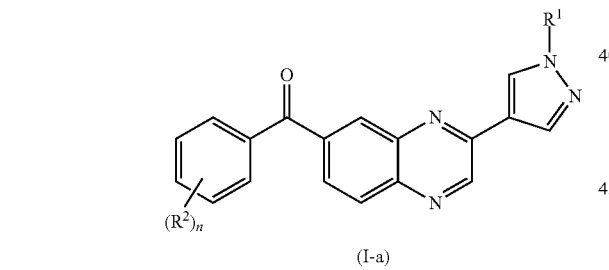
(I-a)

With $R^1$, $R^2$ and n as defined herein;

(IIb) reacting an intermediate of formula (VI') wherein $W_3$ represents a suitable leaving group, with an intermediate of formula (XIII) in the presence of CO, a suitable catalyst, a suitable ligand, a suitable base, and a suitable solvent,

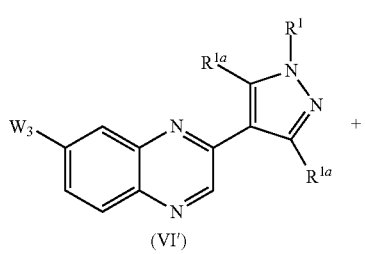

-continued

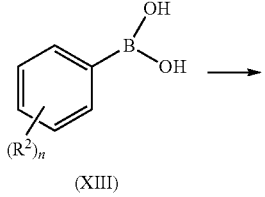
(XIII)

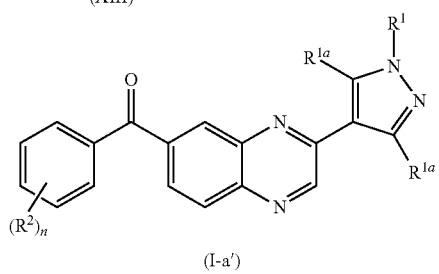
(I-a')

With $R^1$, $R^2$, $R^{1a}$ and n as defined herein;

(IIIa) reacting an intermediate of formula (VII) with an intermediate of formula (VIII) wherein $W_2$ represents a suitable leaving group, in the presence of a catalyst, a suitable base, and a suitable solvent,

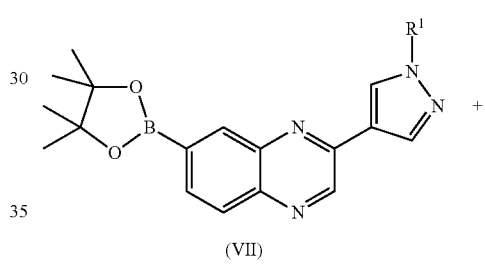
(VII)

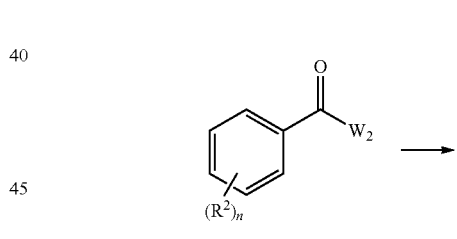
(VIII)

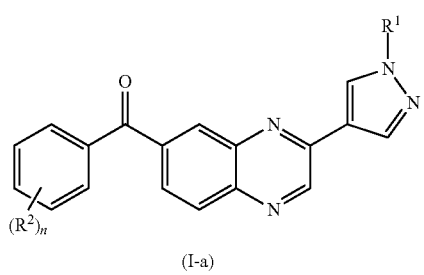
(I-a)

With $R^1$, $R^2$ and n as defined herein;

(IIIb) reacting an intermediate of formula (VII') with an intermediate of formula (VIII) wherein $W_2$ represents a suitable leaving group, in the presence of a catalyst, a suitable base, and a suitable solvent,

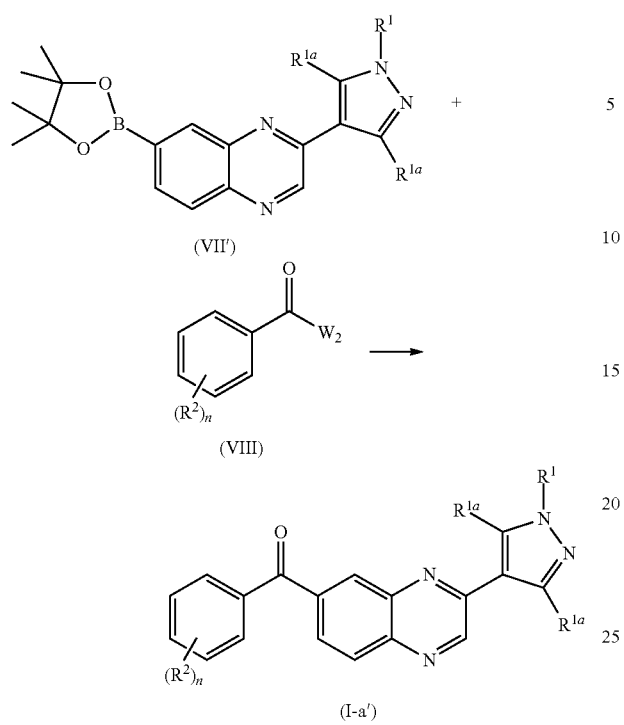

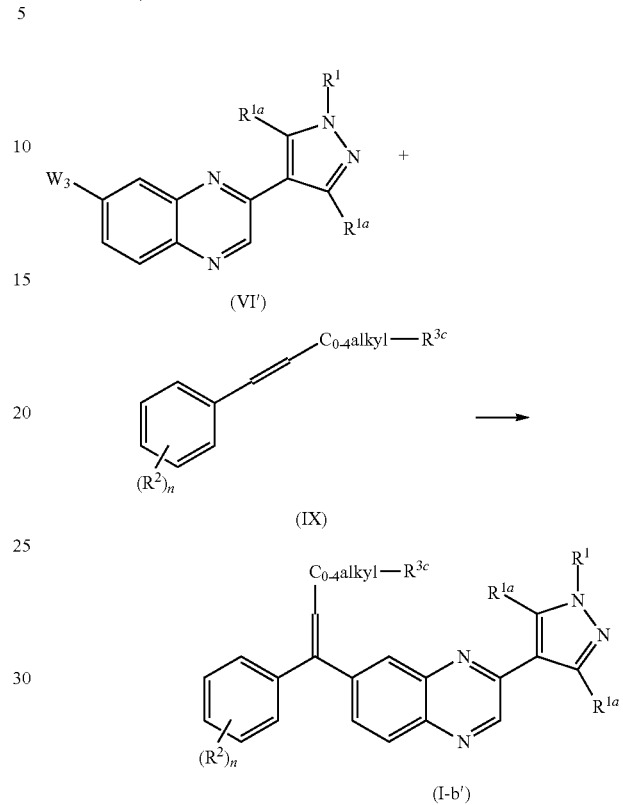

With $R^1$, $R^2$, $R^{1a}$ and n as defined herein;

(IVa) reacting an intermediate of formula (VI) with an intermediate of formula (IX) in the presence of a suitable catalyst, a suitable base, a suitable solid base, and a suitable solvent, (IVb) reacting an intermediate of formula (VI') with an intermediate of formula (IX) in the presence of a suitable catalyst, a suitable base, a suitable solid base, and a suitable solvent, With $R^1$, $R^2$, $R^{1a}$, $R^{3c}$ and n as defined herein;

(Va) reacting an intermediate of formula (XI) with an intermediate of formula (XII) wherein $W_4$ represents a suitable leaving group, in the presence of a suitable catalyst, a suitable base, a suitable solid base, and a suitable solvent,

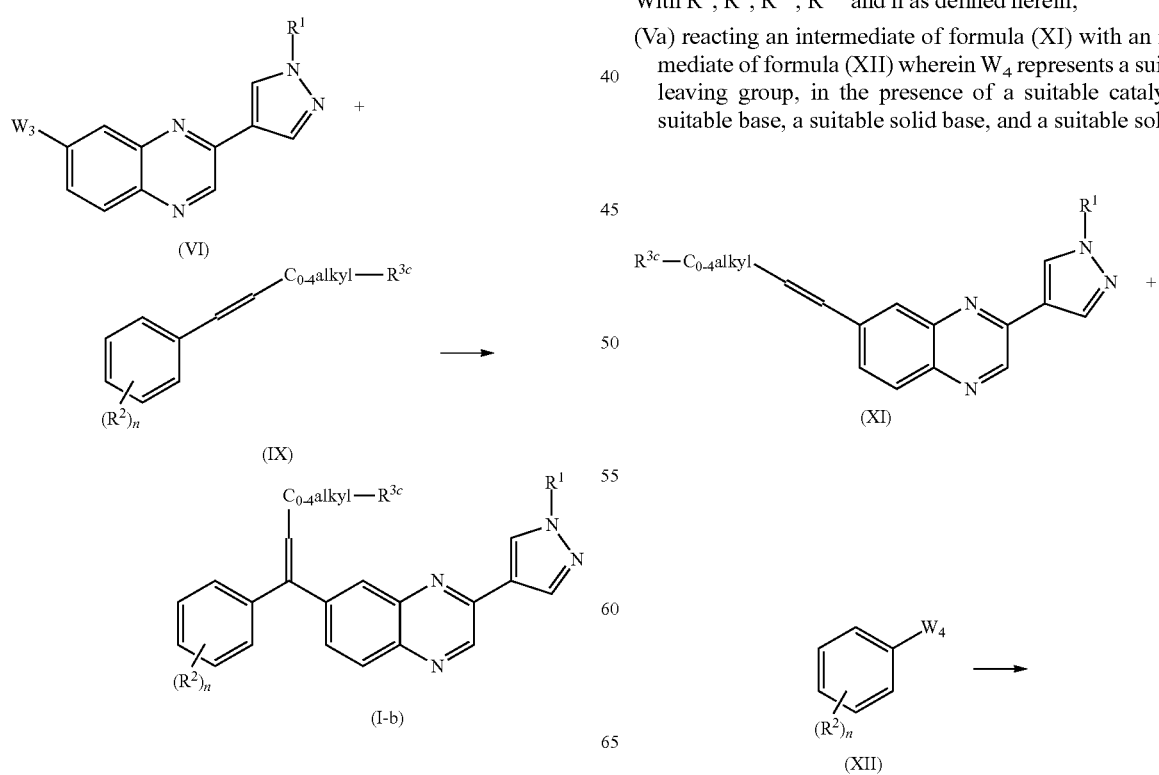

With $R^1$, $R^2$, $R^{3c}$ and n as defined herein;

-continued

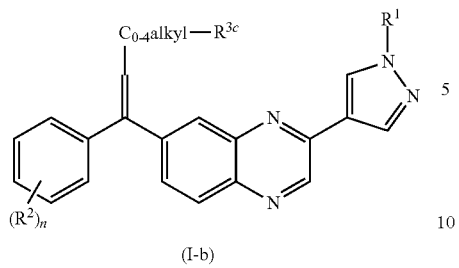

(I-b)

With $R^1$, $R^2$, $R^{3c}$ and n as defined herein;

(Vb) reacting an intermediate of formula (XI') with an intermediate of formula (XII) wherein $W_4$ represents a suitable leaving group, in the presence of a suitable catalyst, a suitable base, a suitable solid base, and a suitable solvent,

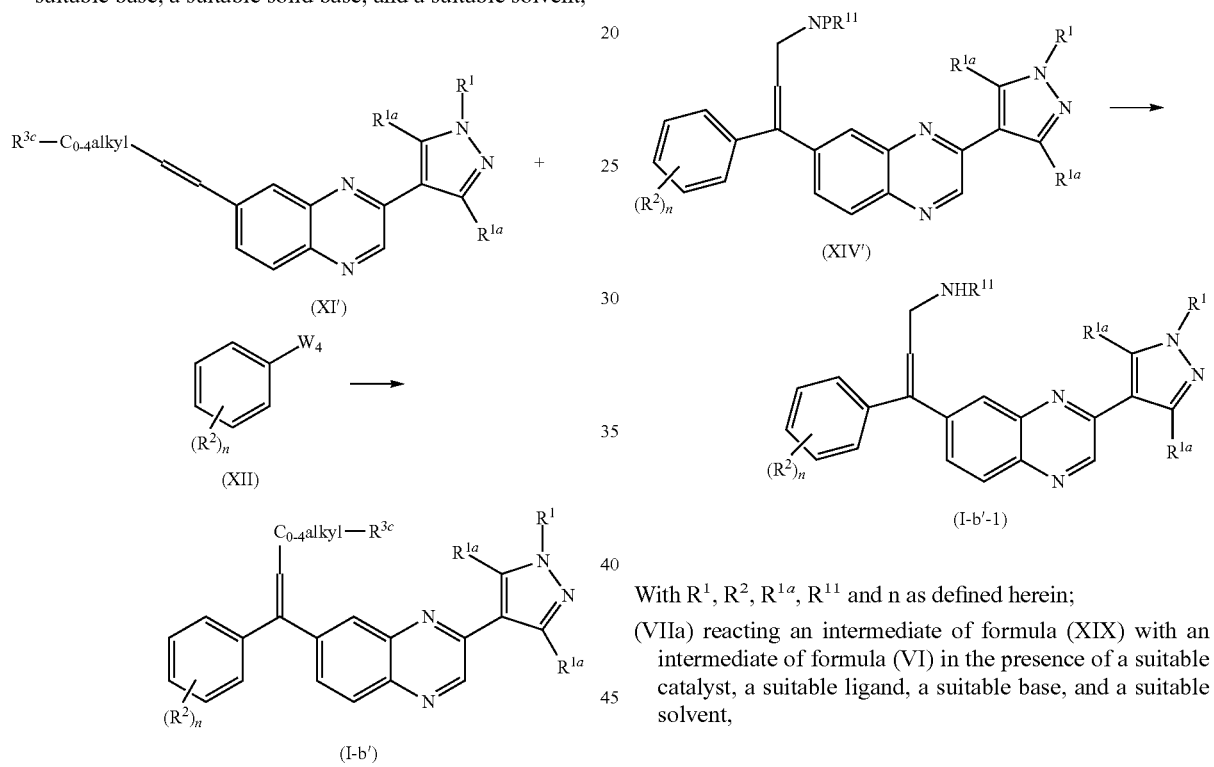

(XI')

+

(XII)

(I-b')

With $R^1$, $R^2$, $R^{1a}$, $R^{3c}$ and n as defined herein;

(VIa) deprotecting an intermediate of formula (XIV) in the presence of a suitable acid and a suitable solvent,

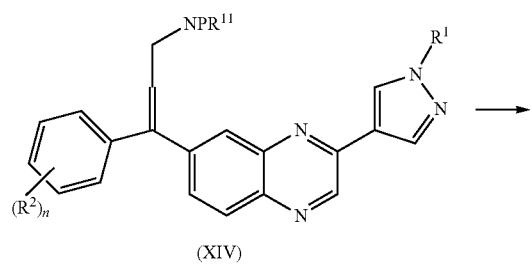

(XIV)

-continued

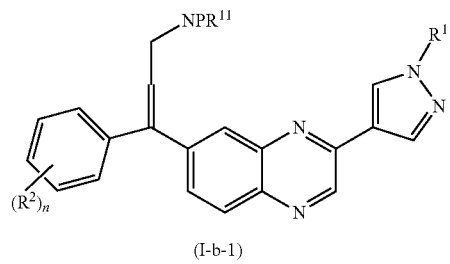

(I-b-1)

With $R^1$, $R^2$, $R^{11}$ and n as defined herein;

(VIb) deprotecting an intermediate of formula (XIV') in the presence of a suitable acid and a suitable solvent, (XIV')

(I-b'-1)

With $R^1$, $R^2$, $R^{1a}$, $R^{11}$ and n as defined herein;

(VIIa) reacting an intermediate of formula (XIX) with an intermediate of formula (VI) in the presence of a suitable catalyst, a suitable ligand, a suitable base, and a suitable solvent,

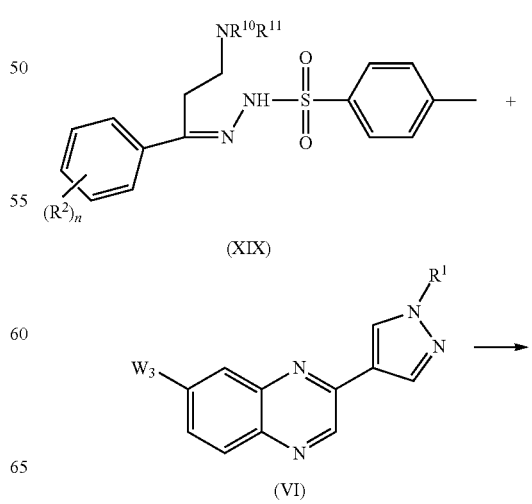

(XIX)

+

(VI)

-continued

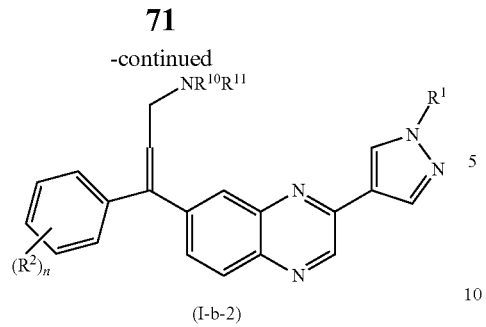
(I-b-2)

With $R^1$, $R^2$, $R^{10}$, $R^{11}$ and n as defined herein;

(VIIb) reacting an intermediate of formula (XIX) with an intermediate of formula (VI') in the presence of a suitable catalyst, a suitable ligand, a suitable base, and a suitable solvent,

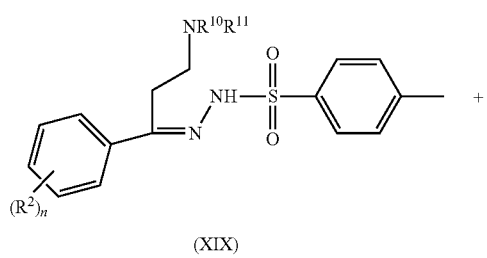
(XIX)

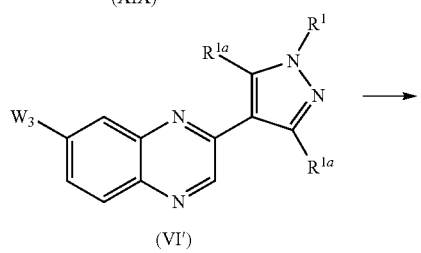
(VI')

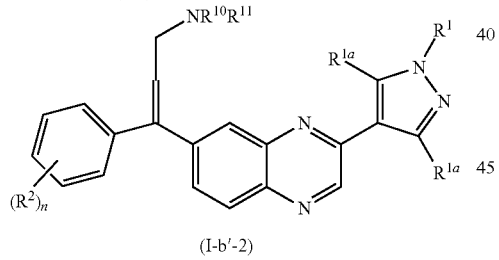
(I-b'-2)

With $R^1$, $R^2$, $R^{1a}$, $R^{10}$, $R^{11}$ and n as defined herein;

(VIIIa) reacting an intermediate of formula (XXI) with a suitable reducing agent and a suitable solvent,

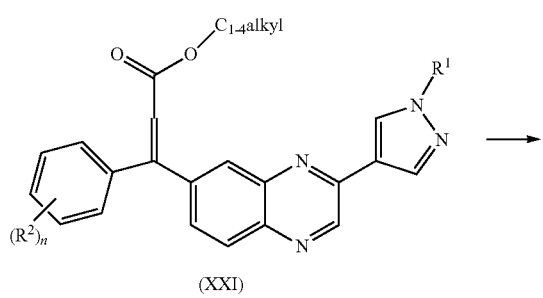
(XXI)

-continued

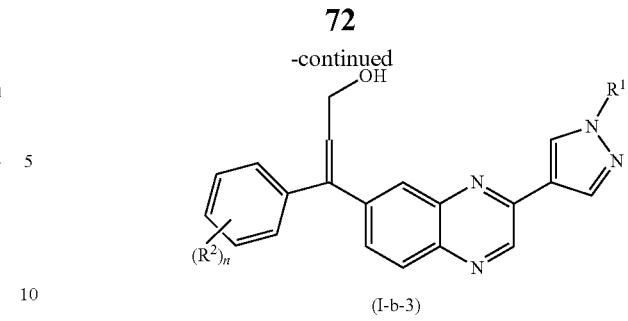
(I-b-3)

With $R^1$, $R^2$, and n as defined herein;

(VIIIb) reacting an intermediate of formula (XXI') with a suitable reducing agent and a suitable solvent,

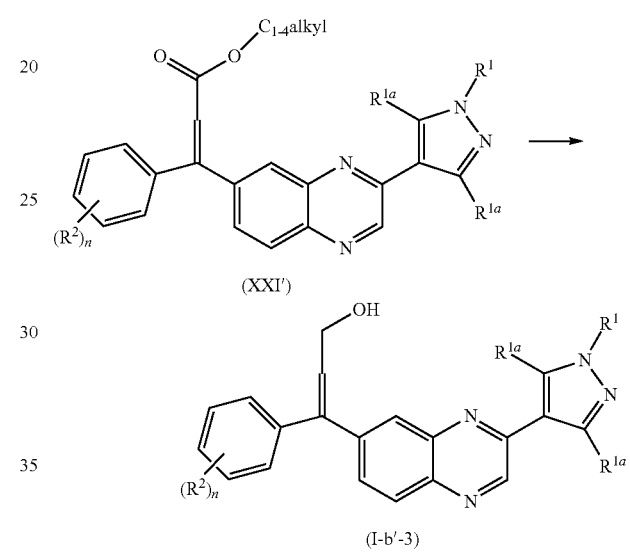
(XXI')

(I-b'-3)

With $R^1$, $R^2$, $R^{1a}$, and n as defined herein;

(IXa) reacting an intermediate of formula (XXIII) wherein $W_5$ represents a suitable leaving group, with $NHR^{11}$ in the presence of a suitable solvent,

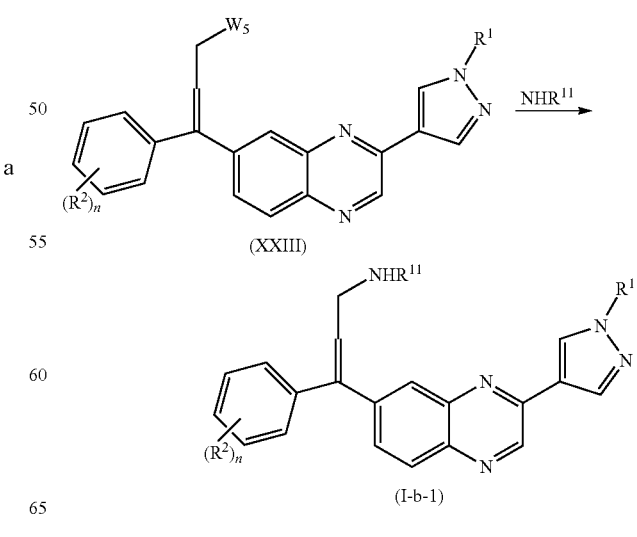
(XXIII)

(I-b-1)

With R$^1$, R$^2$, R$^{11}$ and n as defined herein;

(IXb) reacting an intermediate of formula (XXIII') wherein W$_5$ represents a suitable leaving group, with NHR$^{11}$ in the presence of a suitable solvent,

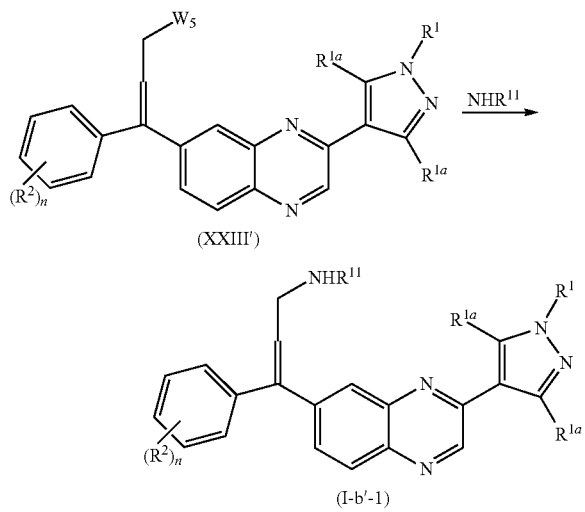

With R$^1$, R$^2$, R$^{1a}$, R$^{11}$ and n as defined herein;

(Xa) reacting an intermediate of formula (XXI) with magnesium in the presence of a suitable solvent,

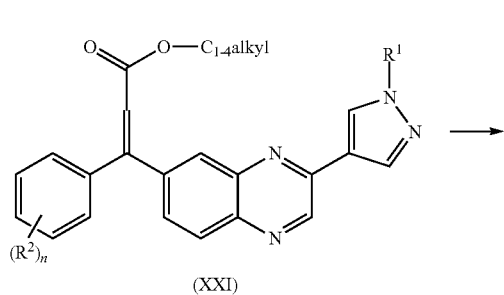

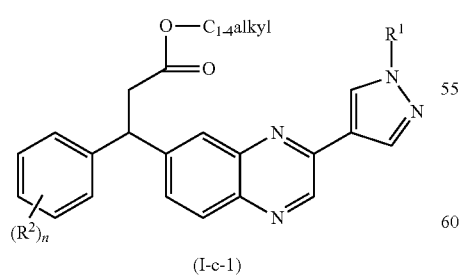

With R$^1$, R$^2$ and n as defined herein;

(Xb) reacting an intermediate of formula (XXI') with magnesium in the presence of a suitable solvent, With R$^1$, R$^2$, R$^{1a}$ and n as defined herein;

(XIa) reacting an intermediate of formula (XXIV) with potassium cyanide in the presence of a suitable solvent,

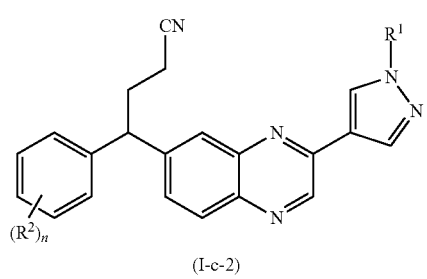

With R$^1$, R$^2$ and n as defined herein;

(XIb) reacting an intermediate of formula (XXIV') with potassium cyanide in the presence of a suitable solvent,

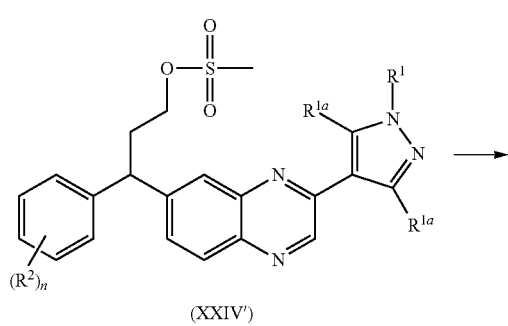

(XXIV')

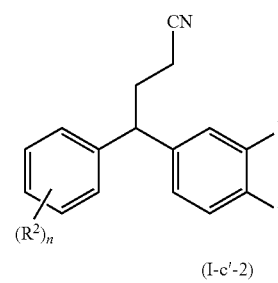

(I-c'-2)

With $R^1$, $R^2$, $R^{1a}$ and n as defined herein;

(XIIa) reacting an intermediate of formula (XXIV) with $HR^9$ in the presence of a suitable base and a suitable solvent,

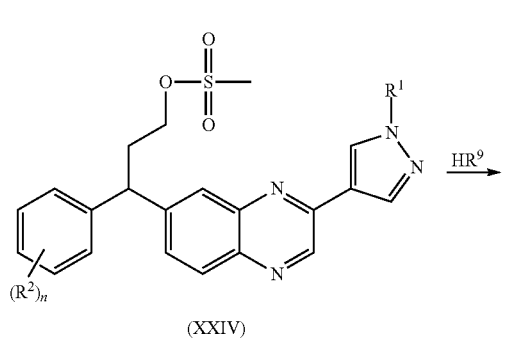

(XXIV)

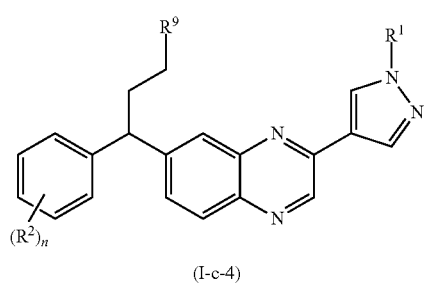

(I-c-4)

With $R^1$, $R^2$, $R^9$ and n as defined herein;

(XIIb) reacting an intermediate of formula (XXIV') with $HR^9$ in the presence of a suitable base and a suitable solvent,

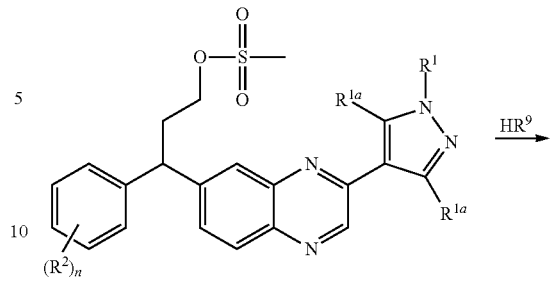

(XXIV')

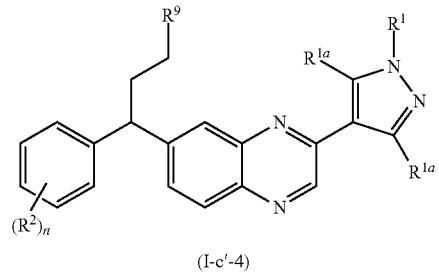

(I-c'-4)

With $R^1$, $R^2$, $R^{1a}$, $R^9$ and n as defined herein;

(XIIIa) reacting an intermediate of formula (XXV) with $NHR^{10}R^{11}$ in the presence of a suitable solvent,

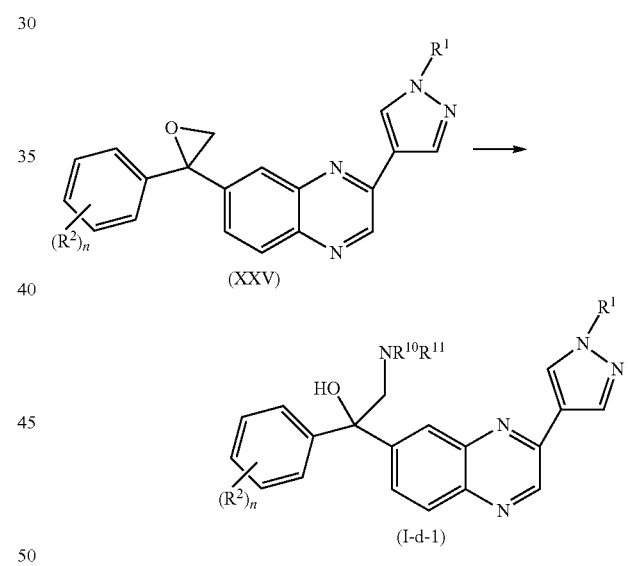

(XXV)

(I-d-1)

With $R^1$, $R^2$, $R^{10}$, $R^{11}$ and n as defined herein;

(XIIIb) reacting an intermediate of formula (XXV') with $NHR^{10}R^{11}$ in the presence of a suitable solvent,

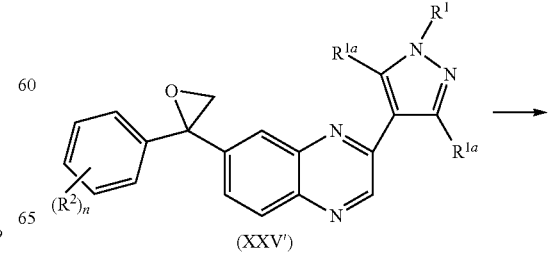

(XXV')

-continued

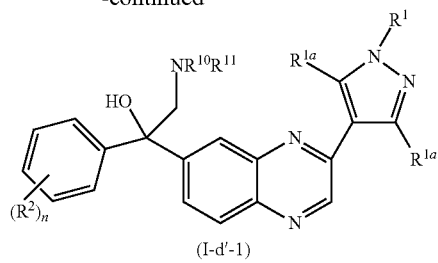
(I-d'-1)

With $R^1$, $R^2$, $R^{1a}$, $R^{10}$, $R^{11}$ and n as defined herein;
(XIVa) reacting an intermediate of formula (XXX) wherein P represents a suitable protective group, with a suitable acid in the presence of a suitable solvent

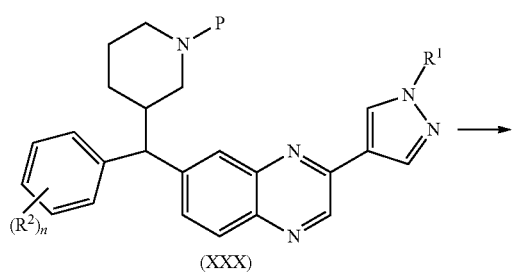
(XXX)

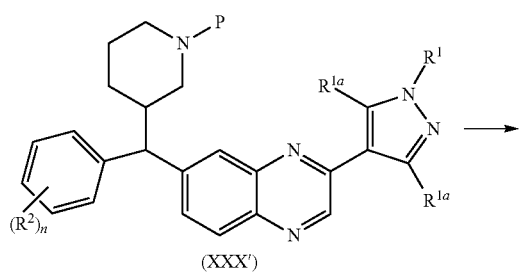
(I-e)

With $R^1$, $R^2$ and n as defined herein;
(XIVb) reacting an intermediate of formula (XXX') wherein P represents a suitable protective group, with a suitable acid in the presence of a suitable solvent

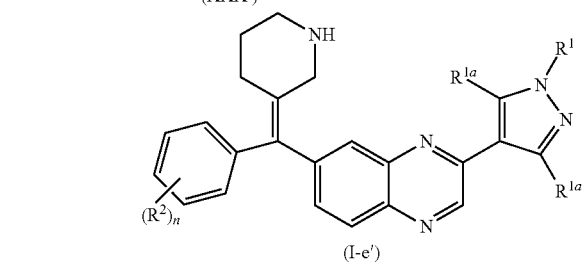
(XXX')

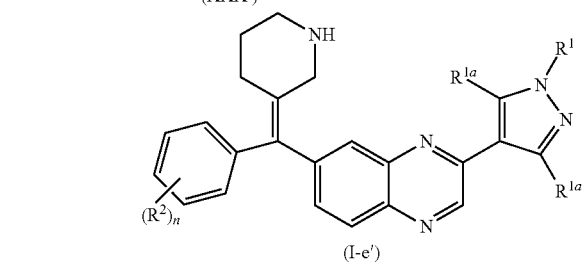
(I-e')

With $R^1$, $R^2$, $R^{1a}$ and n as defined herein;

(XVa) reacting a compound of formula (I-b-3) with a reducing agent $H^{31}$ in the presence of a suitable solvent,

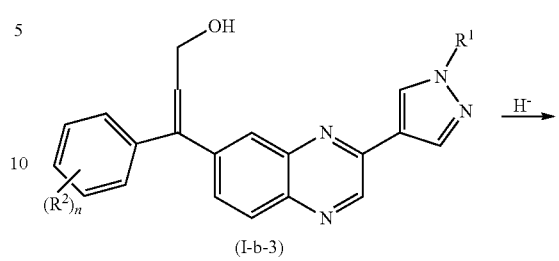
(I-b-3)

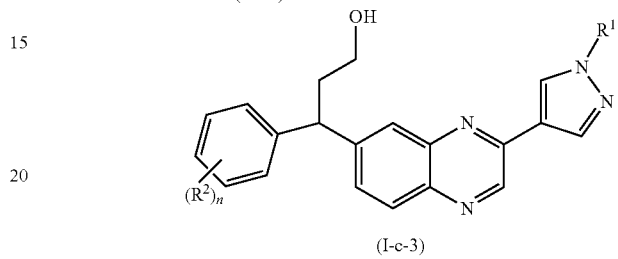
(I-c-3)

With $R^1$, $R^2$ and n as defined herein;
(XVb) reacting a compound of formula (I-b'-3) with a reducing agent $H^{31}$ in the presence of a suitable solvent,

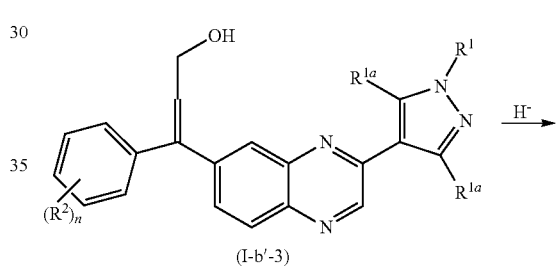
(I-b'-3)

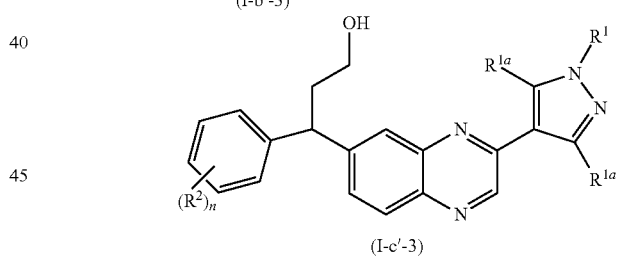
(I-c'-3)

With $R^1$, $R^2$, $R^{1a}$ and n as defined herein;
(XVI) converting one compound of formula (I) into another compound of the formula (I).

In a further embodiment the invention provides a novel intermediate. In one embodiment the invention provides a novel intermediate of formula (II)-(XXV). In another embodiment the invention provides a compound of formula I-a, I'-a, I''-a, I'''-a, I-b, I'-b, I''-b, I'''-b, I'-b', I''-b', I'''-b', I-c, I'-c, I''-c, I'''-c, I-d, I'-d, I''-d, I'''-d, I⁰, I-b-1, I-b-2, I-b-3, I-c-1, I-c-2, I-c-3, I-c-4, I-d-1, I-e, I-a', I-b', I-b'-1, I-b'-2, I-b'-3, I-c'-1, I-c'-2, I-c'-4, I-d'-1, I-e', I-c'-3.

Pharmaceutically Acceptable Salts, Solvates or Derivatives Thereof

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers (including sterochemical isomers), tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof, even more preferably the salts or tautomers or solvates thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, sterochemical isomer, tautomer, N-oxide or solvate thereof. According to another aspect of the invention there is provided a compound as defined herein or a salt, tautomer, N-oxide or solvate thereof. According to a further aspect of the invention there is provided a compound as defined herein or a salt or solvate thereof. References to compounds of the formula (I) and sub-groups thereof as defined herein include within their scope the salts or solvates or tautomers or N-oxides of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I). Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed by formula (I) are any complexes (e.g. inclusion complexes or clathrates with compounds such as cyclodextrins, or complexes with metals) of the compounds.

Furthermore, the compounds of the present invention may have one or more polymorph (crystalline) or amorphous forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

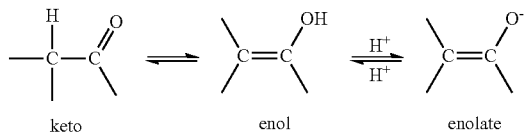

keto    enol    enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.*, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

The compounds of the invention include compounds with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(═O)OR, wherein R is an ester substituent, for example, a $C_{1-6}$ alkyl group, a heterocyclyl group, or a $C_{5-20}$ aryl group, preferably a $C_{1-6}$ alkyl group. Particular examples of ester groups include, but are not limited to, —C(═O)OCH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph.

For example, some prodrugs are esters of the active compound (e.g., a physiologically acceptable metabolically labile ester). By "prodrugs" is meant for example any compound that is converted in vivo into a biologically active compound of the formula (I). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is: $C_{1-6}$alkyl (e.g., -Me, -Et, -nPr, -iPr, -nBu, -sBu, -iBu, -tBu); $C_{1-6}$aminoalkyl [e.g., aminoethyl; 2-(N,N-diethylamino)ethyl; 2-(4-morpholino)ethyl); and acyloxy-$C_{1-7}$alkyl [e.g., acyloxymethyl; acyloxyethyl; pivaloyloxymethyl; acetoxymethyl; 1-acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl]. Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4). Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes. FGFR1 has also been linked to squamous lung cancer, colorectal cancer, glioblastoma, astrocytomas, prostate cancer, small cell lung cancer, melanoma, head and neck cancer, thyroid cancer, uterine cancer.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors. FGFR3 is also linked to endometrial and thyroid cancer.

Over expression of FGFR4 has been linked to poor prognosis in both prostate and thyroid carcinomas. In addition a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated. FGFR4 is also linked to astrocytomas, rhabdomyosarcoma.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent.

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis, ocular diseases, arthritis and hemangioma.

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

There is evidence for normalization of glioblastoma blood vessels in patients treated with a pan-VEGF receptor tyrosine kinase inhibitor, AZD2171, in a phase 2 study. MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3; or in particular the compounds of formula (I) and sub-groups thereof are inhibitors of FGFR4.

Preferred compounds are compounds that inhibit one or more FGFR selected from FGFR1, FGFR2, FGFR3, and FGFR4. Preferred compounds of the invention are those having $IC_{50}$ values of less than 0.1 µM.

Compounds of the invention also have activity against VEGFR.

In addition many of the compounds of the invention exhibit selectivity for the FGFR 1, 2, and/or 3, and/or 4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or 4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, and/or VEGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

The compound of the invention, having FGFR such as FGFR1 inhibitory activity, may be particularly useful in the treatment or prevention of breast cancer in particular Classic Lobular Carcinomas (CLC).

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are useful in the treatment of multiple myeloma (in particular multiple myeloma with t(4;14) translocation or overexpressing FGFR3), prostate cancer (hormone refractory prostate carcinomas), endometrial cancer (in particular endometrial tumours with activating mutations in FGFR2) and breast cancer (in particular lobular breast cancer).

In particular the compounds are useful in the treatment of lobular carcinomas such as CLC (Classic lobular carcinoma).

As the compounds have activity against FGFR3 they will be useful in the treatment of multiple myeloma and bladder cancer.

In particular the compounds are useful for the treatment of t(4;14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric, hepatocellular, uterine, cervix and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC, squamous cell carcinoma, liver cancer, kidney cancer, breast cancer, colon cancer, colorectal cancer, prostate cancer.

The compounds of the invention may be useful in the treatment of cancers with upregulated FGFR. Such cancers include brain (e.g. gliomas), breast, oesophageal, lung and colorectal cancers.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR or VEGFR signalling may be determined by means of a cell growth assay as set out below or by a method as set out in the section headed "Methods of Diagnosis".

The compounds of the invention, and in particular those compounds having FGFR, or VEGFR inhibitory activity, may be particularly useful in the treatment or prevention of cancers of a type associated with or characterised by the presence of elevated levels of FGFR, or VEGFR, for example the cancers referred to in this context in the introductory section of this application.

The compounds of the present invention may be useful for the treatment of the adult population. The compounds of the present invention may be useful for the treatment of the pediatric population.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR, and VEGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment of FGFR-dependent cancer. In one embodiment, the compound as defined herein is for use in the prophylaxis or treatment of cancer mediated by FGFR kinases.

Accordingly, the invention provides inter alia:

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer.

A compound of formula (I) as defined herein for use as a modulator (e.g. inhibitor) of FGFR.

The use of a compound of formula (I) as defined herein for the manufacture of a medicament for the prophylaxis or treatment of a disease state or condition mediated by a FGFR kinase, the compound having the formula (I) as defined herein.

The use of a compound of formula (I) as defined herein for the manufacture of a medicament for the prophylaxis or treatment of a disease state or condition as described herein.

The use of a compound of formula (I) as defined herein for the manufacture of a medicament for the prophylaxis or treatment, in particular the treatment, of cancer.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Methods of Diagnosis

Prior to administration of a compound of the formula (I), a patient may be screened to determine whether a disease or condition from which the patient is or may be suffering is one which would be susceptible to treatment with a compound having activity against FGFR, and/or VEGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, and/or VEGFR or to sensitisation of a pathway to normal FGFR, and/or VEGFR activity, or to upregulation of these growth factor signalling pathways such as growth factor ligand levels or growth factor ligand activity or to upregulation of a biochemical pathway downstream of FGFR, and/or VEGFR activation.

Examples of such abnormalities that result in activation or sensitisation of the FGFR, and/or VEGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T674I of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR or VEGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, and/or VEGFR. The term diagnosis includes screening. By marker we include genetic markers including, for example, the measurement of DNA composition to identify mutations of FGFR, and/or VEGFR. The term marker also includes markers which are characteristic of up regulation of FGFR and/or VEGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, and/or VEGFR may mean that the patient would be particularly suitable for treatment with a FGFR, and/or VEGFR inhibitor. Tumours may preferentially be screened for presence of a FGFR, and/or VEGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, and/or VEGFR, or detection of FGFR, and/or VEGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105.

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcinomas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer.

Therefore in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intra-vaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anticancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoiden for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, caminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
- Inhibitors of the ubiquitin-proteasome pathway for example PS-341, MLN 0.41 or bortezomib;
- Yondelis;
- Telomerase inhibitors for example telomestatin;
- Matrix metalloproteinase inhibitors for example batimastat, marimastat, prinostat or metastat.
- Recombinant interleukins for example aldesleukin, denileukin diftitox, interferon alfa 2a, interferon alfa 2b, peginterferon alfa 2b
- MAPK inhibitors
- Retinoids for example alitretinoin, bexarotene, tretinoin
- Arsenic trioxide
- Asparaginase
- Steroids for example dromostanolone propionate, megestrol acetate, nandrolone (decanoate, phenpropionate), dexamethasone
- Gonadotropin releasing hormone agonists or antagonists for example abarelix, goserelin acetate, histrelin acetate, leuprolide acetate
- Thalidomide, lenalidomide
- Mercaptopurine, mitotane, pamidronate, pegademase, pegaspargase, rasburicase
- BH3 mimetics for example ABT-737
- MEK inhibitors for example PD98059, AZD6244, CI-1040
- colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.
- a steroidal cytochrome P450 17alpha-hydroxylase-17,20-lyase inhibitor (CYP17), e.g. abiraterone, abiraterone acetate.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anti-cancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^{3}$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

General Synthetic Routes

The following examples illustrate the present invention but are examples only and are not intended to limit the scope of the claims in any way.

EXPERIMENTAL PART

Hereinafter, the term 'DCM' means dichloromethane, 'TEA' means triethylamine, 'ACN' means acetonitrile, 'EtOAc' means ethyl acetate, 'DMSO' means dimethylsulfoxide, 'Et$_2$O' means diethyl ether, 'EtOH' means ethanol, 'THF' means tetrahydrofuran, 'DMF' means N,N-dimethylformamide, 'X-Phos' means dicyclohexyl[2',4',6'-tris(1-methylethyl)[1,1'-biphenyl]-2-yl]-phosphine, 'POCl$_3$' means phosphoric trichloride, 'Pd$_2$(dba)$_3$' means tris(dibenzylidene)acetone dipalladium (0), 'SFC' means supercritical fluid chromatography.

A. Preparation of the Intermediates

Example A1

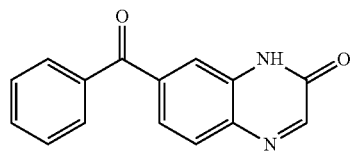 [SMILES: O=C(c1ccccc1)c1ccc2ncc(=O)[nH]c2c1]

a) Preparation of Intermediate 1

A mixture of 3,4-diaminobenzophenone) (1.1 g; 5.2 mmol) and ethyl glyoxalate 50% solution in toluene) (0.77 mL; 3.9 mmol) in ethanol (20 mL) was refluxed overnight. The precipitate was filtered off. The filtrate was evaporated until dryness, taken up in ethyl acetate, washed with brine, dried (MgSO$_4$), filtered off and the solvent was evaporated until dryness. This residue (1.09 g) was purified by chromatography over silica gel [(Irregular SiOH, 15-40 μm, 300 g), mobile phase (Gradient from 0.1% NH$_4$OH, 98% DCM, 2% iPrOH to 0.1% NH$_4$OH, 96% DCM, 4% iPrOH)]. The product fraction was collected and the solvent was evaporated, yielding 263 mg of intermediate 1 (27%).

b) Preparation of Intermediate 2

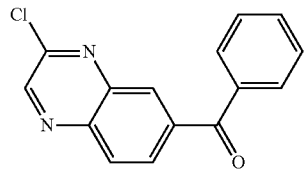 [SMILES: O=C(c1ccccc1)c1ccc2ncc(Cl)nc2c1]

Intermediate 1 (1.5 g; 6 mmol) in POCl$_3$ (15 mL) was heated at 80° C. for 45 minutes, then cooled to room temperature and evaporated until dryness. The crude product was taken up in CH$_2$Cl$_2$, and water was slowly added, then the solution was made basic with 3N NaOH aqueous solution.

The organic layer was dried (MgSO$_4$), filtered off and the solvent was evaporated until dryness, yielding 1.34 g of intermediate 2 (83%).

Example A2

Preparation of Intermediate 3

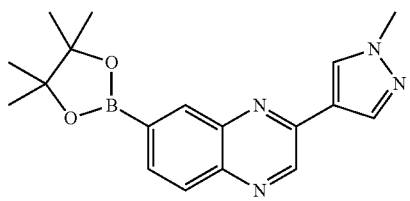 [SMILES: Cn1cc(-c2cnc3ccc(B4OC(C)(C)C(C)(C)O4)cc3n2)cn1]

a) 7-bromo-2(1H)-quinoxalinone (47.2 g; 210 mmol) was added to phosphorus oxychloride (470 mL). The reaction mixture was stirred at 100° C. for 2 hours, cooled down to room temperature and evaporated to dryness. The crude product was taken up into DCM and poured onto ice, water and K$_2$CO$_3$ powder. The mixture was filtered over celite. The celite was washed twice with DCM. The organic layer was decanted, dried over MgSO$_4$, filtered and evaporated to dryness to give 49 g (96%) of 7-bromo-2-chloro-quinoxaline (grey solid). MP=146° C.

7-bromo-2-chloro-quinoxaline was alternatively also prepared using the following procedure:

Thionyl chloride (407.5 mL; 5.59 mol), then N,N-dimethylformamide (34.6 mL; 0.45 mol) were added dropwise to a mixture of 7-bromo-2(1H)-quinoxalinone (500 g; 2.24 mol) in toluene (7.61 L). The reaction mixture was stirred at 80° C. for 17 hours then cooled to 35° C. and poured cautiously onto water. The bi-phasic mixture was stirred for 30 minutes and then decanted. The organic layer was evaporated to dryness and the residue crystallized in methyl-tert-butyl ether, filtered and the precipitate washed with methyl-tert-butyl ether and dried to give 407 g (74.7%) of 7-bromo-2-chloro-quinoxaline. Filtrate was evaporated and re-crystallized in methyl-tert-butyl ether to provide a second fraction of 72 g (13.2%) of 7-bromo-2-chloro-quinoxaline.

b) Under N$_2$, 7-bromo-2-chloro-quinoxaline (20 g; 82.1 mmol), 1-methyl-4-(4,4,5,5-tetramethyl-1,3,2-dioxaborolan-2-yl)-1H-pyrazole (17.1 g; 82.1 mmol), 2M sodium carbonate aqueous solution (41.1 mL; 82.1 mmol) in ethylene glycol dimethyl ether (200 mL) were degassed by bubbling nitrogen through for 15 minutes. Tetrakis(triphenylphosphine)palladium (0) (0.95 g; 0.82 mmol) was added and heated at reflux for 15 hours. The reaction mixture was poured into water and extracted with EtOAc. The organic layer was dried over MgSO$_4$, filtered and evaporated to dryness to give 29.9 g. The crude compound was purified by chromatography over silica gel (Irregular SiOH, 20-45 µm, 1000 g MATREX; mobile phase 0.1% NH$_4$OH, 98% DCM, 2% CH$_3$OH). The pure fractions were collected and concentrated till dryness to give 19.5 g (82%) of 7-Bromo-2-(1-methyl-1H-pyrazol-4-yl)-quinoxaline. MP=172° C.

7-Bromo-2-(1-methyl-1H-pyrazol-4-yl)-quinoxaline was alternatively also prepared using the following procedure:

7-bromo-2-chloro-quinoxaline (502 g; 2.06 mol), 1-methyl-4-(4,4,5,5-tetramethyl-1,3,2-dioxaborolan-2-yl)-1H-pyrazole (450.42 g; 2.16 mol), triphenylphosphine (10.82 g; 0.041 mol) and palladium(II)acetate were added to a mixture of sodium carbonate (240.37 g; 2.267 mol), 1,2-dimethoxyethane (5.48 L) and water (1.13 L). The reaction mixture was stirred at reflux for 20 hours, then 1-methyl-4-(4,4,5,5-tetramethyl-1,3,2-dioxaborolan-2-yl)-1H-pyrazole (42.9 g; 0.206 mol) was added and the reaction mixture refluxed until complete conversion (4 hours). The reaction mixture was poured out in water, stirred for 2 hours at room temperature, filtered and the precipitate was washed with water. The precipitate was then triturated in methanol and filtered. The precipitate was washed with methanol and dried to give 532.2 g (89%) of 7-Bromo-2-(1-methyl-1H-pyrazol-4-yl)-quinoxaline (off-white powder).

c) 7-Bromo-2-(1-methyl-1H-pyrazol-4-yl)-quinoxaline (2.5 g; 8.0 mmol), bis(pinacolato)diboron (2.4 g; 9.6 mmol), 1,1'-bis(diphenylphosphino)ferrocenedichloropalladium(II) (291 mg; 0.4 mmol) and potassium carbonate (2.3 g; 23.9 mmol) in dioxane anhydrous (30 mL) were heated at 100° C. for 90 minutes. The mixture was poured into water and 10% aqueous NH$_4$Cl solution, then ethyl acetate was added. The organic layer was decanted, dried (MgSO$_4$), filtered and evaporated. The crude product was taken up in pentane and the precipitate was filtered, yielding 1.6 g (60%) of intermediate 3. (cas number 1083325-88-5)

Example A3

Preparation of Intermediate 4

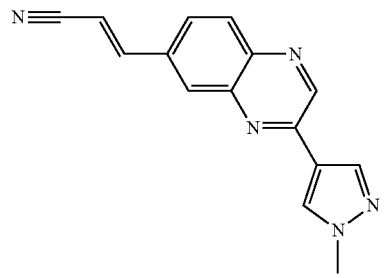 [SMILES: Cn1cc(-c2cnc3ccc(/C=C/C#N)cc3n2)cn1]

The experiment was done 9 times on the same quantity of 7-Bromo-2-(1-methyl-1H-pyrazol-4-yl)-quinoxaline (1 g, 3.5 mmol) and all crude reaction mixtures gathered for purification:

7-Bromo-2-(1-methyl-1H-pyrazol-4-yl)-quinoxaline (1 g; 3.5 mmol), acrylonitrile (0.69 mL; 10.4 mmol), palladium(II) acetate (47% Pd) (39 mg; 0.17 mmol), tri-o-tolylphosphine (105 mg; 0.35 mmol) and TEA (1.4 mL; 10.4 mmol) in ACN (3 mL) were stirred at reflux for 48 hours. The 9 experiments were combined for the work up. After cooling down to room temperature, the reaction mixture was filtered through a pad of Celite®. Celite® was washed with EtOAc. The filtrate was evaporated. The residue was purified by chromatography over silica gel [(Irregular SiOH, 15-40 µm, 300 g), mobile phase (99% DCM, 1% MeOH)]. The pure fractions were collected and the solvent was evaporated, yielding 2.6 g (32%) of intermediate 4, m.p.=179° C.

Example A4

Preparation of Intermediate 5

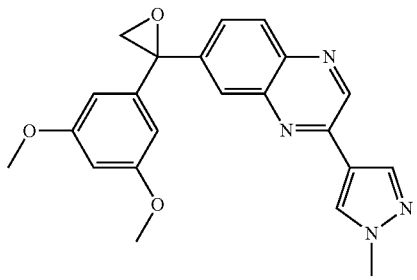 [SMILES: COc1cc(OC)cc(C2(c3ccc4ncc(-c5cnn(C)c5)nc4c3)CO2)c1]

Potassium tert-butoxide (1.2 g; 10.4 mmol) was added portionwise to a solution of trimethylsulphoxonium iodide (2.3 g; 10.4 mmol) in dimethoxymethane (80 mL) at room temperature. The mixture was stirred at room temperature for 1 hour and the solution was added dropwise to a solution of compound 2(2.6 g; 6.9 mmol) in DMSO (30 mL) at 5° C. under $N_2$ flow. The reaction mixture was stirred at 5° C. for 1 hour, then at room temperature for 48 hours. The reaction mixture was poured out into ice water and EtOAc was added. The organic layer was separated, washed with brine, dried ($MgSO_4$), filtered and the solvent was evaporated. The residue was purified by chromatography over silica gel [(Irregular SiOH, 20-45 µm, 450 g), mobile phase (Gradient from 60% DCM, 40% EtOAc to 30% DCM, 70% EtOAc)]. The desired product fractions were collected and the solvent was evaporated, yielding 700 mg (26%) of intermediate 5.

Example A5

Preparation of Intermediate 6

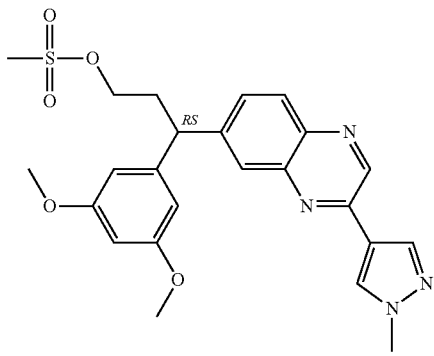 [SMILES: COc1cc(OC)cc(C(CCOS(C)(=O)=O)c2ccc3ncc(-c4cnn(C)c4)nc3c2)c1]

Methanesulfonylchloride (976 µL; 12.6 mmol) was added to a solution of compound 22 (1.7 g; 4.2 mmol) and TEA (2.34 mL; 16.8 mmol) in ACN (5 mL) at 5° C. under $N_2$. The reaction mixture was stirred for 1 hour at room temperature. Water was added and the mixture was extracted with DCM. The organic layer was dried ($MgSO_4$), filtered and evaporated until dryness, yielding 2 g (98%) of intermediate 6, which was used without any further purification for the next step.

Example A6 a) Preparation of Intermediate 7

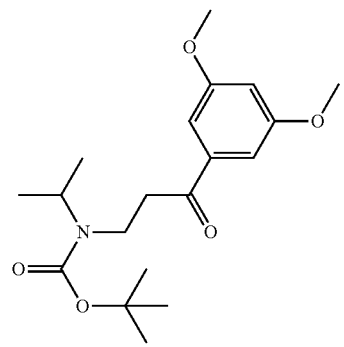 [SMILES: COc1cc(OC)cc(C(=O)CCN(C(=O)OC(C)(C)C)C(C)C)c1]

Preparation of HCl salt of isopropylamine: hydrochloric acid 5 to 6N solution in 2-propanol (7.2 mL; 39.5 mmol) was carefully added to a solution of isopropylamine (2.7 mL; 31.7 mmol) in $Et_2O$ (20 mL) at 0-5° C. The reaction mixture was stirred for 15 minutes, then evaporated until dryness, yielding HCl salt of isopropylamine. 3,5-Dimethoxyacetophenone (5.7 g; 31.7 mmol), HCl salt of isopropylamine and paraformaldehyde (2.37 g; 79 mmol) in EtOH (8.8 mL) were stirred at 140° C. for 12 minutes in a sealed tube. After cooling down to room temperature, this solution was added to a solution of di-tert-butylcarbonate (13.8 g; 63.3 mmol) and TEA (13.2 mL; 95 mmol) in DCM (100 mL) at room temperature. The reaction mixture was stirred for 24 hours at room temperature. The reaction mixture was washed successively with HCl 1N, 10% $K_2CO_3$ aqueous solution and water. The organic layer was dried ($MgSO_4$), filtered and evaporated. The residue (10.1 g) was purified by chromatography over silica gel [(Irregular SiOH, 20-45 µm, 450 g), mobile phase (80% HEPTANE, 20% EtOAc)] yielding 4.8 g (43%) of intermediate 7.

b) Preparation of Intermediate 8

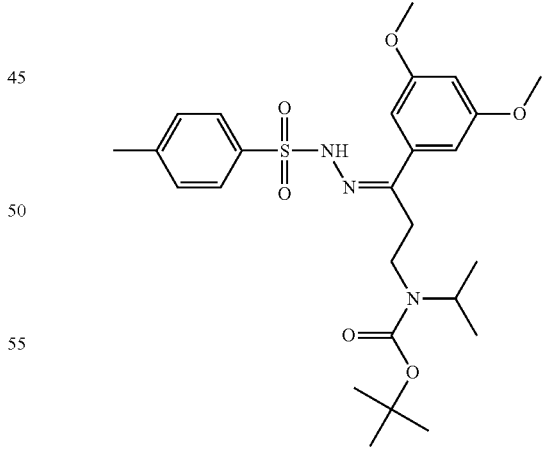

Intermediate 7 (4.2 g; 12 mmol) and p-toluenesulfonhydrazide (2.34 g; 12.6 mmol) in EtOH (30 mL) were stirred at reflux for 4 hours. The solvent was evaporated and the residue was taken up into $Et_2O$, stirred for 15 minutes and the precipitate was filtered off and dried yielding 2.6 g (42%) of intermediate 8. The filtrate was evaporated and the residue (4.2 g) was purified by chromatography over silica gel [(Irregular SiOH, 20-45 μm, 450 g); mobile phase (70% HEPTANE, 30% EtOAc)] to give another batch of 1.6 g (26%) of intermediate 8.

c) Preparation of Intermediates 9 and 10

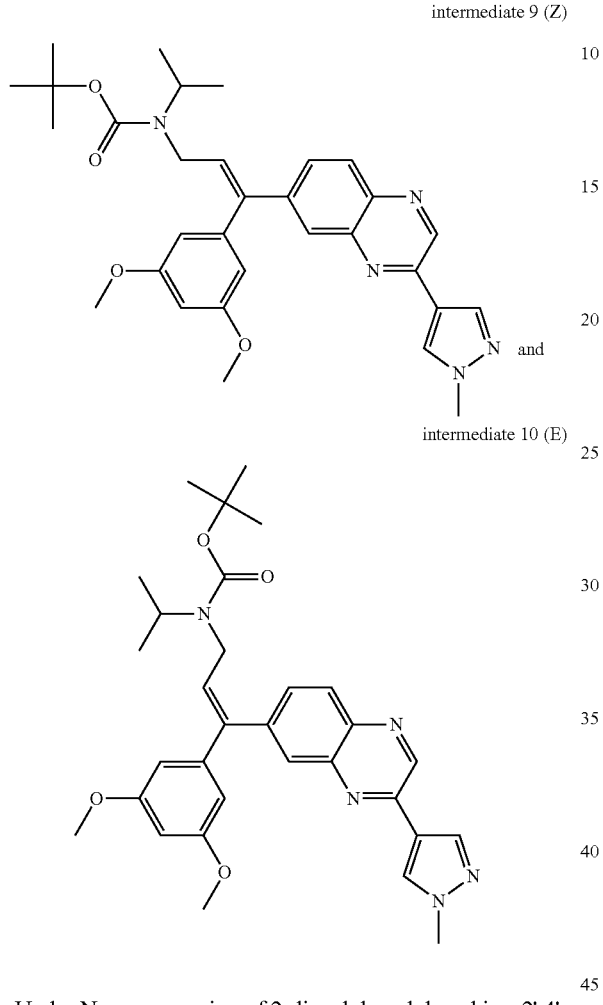

Under N₂, a suspension of 2-dicyclohexylphosphino-2',4',6'-tri-1-propyl-1,1'-biphenyl (58.7 mg; 0.12 mmol), tris(dibenzylideneacetone)dipalladium (56 mg; 0.06 mmol), lithium tert-butoxide (0.71 g; 7.4 mmol) and intermediate 8 (1.6 g, 3 mmol) in 1,4-dioxane (20 mL) were stirred at room temperature for 1-2 minutes, then bromo-2-(1-methyl-1H-pyrazol-4-yl)-quinoxaline (0.89 g; 3.1 mmol) was added. The reaction mixture was stirred at 110° C. for 12 hours. This experiment was combined with 2 identical experiments (made on 556 mg of bromo-2-(1-methyl-1H-pyrazol-4-yl)-quinoxaline and on 150 mg of bromo-2-(1-methyl-1H-pyrazol-4-yl)-quinoxaline) for the work up. Water and EtOAc were added. The organic layer was decanted, dried (MgSO₄), filtered and evaporated. The residue was purified by chromatography over silica gel [(Irregular SiOH, 20-45 μm, 450 g), mobile phase (98% DCM, 2% MeOH)]. The desired product fractions were collected and the solvent was evaporated to give 1.4 g (impure fraction) of a mixture of intermediate 9 and 10 and 638 mg (21%) of intermediate 10. The impure fraction (1.4 g) was purified by chiral SFC [(CHIRALPAK AD-H, 5 μm, 250×20 mm, mobile phase (75% CO₂, 25% EtOH)]. The pure fractions were collected and the solvent was evaporated to give 750 mg (25%) of intermediate 9 and 70 mg (2.3%) of intermediate 10.

Example A7

Preparation of Intermediates 11 and 12

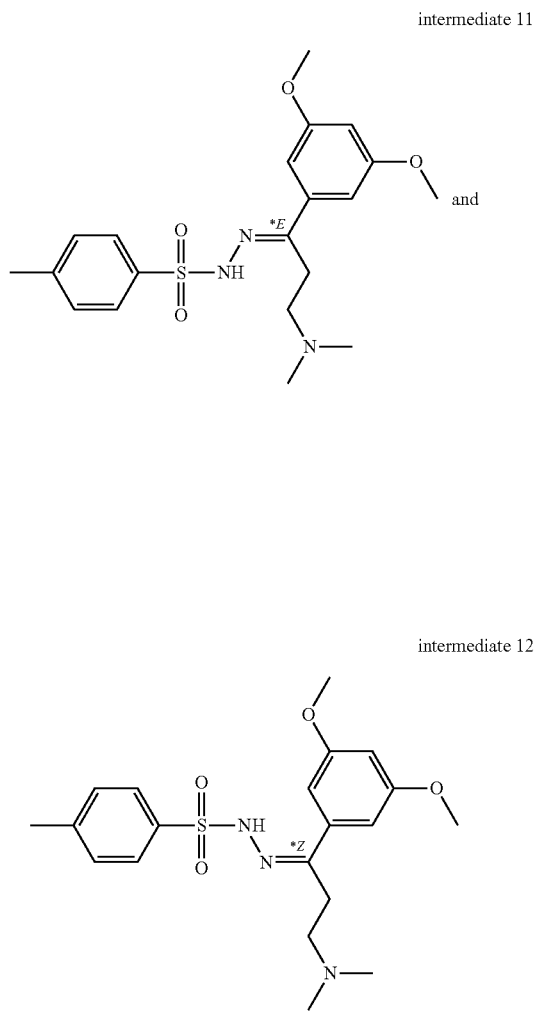

3-Dimethylaminopropiophenone hydrochloride (1.6 g; 5.8 mmol) was added to a solution of p-toluenesulfonhydrazide (1.1 g; 5.8 mmol) in hydrochloric acid 5 to 6N solution in 2-propanol (7.2 mL), Et₂O (4.2 mL) and distilled water (2.6 mL) at room temperature. The reaction mixture was stirred overnight. Extra p-toluenesulfonhydrazide (1.1 g; 5.8 mmol) was added and the reaction mixture was stirred for 48 hours. The mixture was basified with NaOH 1N and extracted with DCM. The organic layer was decanted, washed with brine, dried (MgSO₄), filtered and evaporated. The residue was purified by chromatography over silica gel [(Irregular SiOH, 15-40 μm, 300 g), mobile phase (Gradient from 0.1% NH₄OH, 97% DCM, 3% MeOH to 0.2% NH₄OH, 96% DCM, 4% MeOH)]. The desired fractions were collected and the solvent was evaporated, yielding 1.5 g (64%) of intermediate 11 and 340 mg (14.5%) of intermediate 12.

* means relative stereochemistry

Example A8

Preparation of Intermediate 13

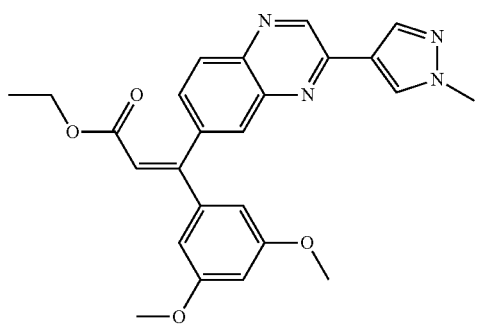 [SMILES: CCOC(=O)/C=C(/c1cc(OC)cc(OC)c1)c1ccc2ncc(-c3cnn(C)c3)nc2c1]

The experiment was performed twice on (3.1 g; 13.1 mmol) of (2E)-3-(3,5-dimethoxyphenyl)-2-propenoic acid ethyl ester:

7-Bromo-2-(1-methyl-1H-pyrazol-4-yl)-quinoxaline (4.7 g; 16.4 mmol), (2E)-3-(3,5-dimethoxyphenyl)-2-propenoic acid ethyl ester (3.1 g; 13.1 mmol), palladium(II) acetate (47% Pd) (147 mg; 0.66 mmol), tri-o-tolylphosphine (400 mg; 1.3 mmol) and TEA (5.5 ml; 39.4 mmol) in ACN (9 mL) were stirred at reflux for 36 hours.

The 2 experiments were combined for the work up.

After cooling down to room temperature, water was added. The reaction mixture was filtered through a pad of Celite®. Celite® was washed with DCM. The organic layer was separated, dried (MgSO$_4$), filtered and evaporated. The residue was purified by chromatography over silica gel [(Irregular SiOH, 15-40 μm, 400 g), mobile phase (70% EtOAc, 30% HEPTANE)]. The desired fractions were collected and the solvent was evaporated to give 16.4 g of a mixture. This fraction was purified again by chromatography over silica gel [(Irregular SiOH, 20-45 μm, 450 g), mobile phase (30% HEPTANE, 70% EtOAc)], yielding 5 g (43%) of intermediate 13, m.p.=139° C.

Example A9

Preparation of Intermediate 14

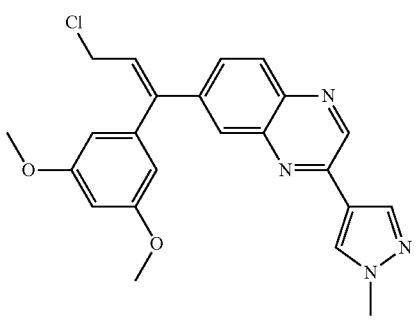 [SMILES: COc1cc(OC)cc(/C(=C\CCl)c2ccc3ncc(-c4cnn(C)c4)nc3c2)c1]

Methanesulfonyl chloride (770 μL; 9.9 mmol) was added dropwise to a solution of compound 11 (2 g; 5 mmol), TEA (1.7 mL; 12.4 mmol) in DCM (50 mL) at 5° C. under N$_2$ flow. The reaction mixture was stirred at 5° C. for 30 minutes, then for 1 hour at room temperature. TEA (1.7 mL; 12.4 mmol.) and methanesulfonyl chloride (770 μL; 9.9 mmol) were added to the mixture at 5° C. The mixture was stirred at room temperature for 4 hours. The reaction mixture was poured out into ice water and CH$_2$Cl$_2$ was added. The organic layer was separated, dried (MgSO$_4$), filtered and the solvent was evaporated. The residue (2.96 g) was purified by chromatography over silica gel [(Irregular SiOH, 15-40 μm, 90 g), mobile phase (gradient from 95/5 DCM/MeOH to 90/10 DCM/MeOH], yielding 820 mg of intermediate 14 (39%).

Example A10 a) Preparation of Intermediate 15

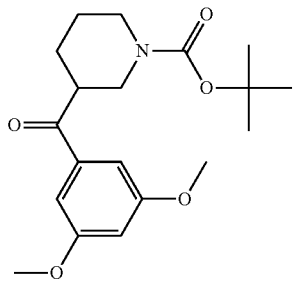 [SMILES: COc1cc(OC)cc(C(=O)C2CCCN(C(=O)OC(C)(C)C)C2)c1]

n-Butyllithium 1.6M in hexane (17 mL; 27 mmol) was added dropwise to a stirred solution of 1-bromo-3,5-dimethoxybenzene (5.9 g; 27 mmol) in THF (50 mL) at −78° C. under nitrogen. The reaction mixture was stirred for 20 minutes then allowed to reach 0° C. then cooled down to −78° C. This solution was added to a solution of 3-[(methoxymethylamino)carbonyl]-1-piperidinecarboxylic acid 1,1-dimethylethyl ester (6.7 g; 24.6 mmol) in Et$_2$O (35 mL) at −78° C. The reaction mixture was allowed to reach room temperature and stirred for 4 hours. Water was added and the reaction mixture was extracted twice with EtOAc, dried (MgSO$_4$), filtered and evaporated. The residue was purified by chromatography over silica gel [(Irregular SiOH, 20-45 μm, 450 g MATREX), mobile phase (85% HEPTANE, 15% EtOAc)] to give 330 mg (3.8%) of intermediate 15.

b) Preparation of Intermediate 16

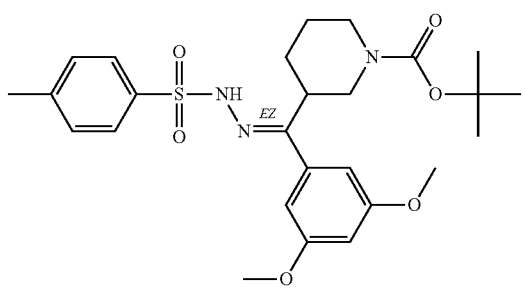 [SMILES: COc1cc(OC)cc(/C(=N/NS(=O)(=O)c2ccc(C)cc2)C2CCCN(C(=O)OC(C)(C)C)C2)c1]

Intermediate 15 (0.62 g; 1.77 mmol) and p-toluenesulfonhydrazide (0.35 g; 1.86 mmol) in ethanol (6 mL) were stirred successively at reflux for 4 hours, at 60° C. for 6 hoursand at room temperature overnight. The solvent was evaporated, yielding 900 mg (98%) of intermediate 16.

c) Preparation of intermediate 17

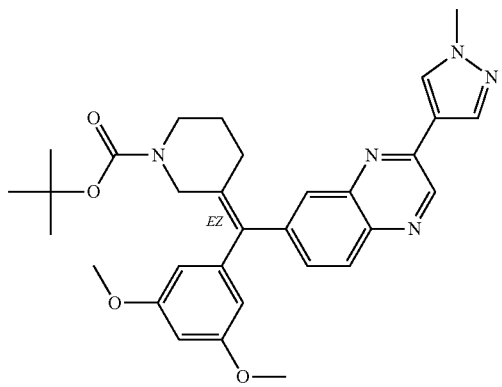 [SMILES: COc1cc(OC)cc(/C(=C2/CCCN(C(=O)OC(C)(C)C)C2)c2ccc3ncc(-c4cnn(C)c4)nc3c2)c1]

Under N₂, a suspension of 2-dicyclohexylphosphino-2',4',6'-tri-1-propyl-1,1'-biphenyl (58.7 mg; 0.12 mmol), tris(dibenzylideneacetone)dipalladium (56 mg; 0.06 mmol), lithium tert-butoxide (0.71 g; 7.4 mmol) and intermediate 16 (1.6 g; 3.08 mmol) in 1,4-dioxane (20 mL) was stirred at room temperature for less than 2 minutes then 7-bromo-2-(1-methyl-1H-pyrazol-4-yl)-quinoxaline (0.89 g; 3.1 mmol) was added. The reaction mixture was stirred at 110° C. for 12 hours. Water and EtOAc were added. The organic layer was decanted, dried (MgSO₄), filtered and evaporated. The residue was purified by chromatography over silica gel [(Irregular SiOH, 20-45 μm, 450 g), mobile phase (0.1% NH4OH, 98% DCM, 2% MeOH)] to give 395 mg (42%) of intermediate 17.

d) Preparation of Intermediate 18

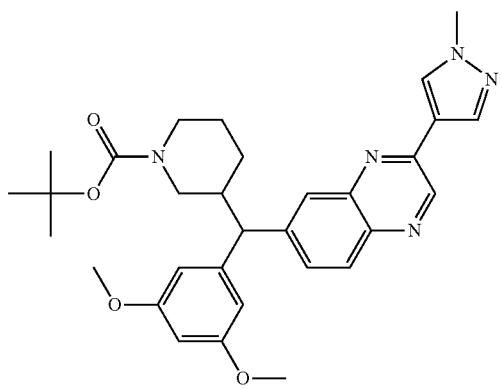 [SMILES: COc1cc(OC)cc(C(c2ccc3ncc(-c4cnn(C)c4)nc3c2)C2CCCN(C(=O)OC(C)(C)C)C2)c1]

Intermediate 17 (395 mg; 0.73 mmol) was hydrogenated at room temperature in MeOH (4 mL) with Pd (10% on dried Carbon) (50 mg) as a catalyst at atmospheric pressure for 6 hours. The catalyst was filtered off on a pad of Celite®. Celite® was washed with CH₂Cl₂/MeOH. The filtrate was evaporated to give 375 mg (95%) of intermediate 18.

B. Preparation of the Compounds

Example B1

Preparation of Compound 1

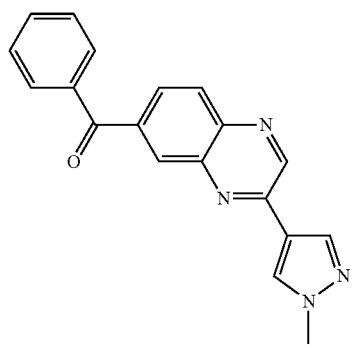 [SMILES: Cn1cc(-c2cnc3ccc(C(=O)c4ccccc4)cc3n2)cn1]

Intermediate 2 (1.3 g; 4.8 mmol), 1-methyl-4-(4,4,5,5-tetramethyl-1,3,2-dioxaborolan-2-yl)-1H-pyrazole (1 g; 4.8 mmol), 2M aqueous sodium carbonate solution (2.4 mL; 4.8 mmol) in ethylene glycol dimethyl ether (20 mL) were degassed with N₂ for 15 minutes. Pd(PPh₃)₄ (0.55 g; 0.48 mmol) was added and the reaction mixture was refluxed overnight. The mixture was poured into H₂O and EtOAc. The organic layer was washed with brine, dried (MgSO₄), filtered and the solvent was evaporated until dryness. The residue (2.2 g) was purified by chiral SFC [(CHIRALPAK AD-H, 5 μm, 250×20 mm), mobile phase (40% CO₂, 60% EtOH)], yielding: 800 mg of compound 1 (53%).

Example B2

Preparation of compound 2

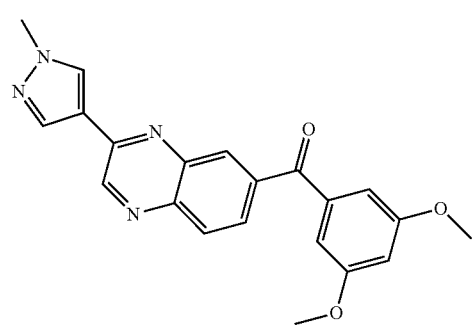 [SMILES: COc1cc(OC)cc(C(=O)c2ccc3ncc(-c4cnn(C)c4)nc3c2)c1]

To a mixture of intermediate 3 (3 g; 8.9 mmol) in THF (100 mL) were added 3,5-dimethoxybenzoyl chloride (3.6 g; 18 mmol), 2M aqueous sodium carbonate solution (70 mL; 140 mmol), dichlorobis(triphenylphosphine) palladium (II) (313 mg; 0.45 mmol) at room temperature under N₂. The mixture was stirred at 50° C. for 2 hours, filtered through a pad of Celite®, washed with DCM and water. The organic layer was decanted and dried (MgSO₄), filtered and evaporated. The residue was purified by chromatography over silica gel [(Irregular SiOH, 15-40 µm, 90 g), mobile phase (0.1% NH₄OH, 97% DCM, 3% MeOH)], yielding two fractions 120 mg and 60 mg of compound 2.

Example B3

Preparation of Compounds 3 and 4

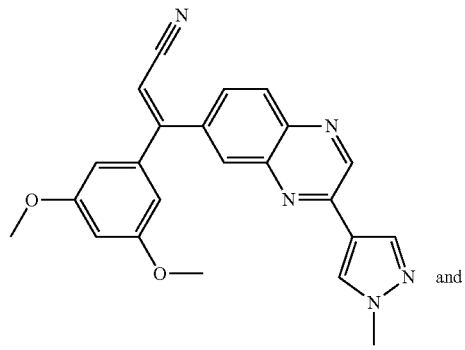
compound 3 and

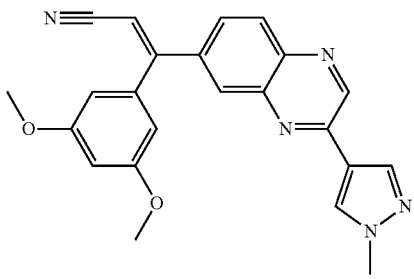
compound 4

A mixture of 7-bromo-2-(1-methyl-1H-pyrazol-4-yl)-quinoxaline (1 g; 3.45 mmol), 3-(3,5-dimethoxyphenyl)-2-propenenitrile (654 mg; 3.5 mmol), palladium (II) acetate (47% Pd) (39 mg; 0.17 mmol), potassium carbonate (1.24 g; 12.7 mmol) and tetrabutylammonium bromide (1.8 g; 5.6 mmol) in N,N-dimethylformamide (15 mL) in a sealed tube was heated at 140° C. using one single mode microwave (Biotage Initiator EXP 60) with a power output ranging from 0 to 400 W for 40 minutes. After cooling down to room temperature, water was added. The mixture was filtered through a pad of Celite®. Celite® was washed with EtOAc. The organic layer was decanted, washed with brine, dried (MgSO₄), filtered and evaporated. The residue was purified by chromatography over silica gel [(Irregular SiOH, 15-40 µm, 90 g), mobile phase (gradient from 0% NH₄OH, 100% DCM, 0% MeOH to 0.1% NH₄OH, 95% DCM, 5% MeOH)]. The pure fractions were collected and evaporated until dryness. The residue (245 mg) was purified by Reverse phase chromatography [(X-Bridge-C18, 5 µm, 30*150 mm), mobile phase (gradient from 60% NH₄HCO₃ (0.5% solution), 40% ACN to 0% NH₄HCO₃ (0.5% solution), 100% ACN)], yielding 20 mg (1.5%) compound 3 and 70 mg of residue which was purified by Chiral SFC [(CHIRALPAK AD-H, 5 µm, 250×20 mm), mobile phase (0.3% isopropylamine, 60% CO₂, 20% EtOH, 20% iPrOH)], yielding 33 mg (2.4%) of compound 4.

Example B4

Alternative Preparation of B3

Preparation of Compound 4

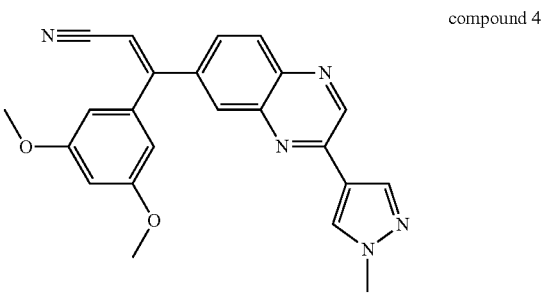 [SMILES: COc1cc(OC)cc(/C(=C\C#N)c2ccc3ncc(-c4cnn(C)c4)nc3c2)c1]
compound 4

The experiment was done 9 times on same scale of 7-bromo-2-(1-methyl-1H-pyrazol-4-yl)-quinoxaline (1.88 g; 6.5 mmol):

A mixture of 7-bromo-2-(1-methyl-1H-pyrazol-4-yl)-quinoxaline (1.88 g; 6.5 mmol), 3-(3,5-dimethoxyphenyl)-2-propenenitrile (1 g; 5.5 mmol), palladium (II) acetate (47% Pd) (73 mg; 0.33 mmol), TEA (2.7 mL; 19.5 mmol) and tri-o-tolylphosphine (0.2 g; 0.65 mmol) in acetonitrile (3.9 mL) were stirred at reflux overnight. After cooling down to room, the 9 experiments were combined for the work up. Water and DCM were added. The organic layer was separated, dried over MgSO₄, filtered and evaporated to give 24.3 g of crude product.

The residue was purified by chromatography on silica gel [(Irregular SiOH, 20-45 µm, 1000 g), mobile phase (gradient from 20% heptane, 80% AcOEt to 0% heptane, 100% AcOEt)], affording 5 g (21%) of compound 4.

Example B5

Alternative Preparation of B2

Preparation of Compound 2

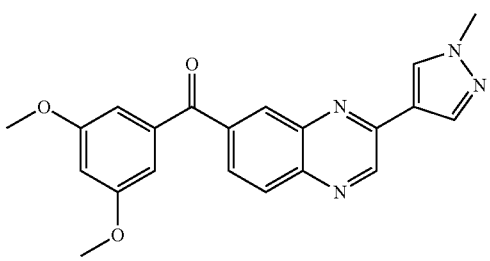 [SMILES: COc1cc(OC)cc(C(=O)c2ccc3ncc(-c4cnn(C)c4)nc3c2)c1]

7-Bromo-2-(1-methyl-1H-pyrazol-4-yl)-quinoxaline (8 g; 28 mmol), 3,5-dimethoxybenzeneboronic acid (9.4 g; 52 mmol), tricyclohexylphosphine (145 mg; 0.52 mmol), palladium (II) acetate (47% Pd) (39 mg; 0.17 mmol), TEA (9.6 mL; 69 mmol) in toluene (50 mL) under 5 bars of CO (gas) at 100° C. for 66 hours. This experiment was combined to a same experiment made on 2 g of 7-bromo-2-(1-methyl-1H- pyrazol-4-yl)-quinoxaline. The mixture was diluted with DCM and water. The organic layer was dried (MgSO$_4$), filtered and evaporated. The residue was purified by chromatography over silica gel on [(Irregular SiOH 20-45 µm 1000 g), mobile phase (20% HEPTANE, 80% EtOAc)], yielding 2.65 g (20%) of compound 2, m.p.=162° C.

Example B6

Preparation of Compounds 5 and 6

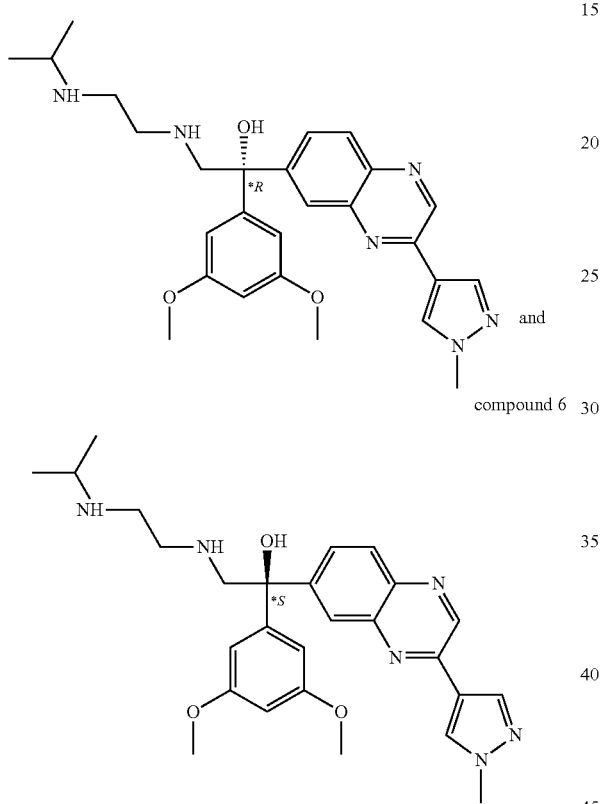

A mixture of intermediate 5 (700 mg; 1.8 mmol) and N-isopropylethylenediamine (98%) (4.55 mL; 36. mmol) in ethanol (7 mL) was heated at reflux overnight in a sealed tube. Ethanol was evaporated. The residue (1.5 g) was first purified by chromatography over silica gel [(Irregular SiOH, 20-45 µm, 450 g), mobile phase (0.8% NH$_4$OH, 92% DCM, 8% MeOH)]. The expected compound fractions were collected and the solvent was evaporated. The residue (467 mg) was purified by achiral SFC [(AMINO, 6 µm, 150×21.2 mm), mobile phase (0.3% ISOPROPYLAMINE, 60% CO$_2$, 40% MeOH)]. The expected compound fractions were collected and the solvent was evaporated. The residue was then purified by chiral SFC [(CHIRALPAK AD-H, 5 µm, 250×20 mm), mobile phase (0.3% ISOPROPYLAMINE, 65% CO$_{02}$, 35% EtOH)]. The 2 expected compounds fractions were combined and the solvent was evaporated to give 125 mg of one enantiomer (first fraction), and 130 mg of the other enantiomer (second fraction).

The first fraction (125 mg-14%) was converted into the HCl (5 eq.) salt in MeOH. Et$_2$O was added. The precipitate was filtered off and dried to give 138 mg of a brown solid product. This product was basified with a mixture of ice water and NH$_4$OH. DCM was added and the organic layer was separated, dried (MgSO$_4$) and the solvent was evaporated, yielding 94 mg of residue. This residue was purified by chromatography over silica gel [(Stability Silica, 5 µm, 150×30.0 mm), mobile phase (Gradient from 0.2% NH$_4$OH, 98% DCM, 2% MeOH to 1.1% NH$_4$OH, 89% DCM, 11% MeOH)], yielding 57 mg (6.5%) of compound 5.

The second fraction (130 mg-15%) was converted into the HCl (5 eq.) salt in MeOH. Et$_2$O was added. The precipitate was filtered and dried to give 92 mg of a brown solid. This product was basified with a mixture of ice water and NH$_4$OH. DCM was added and the organic layer was separated, dried (MgSO$_4$) and the solvent was evaporated, yielding 94 mg of residue. This residue was purified by chromatography over silica gel [(Stability Silica, 5 µm, 150×30.0 mm), mobile phase (Gradient from 0.2% NH$_4$OH, 98% DCM, 2% MeOH to 1.2% NH$_4$OH, 88% DCM, 12% MeOH)], yielding 21 mg (2.4%) of compound 6.

* means relative stereochemistry

Example B7

Preparation of compound 7

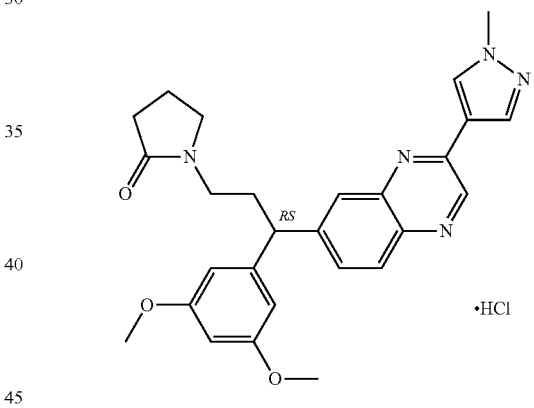

Sodium hydride (60% in oil) (60 mg; 1.5 mmol) was added portionwise to a solution of 2-pyrrolidinone (0.12 mL; 1.5 mmol) in N,N-dimethylformamide (5 mL) at 5° C. under N$_2$ flow. The reaction mixture was stirred at 5° C. for 1 hour, then a solution of intermediate 6 (0.5 mmol; 250 mg) in dry DMF (3 mL) was added dropwise at 5° C. The reaction mixture was stirred at 5° C. for 1 hour, then overnight at room temperature. The reaction mixture was poured out into ice water and EtOAc was added. The organic layer was separated, washed with brine, dried (MgSO$_4$), filtered and the solvent was evaporated. The residue was purified by chromatography over silica gel [(Spherical SiOH, 10 µm, 60 g), mobile phase (0.1% NH$_4$OH, 97% DCM, 3% MeOH)] to give 63 mg of residue. This residue was purified by achiral SFC [(AMINO, 6 µm, 150×21.2 mm); mobile phase (0.3% ISOPROPYLAMINE, 20% MeOH, 80% CO$_2$)]. The residue (43 mg, 8.7%) was dissolved in MeOH and converted into the hydrochloric acid salt with HCl/2-propanol. Et$_2$O was added, then the solvent was evaporated to dryness, yielding 32 mg (6.2%) of compound 7.

Example B8 a) Preparation of Compound 8

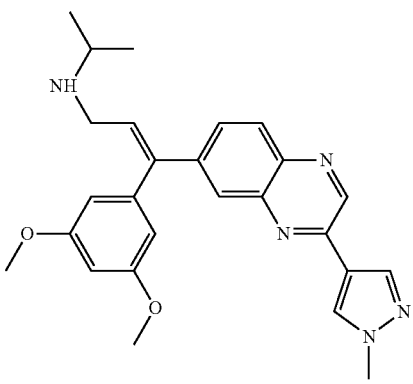
(Z)

3M HCl (8 mL) was added to a solution of intermediate 9 (0.75 g; 1.38 mmol) in MeOH (20 mL) at room temperature. The reaction mixture was heated at 60° C. for 6 hours. After cooling down to room temperature, the crude mixture was made basic with 10% $K_2CO_3$ aqueous solution and extracted twice with DCM. The combined organic layers were dried ($MgSO_4$), filtered and evaporated. The residue (0.58 g) was purified by chromatography over silica gel [(Spherical SiOH, 10 μm, 60 g), mobile phase (0.5% $NH_4OH$, 95% DCM, 5% MeOH)] to give 0.55 g of residue which was crystallized from ACN to give 373 mg (61%) of compound 8.

m.p.=164° C.

b) Preparation of compound 9

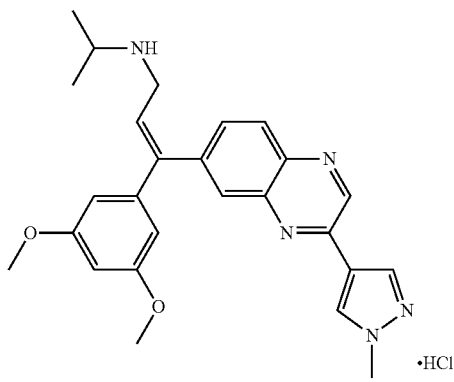
(E)

3M HCl (8 mL) was added to a solution of intermediate 10 (0.64 g; 1.17 mmol) in MeOH (20 mL) at room temperature. The reaction mixture was heated at 60° C. for 6 hours. After cooling down to room temperature, the crude mixture was made basic with 10% $K_2CO_3$ aqueous solution and extracted twice with DCM. The combined organic layers were dried ($MgSO_4$), filtered and dried. This fraction (0.45 g) was purified by chromatography over silica gel [(Spherical SiOH, 10 μm, 60 g), mobile phase (0.5% $NH_4OH$, 95% DCM, 5% MeOH)] to give 240 mg (46%) of product fraction. The hydrochloric salt of this fraction was prepared in MeOH and crystallized from MeOH/$Et_2O$, yielding 193 mg (32%) of compound 9.

Example B9

Preparation of compound 10 (Z)

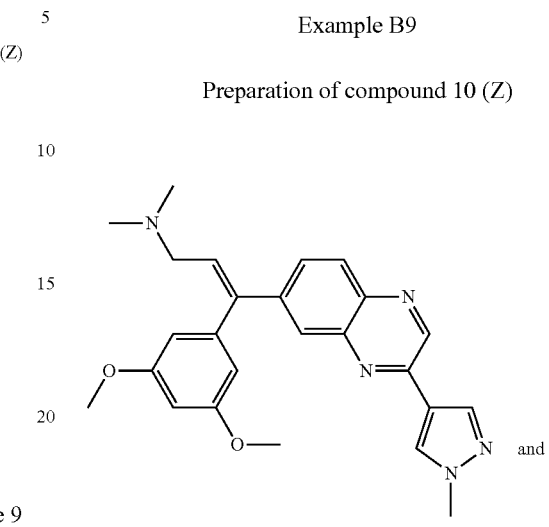
and

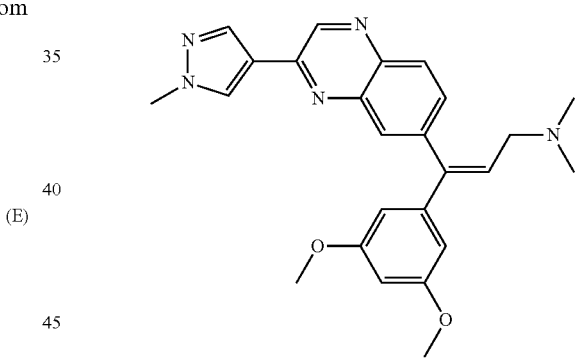
compound 34 (E)

In a sealed tube, under $N_2$, a suspension of X-Phos (67 mg; 0.142 mmol), $Pd_2(dba)_3$ (16.3 mg; 0.018 mmol), lithium tert-butoxide (1 g; 10.7 mmol) and intermediate 12 (1.44 g; 3.6 mmol) in 1,4-dioxane (28 mL) was stirred at room temperature for less than 2 minutes. Then 7-bromo-2-(1-methyl-1H-pyrazol-4-yl)-quinoxaline (1 g; 3.6 mmol) was added. The reaction mixture was stirred at 110° C. for 12 hours. The mixture was diluted with water and EtOAc. The organic layer was dried ($MgSO_4$), filtered and evaporated. The residue was purified by chromatography over silica gel [(Irregular SiOH, 20-45 μm, 450 g), mobile phase (Gradient from 0.4% $NH_4OH$, 98% DCM, 2% MeOH to 0.7% $NH_4OH$, 94% DCM, 6% MeOH)]. The product fraction (0.75 g) was purified by achiral SFC [(AMINO, 6 μm, 150×21.2 mm), mobile phase (85% $CO_2$, 15% EtOH)]. The desired fractions were collected and the solvent was evaporated to give 270 mg of first fraction and 180 mg of the second fraction.

The first fraction (270 mg) was crystallized from $Et_2O$ and ACN to give 170 mg (11%) of compound 10 (Z). m.p. 164° C.

The second fraction (180 mg) was crystallized from Et₂O and ACN to give 115 mg (7.5%) of compound 34 (E). m.p. 177° C.

Example B10

Preparation of Compound 11

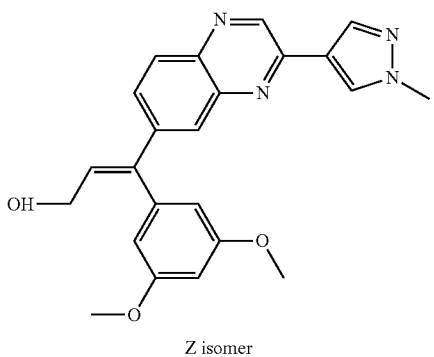 [SMILES: COc1cc(OC)cc(/C(=C\CO)c2ccc3ncc(-c4cnn(C)c4)nc3c2)c1]

Z isomer

Diisobutylaluminium hydride (solution 20% in toluene) (6.75 mL; 1 mmol) was added dropwise to a solution of intermediate 13 (4 g; 9 mmol) in dry THF (48 mL) at 0° C. under N₂. The reaction mixture was stirred at room temperature for 2 hours.

Diisobutylaluminium hydride (6.75 mL; 8.1 mmol) was added dropwise to the mixture at 0° C. The reaction mixture was stirred at room temperature for 2 hours.

Diisobutylaluminium hydride (6.75 mL; 8.1 mmol) was added dropwise to the mixture at 0° C. The reaction mixture was stirred at room temperature overnight. The mixture was cooled to −10° C. and MeOH (20 mL) was added dropwise. Then, a solution of 10% NH₄Cl (25 mL) was added dropwise. The mixture was diluted with EtOAc. The mixture was extracted with EtOAc. The organic layer was dried (MgSO₄), filtered and the solvent was evaporated. The residue (3.83 g) was purified by chromatography over silica gel [(Irregular SiOH, 20-45 μm, 450 g), mobile phase (0.1% NH₄OH, 97% DCM, 3% MeOH)], yielding 2.1 g of compound 11 (58%, yellow solid).

Example B11

Preparation of Compound 12

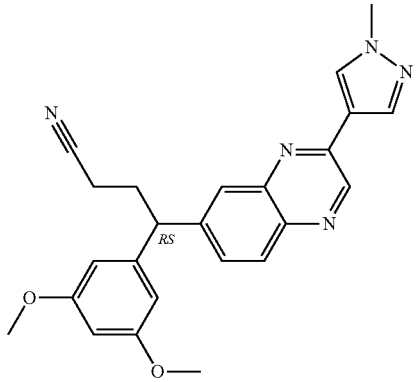 [SMILES: COc1cc(OC)cc(C(CCC#N)c2ccc3ncc(-c4cnn(C)c4)nc3c2)c1]

Potassium cyanide (2.7 g; 41.5 mmol) in DMF (15 mL) was stirred for 20 minutes at room temperature. A solution of intermediate 6 (2 g; 4.1 mmol) in DMF (10 mL) was added to the suspension. The mixture was stirred at room temperature for 18 h. Water was added and the reaction mixture was extracted with EtOAc. The organic layer was washed with brine, dried (MgSO₄), filtered and evaporated. The residue was purified by chromatography over silica gel [(Irregular SiOH, 20-45 μm, 450 g), mobile phase (Gradient from 20% HEPTANE, 80% EtOAc to 10% HEPTANE, 90% EtOAc)], yielding 345 mg (20%) of compound 12.

Example B12

Preparation of Compound 13

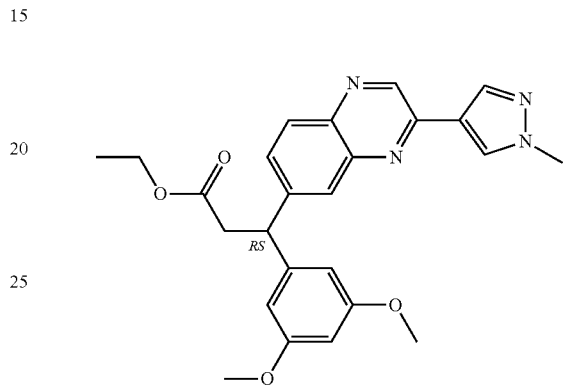

Magnesium (3.1 g; 129 mmol) was added in one portion to a suspension of intermediate 13 (5.2 g; 11.7 mmol) in MeOH (180 mL) and THF (19 mL) at room temperature. The reaction mixture was stirred for 45 minutes. The temperature raised to 35° C. The reaction mixture was cooled down to 10° C. and stirred for 1 hour. Ice and 10% aqueous NH₄Cl solution were added. The reaction mixture was extracted with DCM, dried over MgSO₄, filtered and evaporated.

The residue (5.3 g) was purified by chromatography over silica gel [(Irregular SiOH, 15-40 μm, 90 g), mobile phase (gradient from 0% NH₄OH, 100% DCM, 0% MeOH to 0.1% NH₄OH, 97% DCM, 3% MeOH)]. The pure fractions were collected and evaporated to dryness to give 3.9 g (74%) of compound 13.

Example B13

Preparation of Compound 14

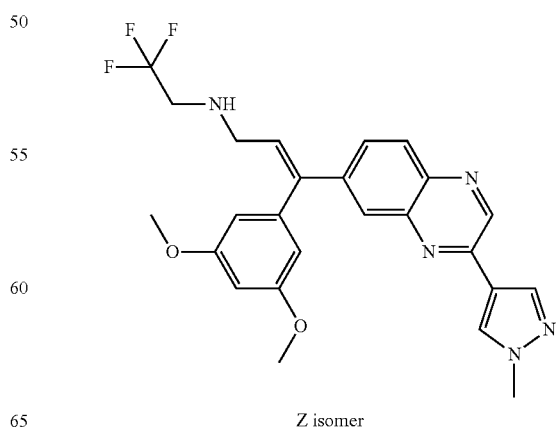

Z isomer 2,2,2-Trifluoroethylamine (0.76 mL; 9.5 mmol) was added to a solution of intermediate 14 (200 mg, 0.475 mmol) in ACN (2 mL). The mixture was heated at 90° C. in a sealed tube for 3 hours. The reaction mixture was cooled to room temperature and poured out into ice water and EtOAc. The mixture was extracted with EtOAc. The organic layer was dried (MgSO$_4$), filtered and the solvent was evaporated. The residue (325 mg) was purified by chromatography over silica gel [(Sunfire Silica, 5 μm, 150×30.0 mm), mobile phase (Gradient from 0% NH$_4$OH, 100% DCM, 0% MeOH to 0.5% NH$_4$OH, 95% DCM, 5% MeOH)], yielding 145 mg of product fraction (63%) which was crystallized with ACN/Et$_2$O. The precipitate was filtered, washed with Et$_2$O and dried to give 118 mg of compound 14 (51%, white solid). m.p.=145° C.

Example B14

Preparation of Compound 15 (Z)

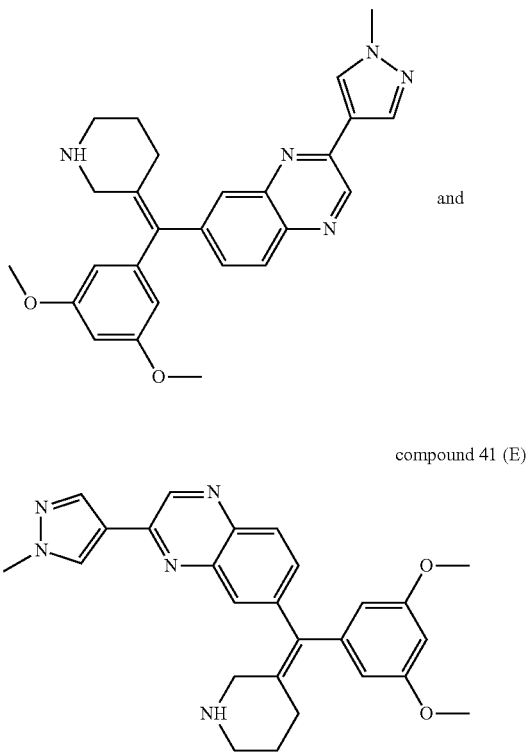

compound 41 (E)

3M HCl (5 mL) was added to a solution of intermediate 18 (0.375 g; 0.69 mmol) in MeOH (12 mL) at room temperature. The reaction mixture was heated at 60° C. for 6 hours. After cooling down to room temperature, the crude mixture was made basic with 10% K$_2$CO$_3$ aqueous solution and extracted twice with DCM. The combined organic layers were dried (MgSO$_4$), filtered and evaporated. The residue (340 mg) was purified by chromatography over silica gel [(Stability Silica, 5 μm, 150×30.0 mm), mobile phase (Gradient from 0.2% NH$_4$OH, 98% DCM, 2% MeOH to 1% NH$_4$OH, 90% DCM, 10% MeOH)] to give 46 mg of one fraction which was taken up into DCM and evaporated to give 45 mg (15%, isomer Z, m.p.=124° C. gum) of compound 15 and 77 mg of a second fraction which was taken up into DCM, and evaporated to give 70 mg (23%, isomer E, m.p.=130° C., gum) of compound 41.

Example B15

Preparation of Compound 27

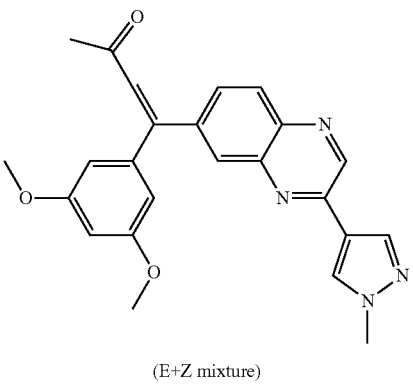 [SMILES: COc1cc(OC)cc(C(=CC(C)=O)c2ccc3ncc(-c4cnn(C)c4)nc3c2)c1]

(E+Z mixture)

7-Bromo-2-(1-methyl-1H-pyrazol-4-yl)-quinoxaline (8.76 g; 30.3 mmol), (3E)-4-(3,5-dimethoxyphenyl)-3-buten-2-one (5 g; 24.2 mmol), palladium(II) acetate (47% Pd) (272 mg; 1.2 mmol), tri-o-tolylphosphine (738 mg; 2.4 mmol) and TEA (10. mL; 72.7 mmol) in ACN (35 mL) were stirred at reflux (80° C.) for 48 hours. After cooling down to room temperature, water was added. The reaction mixture was filtered through a pad of Celite®. Celite® was washed with DCM. The organic layer was separated, dried (MgSO$_4$), filtered and evaporated. The residue (13.8 g) was purified by chromatography over silica gel [(Irregular SiOH, 20-45 μm, 450 g), mobile phase (0.1% NH$_4$OH, 98% DCM, 2% iPrOH)], yielding 3.4 g of residue. This residue was purified by chiral SFC [(CHIRALPAK IC, 5 μm, 250×20 mm), mobile phase (50% CO$_2$, 25% EtOH, 25% iPrOH)], yielding 2.1 g of compound 27 (21%, a yellow oil).

C. Conversion Reactions

Example C1

Preparation of Compound 17

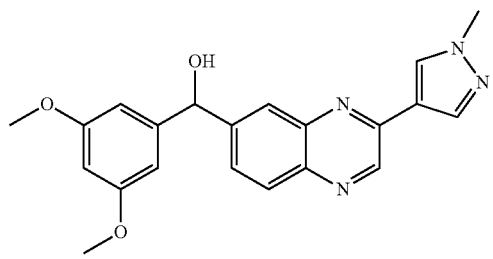 [SMILES: COc1cc(OC)cc(C(O)c2ccc3ncc(-c4cnn(C)c4)nc3c2)c1]

Sodiumborohydride (414 mg; 10.95 mmol) was added portionwise to a solution of compound 2 (2.05 g; 5.5 mmol) in MeOH (15 mL) and THF (5 mL) at 5° C. The reaction mixture was allowed to stir at room temperature for 40 minutes. Water was added. The reaction mixture was stirred for 10 minutes. The precipitate was filtered off yielding 1.74 g (84%) of compound 17.

Example C2

Preparation of Compound 18

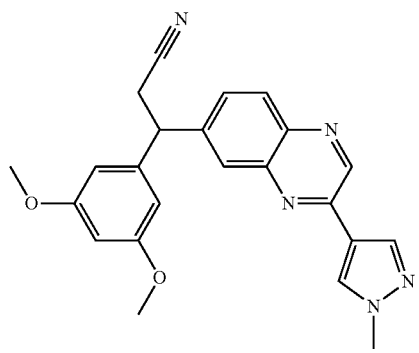 [SMILES: COc1cc(OC)cc(C(CC#N)c2ccc3ncc(-c4cnn(C)c4)nc3c2)c1]

Magnesium (1.7 g; 71.3 mmol) was added to a suspension of compound B3 (2.7 g; 6.8 mmol) in MeOH (70 mL) and THF (40 mL). The reaction mixture was stirred for 3.5 hours. The temperature raised to 35° C. The reaction mixture was cooled down to 10° C. and stirred for 1 hour. Ice and 10% aqueous NH$_4$Cl solution were added. The reaction mixture was extracted with DCM, dried (MgSO$_4$), filtered and evaporated. The residue was purified by chromatography over silica gel [(Irregular SiOH, 15-40 µm, 300 g), mobile phase (0.1% NH$_4$OH, 98% DCM, 2% MeOH)] to give 2.6 g of product fraction which was crystallized from ACN, filtered and dried to give 1.51 g (56%) of compound 18, m.p.=165° C.

Example C2a

Preparation of Compound 16

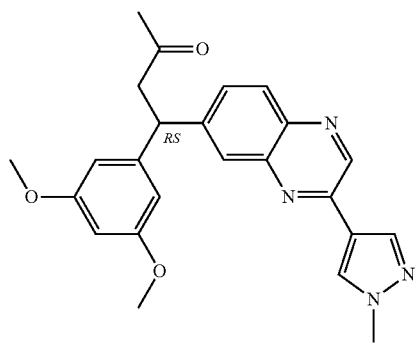 [SMILES: COc1cc(OC)cc(C(CC(C)=O)c2ccc3ncc(-c4cnn(C)c4)nc3c2)c1]

Magnesium turnings (1.36 g, 55.7 mmol) was added in one portion to a solution of compound 27 (2.1 g, 5.1 mmol) in MeOH (80 mL) at room temperature. The reaction mixture was stirred overnight. Ice and 10% aqueous NH$_4$Cl solution were added. The reaction mixture was extracted with DCM, dried (MgSO$_4$), filtered and the solvent was partially evaporated. Air was bubbled in the solution. Pd/C 10% (0.4 g) was added and air was bubbled for 1 day. The mixture was filtered through a pad of Celite®. Celite® was washed with CH$_2$Cl$_2$. The filtrate was evaporated. The residue (2.07 g) was purified by chromatography over silica gel [(Irregular SiOH, 15-40 µm, 300 g), mobile phase (0.1% NH$_4$OH, 97.5% DCM, 2.5% MeOH)], yielding 1 g of compound 16 (47%, orange solid, m.p.=154° C.).

Example C3

Preparation of

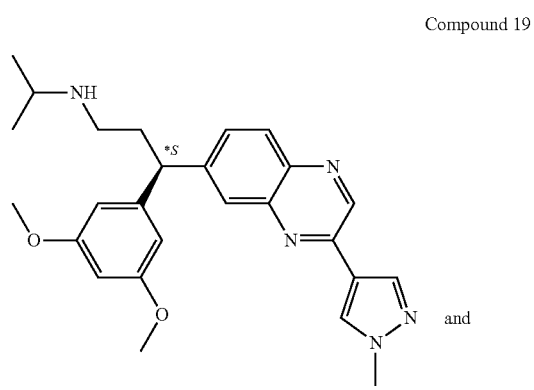

Compound 19 and

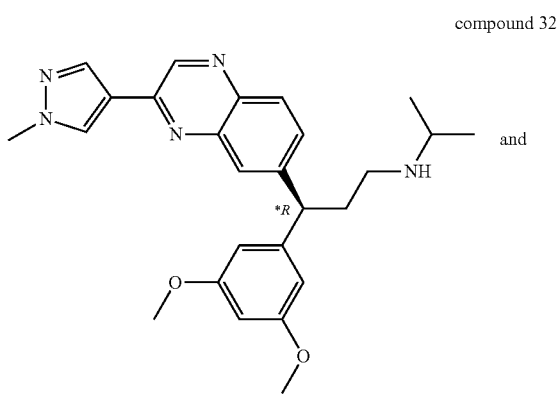

compound 32 and

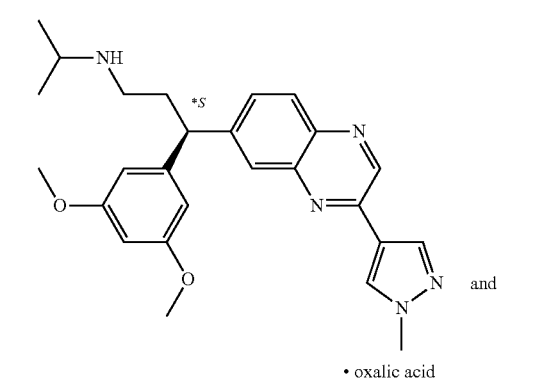

Compound 19a and

• oxalic acid

-continued compound 32a

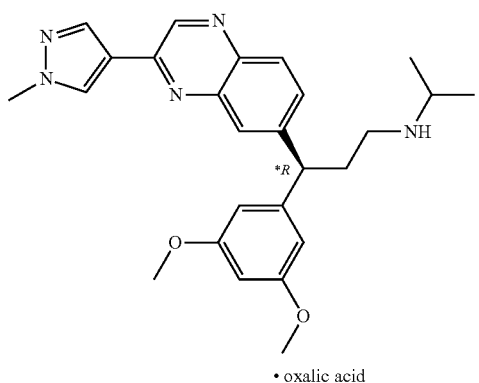

• oxalic acid

Methanesulfonylchloride (574 μL; 7.4 mmol) was added to a solution of compound 22 (1 g; 2.5 mmol) and TEA (1.4 mL, 9.9 mmol) in ACN (3 mL) at 5° C. under $N_2$. The reaction mixture was stirred for 1 hour at room temperature. Isopropylamine (16.8 mL) was added. The mixture heated at 90° C. in sealed tubes using one single mode microwave (Biotage Initiator EXP 60) with a power output ranging from 0 to 400 W for 60 minutes. The reaction mixture was evaporated. The residue was taken up into DCM and water. The organic layer was dried ($MgSO_4$), filtered and evaporated. The residue was purified by chromatography over silica gel [(Irregular SiOH, 20-45 μm, 450 g), mobile phase (0.5% $NH_4OH$, 92% DCM, 8% MeOH)]. The fractions were collected and evaporated yielding 1.26 g of a residue which was further purified by chiral SFC [(CHIRALPAK AD-H, 5 μm, 250×20 mm), mobile phase (0.3% ISOPROPYLAMINE, 40% iPrOH, 60% $CO_2$)] to give 439 mg of one enantiomer (compound 19) and 470 mg of the other enantiomer (compound 32).

The first fraction (439 mg) was converted into the HCl salt in MeOH. $Et_2O$ was added. The precipitate was filtered off and dried to give 410 mg of a solid product. Because of some degradation, this product was basified with a mixture of ice water and 10% aqueous $K_2CO_3$ solution. DCM was added and the organic layer was separated, dried ($MgSO_4$) and the solvent was evaporated, yielding 440 mg of residue. The residue was purified by chromatography over silica gel [(Sunfire Silica, 5 μm, 150×30.0 mm), mobile phase (Gradient from 0.2% $NH_4OH$, 98% DCM, 2% MeOH to 1.3% $NH_4OH$, 87% DCM, 13% MeOH)]. The pure fractions were collected and the solvent was evaporated to give 315 mg of compound 19 (optical rotation=+20.7 (589 nm, c=0.28, DMF, 20° C.). This compound was converted into its oxalic acid salt in EtOH. The precipitate was filtered off and dried to give 255 mg (18%) of compound 19a, m.p.=162° C.

The second fraction (470 mg) was converted into the HCl salt in MeOH. $Et_2O$ was added. The precipitate was filtered off and dried to give 400 mg of a solid product. Because of some degradation, this product and its filtrate were gathered and basified with a mixture of ice water and 10% aqueous $K_2CO_3$ solution. DCM was added and the organic layer was separated, dried ($MgSO_4$) and the solvent was evaporated, yielding 440 mg of residue. The residue was purified by chromatography over silica gel [(Sunfire Silica, 5 μm, 150×30.0 mm), mobile phase (Gradient from 0.2% $NH_4OH$, 98% DCM, 2% MeOH to 1.3% $NH_4OH$, 87% DCM, 13% MeOH)]. The pure fractions were collected and the solvent was evaporated to give 276 mg of compound 32 (optical rotation=−22.7 (589 nm, c 0.26, DMF, 20° C.) which was converted into its oxalic acid salt in EtOH. The precipitate was filtered off and dried to give 217 mg (16%) of compound 32a. m.p.=172° C.

* means relative stereochemistry

Example C4 a) Preparation of Compound 20

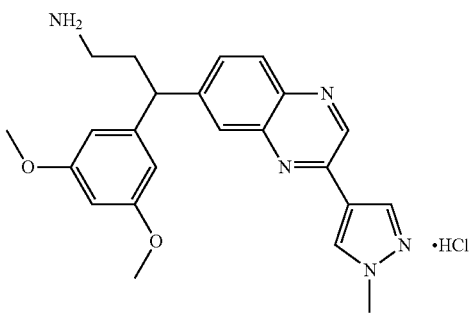 [SMILES: COc1cc(OC)cc(C(CCN)c2ccc3ncc(-c4cnn(C)c4)nc3c2)c1 ; Cl]

A solution of compound 18 (1.1 g; 2.75 mmol) was hydrogenated at room temperature in ammonia 7N in MeOH (250 mL) and THF (50 mL) with Raney Nickel (1.13 g) as a catalyst in a (Parr®) pressure vessel reactor (2 bar). Air was bubbled into the mixture for 4 hours. The catalyst was filtered off on a pad of Celite®. The filtrate was evaporated.

The residue was purified by chromatography over silica gel [(Irregular SiOH, (15-40 μm, 90 g), mobile Phase (Gradient from 100% DCM, 0% MeOH to 85% DCM, 15% MeOH)]. The pure fractions were collected and evaporated to dryness. The desired fractions were combined (790 mg), dissolved in MeOH and converted into the hydrochloric acid salt with HCl/2-propanol. The compound was crystallized from MeOH. The precipitate was stirred for 30 minutes, filtered off washed with $Et_2O$ and dried, yielding 792 mg (61%) of compound 20.

Example C5

Preparation of Compound 21

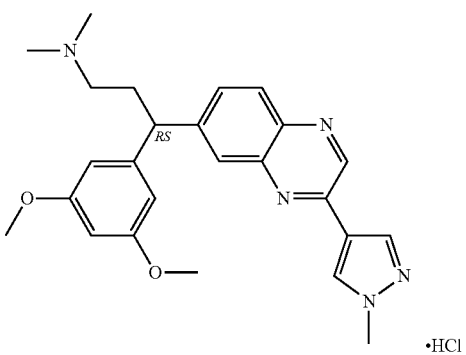

-continued

Compound 36

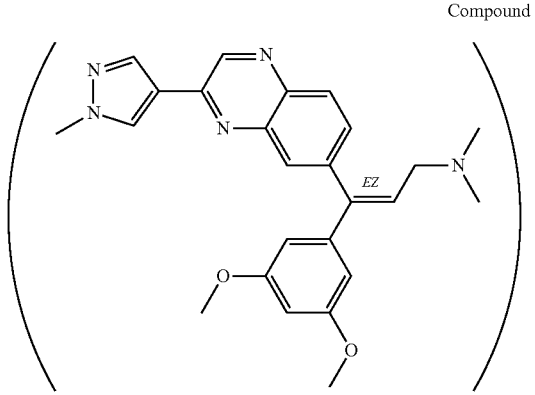

prepared according to protocol B13 (208 mg, 0.484 mmol) was hydrogenated at room temperature in MeOH (4 mL) with Pd (10% on dried carbon) (50 mg, 0.471 mmol) as a catalyst at atmospheric pressure. After 2 hours, the catalyst was filtered off on a pad of Celite® Celite® was washed with CH$_2$Cl$_2$/MeOH. The filtrate was evaporated. The residue (180 mg) was purified by chromatography over silica gel [(Sunfire Silica, 5 μm, 150×30.0 mm), mobile phase (Gradient from 0.2% NH$_4$OH, 98% DCM, 2% MeOH to 1.2% NH$_4$OH, 88% DCM, 12% MeOH)], yielding 56 mg of product fraction which was converted into the HCl (5 eq.) salt in MeOH. Et$_2$O was added. The precipitate was filtered and dried to give 50 mg of compound 21 (21%).

Example C6 a) Preparation of Compound 22

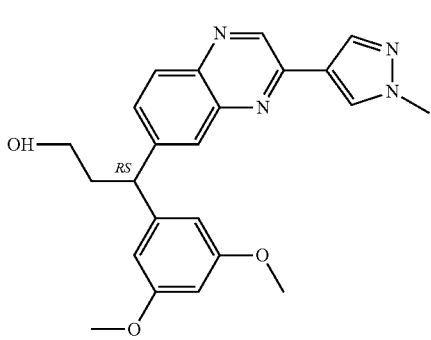 [SMILES: COc1cc(OC)cc(C(CCO)c2ccc3ncc(-c4cnn(C)c4)nc3c2)c1]

LiAlH$_4$ (434 mg; 11.4 mmol) was added to a solution of compound 13 (3.4 g; 7.6 mmol) in THF (55 mL) at 0-5° C. under nitrogen. The reaction mixture was stirred for 1 hour at 0-5° C. EtOAc was carefully added, followed by water. The mixture was filtered through a pad of Celite®. The organic layer was decanted, dried (MgSO$_4$), filtered and evaporated. The residue was purified by chromatography over silica gel [(Irregular SiOH, 15-40 μm, 300 g), mobile phase (0.1% NH$_4$OH, 3% MeOH, 97% DCM)], yielding 1.79 g (58%) of compound 22.

Example C7 a) Preparation of Compound 23

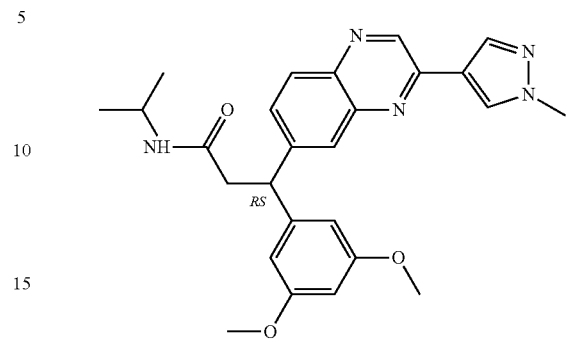

Compound 13 (400 mg; 0.9 mmol) and isopropylamine (3.4 mL; 40.3 mmol) in a sealed tube were heated at 135° C. using one single mode microwave (Biotage Initiator EXP 60) with a power output ranging from 0 to 400 W for 5 hours (12 bars). Then the reaction was stirred at 135° C. for 12 hours in an oil bath. After cooling down to room temperature, the solvent was evaporated. The residue was purified by chromatography over silica gel [(Sunfire Silica, 5 μm, 150×30.0 mm), mobile phase (Gradient from 0% NH$_4$OH, 100% DCM, 0% MeOH to 0.5% NH$_4$OH, 95% DCM, 5% MeOH)]. The desired product fraction (91 mg, 22%) was crystallized from Et$_2$O and filtered to give 52 mg (12%) of compound 23.
m.p.=186° C.

Example C8

Preparation of

Compound 24

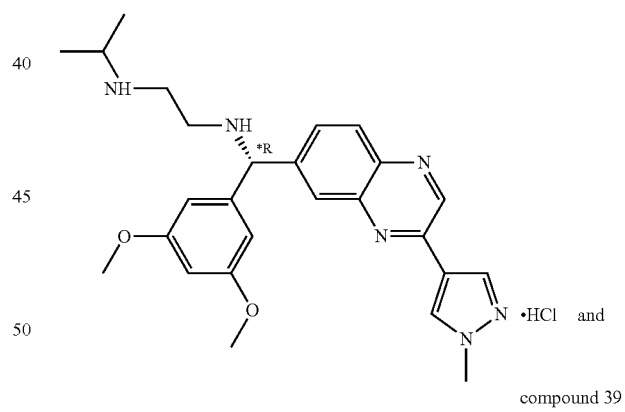

and compound 39

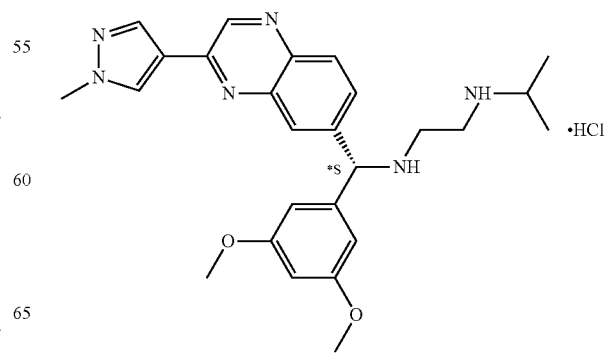

Compound 2 (814 mg; 2.17 mmol) and N-isopropylethylenediamine (98%) (3.6 mL; 28.3 mmol) were stirred at 140° C. for 7 hours, then at 60° C. overnight. After cooling down to 5° C., MeOH (15 mL) was added, then sodium borohydride (329 mg; 8.7 mmol) was added and the reaction mixture was stirred for 1 hour at 5° C. then at room temperature for 4 hours. Water was added and the crude mixture was extracted twice with DCM. The combined organic layers were washed with water, dried ($MgSO_4$), filtered and evaporated. The residue was purified by chromatography over silica gel [(Irregular SiOH, 20-45 μm, 450 g), mobile phase (0.5% $NH_4OH$, 95% DCM, 5% MeOH)] to give 675 mg of product fraction. The product fraction was purified by chiral SFC [(CHIRALPAK AD-H, 5 μm, 250×20 mm), mobile phase (0.3% ISOPROPYLAMINE, 70% $CO_2$, 15% EtOH, 15% iPrOH)]. The pure fractions were collected and the solvent was evaporated to give 240 mg of one enantiomer (first fraction), and 237 mg of the other enantiomer (second fraction).

The first fraction (240 mg) was converted into its HCl salt with HCl in iPrOH (5-6N) in ACN. The solvent was evaporated and the residue was taken up into $Et_2O$, filtered and dried to give 267 mg (22%) of compound 24.

The second fraction (237 mg) was converted into its HCl salt with HCl in iPrOH (5-6N) in ACN. The solvent was evaporated and the residue was taken up into $Et_2O$, filtered and dried to give 269 mg (22%) of compound 39.

* means relative stereochemistry

Example C9

Preparation of Compound 25

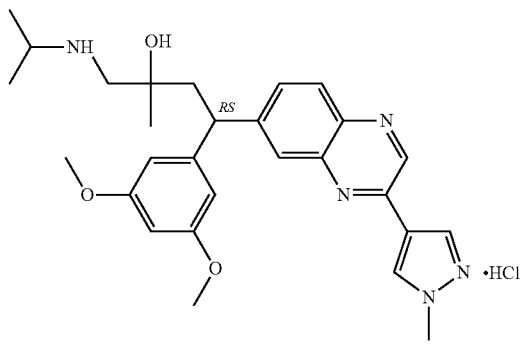 [SMILES: COc1cc(OC)cc(C(CC(C)(O)CNC(C)C)c2ccc3ncc(-c4cnn(C)c4)nc3c2)c1 ; Cl]

A mixture of compound 26 (180 mg; 0.418 mmol) (see Example C10) and isopropylamine (178 μL; 2.1 mmol) in DMF (3.5 mL) was heated at 100° C. for 20 hours. Isopropylamine (178 μL; 2.1 mmol) was added to the mixture. The reaction mixture was heated at 120° C. overnight. Isopropylamine (1 mL; 11.7 mmol) and ethanol (1 mL) were added. The mixture was heated at reflux overnight and then cooled to room temperature. Water was added and the mixture was extracted with EtOAc. The organic layer was dried ($MgSO_4$), filtered and evaporated. The residue was purified by chromatography over silica gel [(Sunfire Silica, 5 μm, 150×30.0 mm), mobile phase (Gradient from 0.2% $NH_4OH$, 98% DCM, 2% MeOH to 1.3% $NH_4OH$, 87% DCM, 13% MeOH)], yielding, after evaporation of collected fractions, 200 mg of a yellow oil which was converted into the HCl (5 eq.) salt in MeOH/ $Et_2O$. The solvent was evaporated to give 200 mg (87%) of compound 25.

Example C10

Preparation of Compound 26

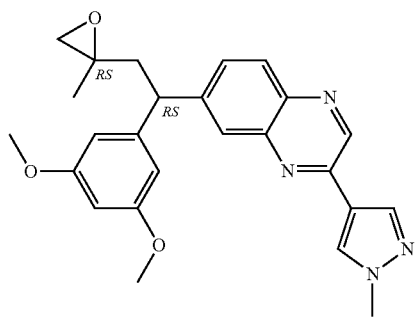 [SMILES: COc1cc(OC)cc(C(CC2(C)CO2)c2ccc3ncc(-c4cnn(C)c4)nc3c2)c1]

Potassium tert-butoxide (182 mg; 1.6 mmol) was added portionwise to a solution of trimethylsulphoxonium iodide (357 mg; 1.6 mmol) in dimethoxymethane (15 mL) at room temperature. The mixture was stirred at room temperature for 1 hour and the solution was added dropwise to a solution of compound 16 (450 mg; 1.08 mmol) in DMSO (6 mL) at 5° C. under $N_2$ flow. The reaction mixture was stirred at 5° C. for 1 hour then at room temperature for 48 hours. The reaction mixture was poured out into ice water and EtOAc was added. The organic layer was separated, washed with brine, dried ($MgSO_4$), filtered and the solvent was evaporated. The residue (473 mg) was purified by achiral SFC [(CYANO, 6 μm, 150×21.2 mm), mobile phase (90% $CO_2$, 10% MeOH)], yielding two fractions 140 mg (28%) and 180 mg (39%) of compound 26.

The following compounds were prepared according to reaction protocols of one of the above Examples using alternative starting materials as appropriate.

In the Table A1=CoX or =BX indicates that the preparation of this compound is described in Conversion X or Method BX.

In the Table A1~CoX or ~BX indicates that this compound is prepared according to Conversion X or Method BX.

In the Table A1 * means relative stereochemistry
TABLE A1
| Co. No. | | Method | Melting Point (°C.) | (Kofler (K) or DSC) | HPLC Rt (min) | MS M+ (H+) | LC/GC/MS method |
|---|---|---|---|---|---|---|---|
| 1 | 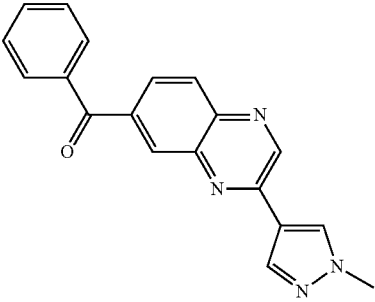 [SMILES: Cn1cc(-c2cnc3ccc(C(=O)c4ccccc4)cc3n2)cn1] | =B1 (B2) | | | | | |
| 28 | 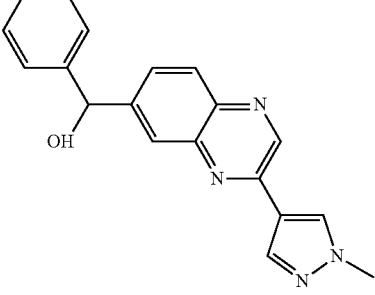 | ~Cl | | | 2.96 | 317 | Method 1 |
| 3 | 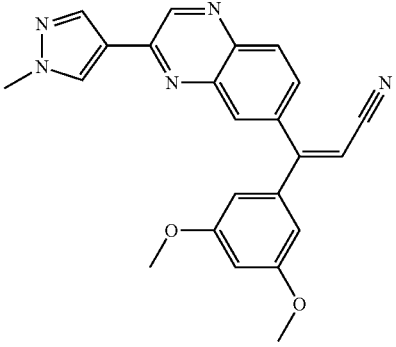 [SMILES: COc1cc(OC)cc(/C(=C/C#N)c2ccc3ncc(-c4cnn(C)c4)nc3c2)c1] | =B3 | 223 | DSC | 3.93 | 398 | Method 1 |
| 2 | 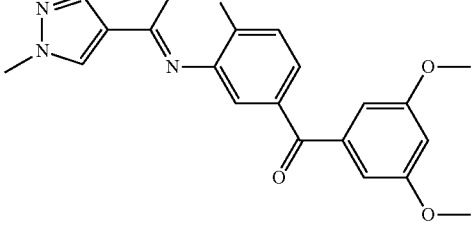 | =B2 and B5 | 162 | K | 3.55 | 375 | Method 1 |

TABLE A1-continued

| Co. No. | | Method | Melting Point (° C.) | (Kofler (K) or DSC) | HPLC Rt (min) | MS M+ (H+) | LC/GC/ MS method |
|---|---|---|---|---|---|---|---|
| 4 | | =B3 and B4 | 204 | DSC | 3.63 | 398 | Method 1 |
| 18 | | =C2 | 181 | DSC | 3.36 | 400 | Method 1 |
| 13 | | =B12 | | | | | |
| 22 | | =C6 | 114 | DSC | 3.03 | 405 | Method 1 |

TABLE A1-continued
| Co. No. | | Method | Melting Point (°C.) | (Kofler (K) or DSC) | HPLC Rt (min) | MS M+ (H+) | LC/GC/ MS method |
|---|---|---|---|---|---|---|---|
| 29 | 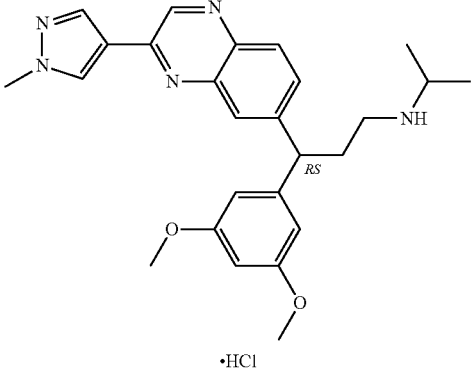 [SMILES: COc1cc(OC)cc(C(CCNC(C)C)c2ccc3ncc(-c4cnn(C)c4)nc3c2)c1 ; Cl] •HCl | ~C3 | 148 | K | 2.8 | 446 | Method 1 |
| 20 | 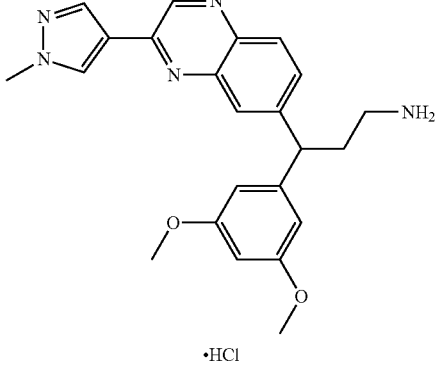 •HCl | =C4 | 211 | K | 2.58 | 404 | Method 1 |
| 7 | 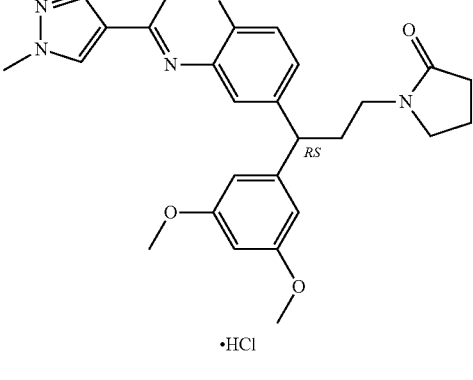 •HCl | =B7 | | | 3.16 | 472 | Method 1 |
| 30 | 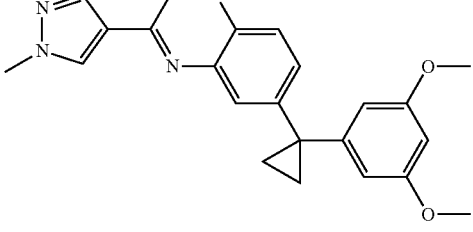 | ~B7 | 140 | K | | 387 | Method 1 |

TABLE A1-continued

| Co. No. | Method | Melting Point (° C.) | (Kofler (K) or DSC) | HPLC Rt (min) | MS M+ (H+) | LC/GC/ MS method |
|---|---|---|---|---|---|---|
| 31 | ~B12 | | | | | |
| 23 | =C7 | 186 | K | 3.14 | 460 | Method 1 |
| 27 (E + Z) | =B15 | | | | | |
| 16 | =C2a | | | | | |

TABLE A1-continued

| Co. No. | Method | Melting Point (° C.) | (Kofler (K) or DSC) | HPLC Rt (min) | MS M+ (H+) | LC/GC/ MS method |
|---|---|---|---|---|---|---|
| 19 | =C3 | | | | | |
| 19a •oxalic acid | =C3 | 163 | DSC | 2.79 | 446 | Method 1 |
| 32 | =C3 | | | | | |
| 32a •oxalic acid | =C3 | 172 | DSC | 2.81 | 446 | Method 1 |

TABLE A1-continued
| Co. No. | | Method | Melting Point (° C.) | (Kofler (K) or DSC) | HPLC Rt (min) | MS M+ (H+) | LC/GC/ MS method |
|---|---|---|---|---|---|---|---|
| 33 | 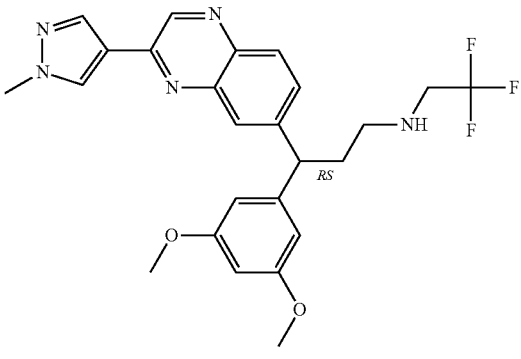 | ~C3 | 162 | K | 3.74 | 486 | Method 1 |
| 26 | 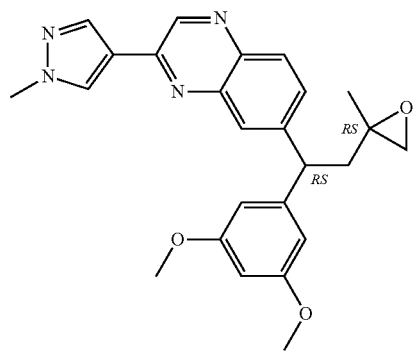 [SMILES: COc1cc(OC)cc(C(CC2(C)CO2)c2ccc3ncc(-c4cnn(C)c4)nc3c2)c1] | =C10 | | | | | |
| 34 | 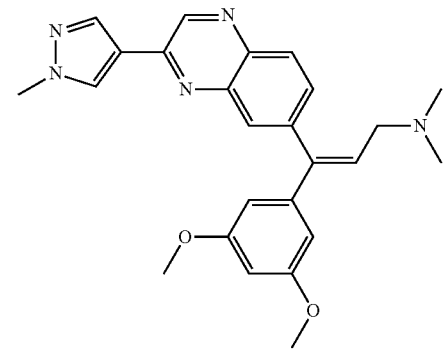 | =B9 | 177 | DSC | 2.86 | 430 | Method 2 |
| 10 | 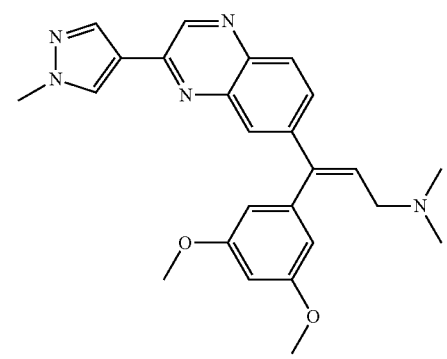 | =B9 | 164 | DSC | 2.89 | 430 | Method 2 |

TABLE A1-continued

| Co. No. | | Method | Melting Point (° C.) | (Kofler (K) or DSC) | HPLC Rt (min) | MS M+ (H+) | LC/GC/ MS method |
|---|---|---|---|---|---|---|---|
| 35 | | ~C5 | | | 2.58 | 372 | Method 2 |
| 11 | (Z) | =B10 | | | | | |
| 25 | ·HCl | =C9 | | | 2.66 | 490 | Method 1 |
| 9 | (E) ·HCl | =B8b | | | 2.84 | 444 | Method 1 |

TABLE A1-continued

| Co. No. | Structure | Method | Melting Point (°C.) | (Kofler (K) or DSC) | HPLC Rt (min) | MS M+ (H+) | LC/GC/MS method |
|---|---|---|---|---|---|---|---|
| 14 | (Z) | =B13 | 144 | DSC | 3.8 | 385 | Method 1 |
| 8 | (Z) | =B8a | | | 2.83 | 444 | Method 1 |
| 36 | EZ | ~B13 | | | | | |
| 17 | | =C1 | | | | | |

TABLE A1-continued

| Co. No. | Structure | Method | Melting Point (°C.) | (Kofler (K) or DSC) | HPLC Rt (min) | MS M+ (H+) | LC/GC/ MS method |
|---|---|---|---|---|---|---|---|
| 12 | | =B11 | | | | | |
| 21 | | =C5 | | | 2.66 | 432 | Method 1 |
| 37 | | ~B6 | 174 | K | 2.4 | 420 | Method 1 |
| 38 | | ~B6 | 169 | K | 2.4 | 420 | Method 1 |

TABLE A1-continued

| Co. No. | Method | Melting Point (°C.) | (Kofler (K) or DSC) | HPLC Rt (min) | MS M+ (H+) | LC/GC/MS method |
|---|---|---|---|---|---|---|
| 24 | =C8 | | | 2.66 | 461 | Method 1 |
| 39 | =C8 | | | 2.67 | 461 | Method 1 |
| 40 | ~C4 | 140 | K | 2.58 | 418 | Method 1 |
| 15 | =B14 | | | 2.64 | 442 | Method 1 |

TABLE A1-continued

| Co. No. | | Method | Melting Point (° C.) | (Kofler (K) or DSC) | HPLC Rt (min) | MS M+ (H+) | LC/GC/ MS method |
|---|---|---|---|---|---|---|---|
| 41 | 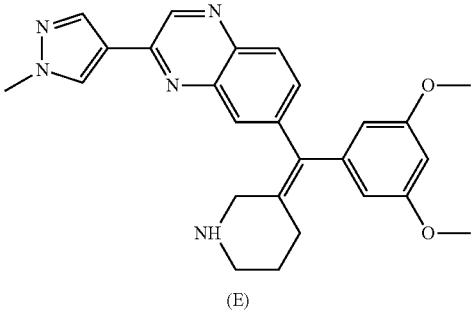 (E) | =B14 | | | 2.76 | 442 | Method 1 |
| 5 | 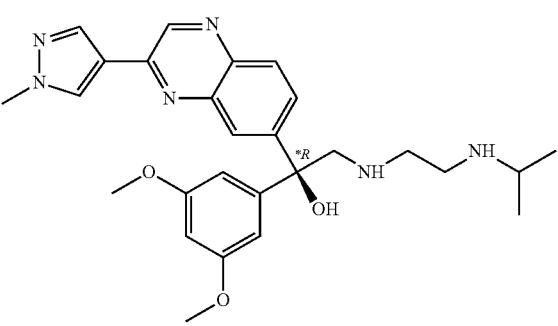 | =B6 | | | 2.59 | 491 | Method 1 |
| 6 | 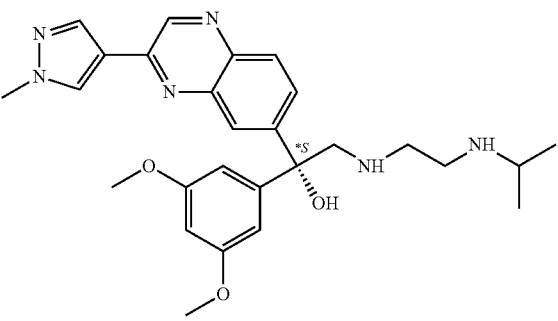 | =B6 | | | 2.59 | 491 | Method 1 |

Analytical Part
LC/GC/NMR
General Procedure A

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.
Method 1

In addition to the general procedure A: Reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

General Procedure B

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray mass spectrometer from Waters). Nitrogen was used as the nebulizer gas. Data acquisition was performed with a Waters-Micromass MassLynx-Openlynx data system.

Method 2

In addition to the general procedure B: Reversed phase HPLC was carried out on a Supelco Ascentis Express C18 column (2.7 μm, 3.0×50 mm) with a flow rate of 0.7 ml/min. Two mobile phases (mobile phase A: 100% 7 mM ammonium acetate; mobile phase B: 100% acetonitrile) were employed to run a gradient condition from 80% A and 20% B (hold for 0.5 minute) to 5% A and 95% B in 2.5 minutes, hold for 4.5 minutes and back to the initial conditions in 1.5 minutes and hold for 1 min. An injection volume of 5 μl was used. Cone voltage was 20 V for positive and negative ionization mode. Mass spectra were acquired by scanning from 100 to 1000 in 0.4 seconds using an interscan delay of 0.3 seconds.

NMR Data

The below NMR experiments were carried out using a Bruker Avance 500 and a Bruker Avance DRX 400 spectrometers at ambient temperature, using internal deuterium lock and equipped with reverse triple-resonance ($^1$H, $^{13}$C, $^{15}$N TXI) probe head for the 500 MHz and with reverse double-resonance ($^1$H, $^{13}$C, SEI) probe head for the 400 MHz. Chemical shifts (δ) are reported in parts per million (ppm).

Compound 19a $^1$H NMR (DMSO-$d_6$) δ: 9.24 (s, 1H), 8.55-8.82 (m, 3H), 8.26 (s, 1H), 7.96 (d, J=8.6 Hz, 1H), 7.92 (s, 1H), 7.68 (dd, J=8.6, 1.5 Hz, 1H), 6.57 (d, J=2.0 Hz, 2H), 6.36-6.40 (m, 1H), 4.28 (t, J=7.6 Hz, 1H), 3.95 (s, 3H), 3.72 (s, 6H), 3.24-3.37 (m, 1H), 2.84 (br. s., 2H), 2.38-2.47 (m, 2H), 1.17 (d, J=6.1 Hz, 6H)

Compound 10

$^1$H NMR (DMSO-$d_6$) δ: 9.23 (s, 1H), 8.61 (s, 1H), 8.25 (s, 1H), 7.96 (d, J=8.8 Hz, 1H), 7.86 (dd, J=8.8, 1.9 Hz, 1H), 7.51 (d, J=1.9 Hz, 1H), 6.57 (t, J=2.2 Hz, 1H), 6.47 (t, J=6.6 Hz, 1H), 6.35 (d, J=2.2 Hz, 2H), 3.92 (s, 3H), 3.75 (s, 6H), 2.96 (d, J=6.6 Hz, 2H), 2.16 (s, 6H)

Compound 14

$^1$H NMR (DMSO-$d_6$) δ: 9.23 (s, 1H), 8.61 (s, 1H), 8.25 (s, 1H), 7.98 (d, J=8.8 Hz, 1H), 7.81 (dd, J=8.8, 1.9 Hz, 1H), 7.55 (d, J=1.9 Hz, 1H), 6.56 (t, J=2.0 Hz, 1H), 6.45 (t, J=6.6 Hz, 1H), 6.38 (d, J=2.0 Hz, 2H), 3.92 (s, 3H), 3.75 (s, 6H), 3.17-3.32 (m, 4H), 2.65-2.75 (m, 1H)

Compound 8

$^1$H NMR (DMSO-$d_6$) δ: 9.22 (s, 1H), 8.61 (s, 1H), 8.25 (s, 1H), 7.96 (d, J=8.8 Hz, 1H), 7.80 (dd, J=8.8, 1.3 Hz, 1H), 7.53 (d, J=1.3 Hz, 1H), 6.56 (br. s, 1H), 6.46 (t, J=6.6 Hz, 1H), 6.38 (d, J=1.9 Hz, 2H), 3.92 (s, 3H), 3.75 (s, 6H), 3.21 (d, J=6.6 Hz, 2H), 2.69-2.78 (m, 1H), 1.76 (br. s, 1H), 0.93 (d, J=6.3 Hz, 6H)

Compound 29

$^1$H NMR (DMSO-$d_6$) δ: 9.25 (s, 1H), 8.72-9.00 (m, 2H), 8.62 (s, 1H), 8.27 (s, 1H), 7.96 (d, J=8.5 Hz, 1H), 7.92 (br. s., 1H), 7.68 (d, J=8.5 Hz, 1H), 6.58 (br. s., 2H), 6.38 (br. s., 1H), 4.33 (t, J=7.3 Hz, 1H), 3.95 (s, 3H), 3.72 (s, 6H), 3.24-3.34 (m, 1H), 2.74-2.89 (m, 2H), 2.53-2.59 (m, 2H), 1.19 (d, J=4.1 Hz, 6H)

Pharmacological Part
Biological Assays A
FGFR1 (Enzymatic Assay)

In a final reaction volume of 30 μL, FGFR1 (h) (25 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 5 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ (−log $IC_{50}$) value.

FGFR2 (Enzymatic Assay)

In a final reaction volume of 30 μL, FGFR2 (h) (150 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 0.4 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in (Relative Fluorescence Units). In this assay, the inhibitory effect of different compound concentrations (range 10 μM to 0.1 nM) was determined and used to calculate an $IC_{50}$ (M) and $pIC_{50}$ (−log $IC_{50}$) value.

FGFR3 (Enzymatic Assay)

In a final reaction volume of 30 μL, FGFR3 (h) (40 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 25 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ (−log $IC_{50}$) value.

FGFR4 (Enzymatic Assay)

In a final reaction volume of 30 μL, FGFR4 (h) (60 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 5 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ (−log $IC_{50}$) value.

KDR (VEGFR2) (Enzymatic Assay)

In a final reaction volume of 30 μL, KDR (h) (150 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 3 μM ATP in the presence of compound (1% DMSO final). After incubation for 120 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ (−log $IC_{50}$) value.

Ba/F3-FGFR1 (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR1-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluororescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value.

As a counterscreen the same experiment was performed in the presence of 10 ng/ml murine IL3.

Ba/F3-FGFR3 (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR3-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluororescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-KDR (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-KDR-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluororescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-Flt3 (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-Flt3-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluororescence plate reader.

In this assay, the inhibitory effect of different compound concentrations (range 10 μM to 0.1 nM) was determined and used to calculate an $IC_{50}$ (M) and $pIC_{50}$ (−log $IC_{50}$) value.

As a counterscreen the same experiment was performed in the presence of 10 ng/ml murine IL3.

$pIC_{50}$ Data for the compounds of the invention in the above assays are provided in Table A2.

TABLE A2

| Co. No. | FGFR1 | FGFR2 | FGFR3 | FGFR4 | VEGFR2 (KDR) | BAF3-FGFR1 (MIN IL3) | BAF3-FGFR1 (PLUS IL3) | BAF3-FGFR3 (MIN IL3) | BAF3-FGFR3 (PLUS IL3) | BAF3-KDR (MIN IL3) | BAF3-KDR (PLUS IL3) | BAF3-FLT3 (MIN IL3) | BAF3_FLT3 (PLUS IL3) |
|---|---|---|---|---|---|---|---|---|---|---|---|---|---|
| 28 | ~5.82 | 5.58 | 5.43 | 5.07 | 5.8 | <5 | <5 | <5 | <5 | <5 | <5 | <5 | <5 |
| 3 | 5.64 | 5.29 | 5.66 | <5 | 5.4 | <5 | <5 | 5.29 | <5 | <5 | <5 | <5 | <5 |
| 2 | 6.93 | 6.68 | 7.18 | ~5 | 6.15 | 5.58 | <5 | 5.17 | <5 | <5 | <5 | <5 | <5 |
| 4 | 7.27 | 6.99 | 7.44 | 6.44 | 6.18 | 5.3 | <5 | 5.76 | <5 | <5 | <5 | 5.29 | <5 |
| 18 | 7.14 | 6.84 | 7.36 | 6.74 | <6 | 5.6 | <5 | 5.48 | <5 | <5 | <5 | <5 | <5 |
| 22 | 6.97 | 6.9 | 7.29 | 6.29 | <6 | 5.66 | <5 | 5.65 | <5 | <5 | <5 | <5 | <5 |
| 29 | 7.64 | 7.59 | 7.45 | 6.56 | <6 | 6.18 | <5 | 6.44 | <5 | <5 | <5 | <5 | <5 |
| 20 | 7.11 | 7.17 | 7.21 | 6.35 | 5.33 | 5.86 | <5 | 6.04 | <5 | <5 | <5 | <5 | <5 |
| 7 | 7.25 | 7.42 | ~7.9 | 6.8 | 6.46 | 5.52 | <5 | 5.8 | <5 | 5.13 | <5 | <5 | <5 |
| 30 | 7.04 | 7.3 | 7.36 | 6.32 | 6.3 | 5.23 | <5 | 5.63 | <5 | <5 | <5 | <5 | <5 |
| 23 | <6 | <6 | <6 | <6 | <6 | <5 | <5 | <5 | <5 | <5 | <5 | <5 | <5 |
| 19a | 8.12 | 7.75 | 7.67 | 6.84 | <6 | 6.93 | <5 | 6.67 | <5 | <5 | <5 | <5 | <5 |
| 32a | 6.18 | 6.07 | ~6.04 | 5.26 | <5 | 5.14 | <5 | ~5.03 | <5 | <5 | <5 | <5 | <5 |
| 33 | 6.65 | 6.42 | 6.86 | ~6 | <6 | 5.11 | <5 | ~5.11 | <5 | <5 | <5 | <5 | <5 |
| 34 | 6.88 | 6.77 | 6.97 | <6 | <6 | 5.08 | <5 | ~5.13 | <5 | <5 | <5 | <5 | <5 |
| 10 | 7.77 | 7.8 | 8.04 | 6.97 | <6 | 5.81 | <5 | 6.27 | <5 | <5 | <5 | <5 | <5 |
| 35 | <6 | <6 | <6 | <6 | <6 | <5 | <5 | <5 | <5 | <5 | <5 | <5 | <5 |
| 25 | 6.1 | ~6 | 6.15 | <6 | 6.25 | <5 | <5 | 5.13 | <5 | <5 | <5 | <5 | <5 |
| 9 | 7.22 | 7.06 | 6.91 | 5.83 | 5.35 | 6.51 | <5 | 6.82 | <5 | <5 | <5 | ~5.05 | <5 |
| 14 | 7.86 | 7.89 | 8.33 | 7.54 | 6.61 | 6.17 | <5 | 6.39 | <5 | <5 | <5 | <5 | <5 |
| 8 | 8.11 | 7.97 | 8.06 | 6.9 | 6.41 | 6.49 | <5 | 6.72 | <5 | 5.18 | <5 | 5.09 | ~5.06 |
| 21 | 7.43 | 7.17 | 7.17 | 6.45 | <6 | 5.95 | <5 | 6.32 | <5 | <5 | <5 | <5 | <5 |
| 37 | ~6.05 | 6.23 | 6.27 | <6 | <6 | <5 | <5 | <5 | <5 | <5 | <5 | <5 | <5 |
| 38 | 6.11 | <6 | <6 | <6 | <6 | <5 | <5 | <5 | <5 | <5 | <5 | <5 | <5 |
| 24 | 6.74 | 6.49 | 6.59 | <6 | <6 | 5.16 | <5 | 5.29 | <5 | <5 | <5 | <5 | <5 |

TABLE A2-continued

| Co. No. | FGFR1 | FGFR2 | FGFR3 | FGFR4 | VEGFR2 (KDR) | BAF3-FGFR1 (MIN IL3) | BAF3-FGFR1 (PLUS IL3) | BAF3-FGFR3 (MIN IL3) | BAF3-FGFR3 (PLUS IL3) | BAF3-KDR (MIN IL3) | BAF3-KDR (PLUS IL3) | BAF3-FLT3 (MIN IL3) | BAF3_FLT3 (PLUS IL3) |
|---|---|---|---|---|---|---|---|---|---|---|---|---|---|
| 39 | <6 | <6 | <6 | <6 | <6 | <5 | <5 | <5 | <5 | <5 | <5 | <5 | <5 |
| 40 | 6.31 | 6.37 | 6.57 | <6 | <6 | 5 | <5 | 5.27 | <5 | <5 | <5 | <5 | <5 |
| 5 | 6.22 | ~6.13 | 6.24 | <6 | <6 | <5 | <5 | <5 | <5 | <5 | <5 | <5 | <5 |
| 6 | 6.02 | 6.09 | 6.17 | <6 | <6 | <5 | <5 | <5 | <5 | <5 | <5 | <5 | <5 |

Biological Assays B
FGFR3, VEGFR2 and PDGFR In Vitro Kinase Inhibitory Activity Assays Enzymes (from Upstate), prepared at 2× final concentration, were incubated with test compounds, biotinylated Flt3 substrate (biotin-VASSDNEYFYVDF) (Cell Signalling Technology Inc.) and ATP in the appropriate assay buffer (Table 1). The reaction was allowed to proceed for 3 hours (FGFR3), 1 hour (VEGFR2, PDGFR-beta) at room temperature on a plate shaker at 700 rpm before being stopped with 35 mM EDTA, pH 8 (FGFR3, VEGFR2) or 55 mM EDTA, pH 8 (PDGFR-beta). 5× detection mix (50 mM HEPES pH 7.5, 0.1% BSA, 11.34 nM Eu-anti-pY (PY20) (PerkinElmer) 74 nM SA-XL665 (Cisbio) for FGFR3, 50 mM HEPES, pH 7.5, 0.1% BSA, 11.34 nM Eu-anti-pY (PY20), 187.5 nM SA-XL665 for VEGFR2 and 50 mM HEPES, pH 7.5, 0.1% BSA, 11.34 nM Eu-anti-pY (PT66) (PerkinElmer), 375 nM SA-XL665 (Cisbio) for PDGFR-beta) was then added to each well and the plate sealed and incubated at room temperature for one hour on a plate shaker at 700 rpm. The plate was then read on a Packard Fusion plate reader or a BMG Pherastar both in TRF mode.

TABLE 1

Final assay conditions for FGFR3, VEGFR2 and PDGFR-beta assays

| Enzyme | 1 × Assay Buffer | Flt3 substrate concentration | ATP concentration |
|---|---|---|---|
| FGFR3 | A | 0.125 μM | 8 μM |
| VEGFR2 | B | 0.5 μM | 0.5 μM |
| PDGFR-beta | C | 1 μM | 70 μM |

Kinase Assay buffers were:
A: 50 mM HEPES pH 7.5, 6 mM MnCl$_2$, 1 mM DTT, 0.01% TritonX-100
B: 50 mM HEPES pH 7.5, 6 mM MnCl$_2$, 1 mM DTT, 0.01% TritonX-100, 0.1 mM Sodium orthovanadate
C: 20 mM HEPES pH 7.5, 10 mM MnCl$_2$, 0.01% Triton X-100, 1 mM DTT, 0.1 mM Sodium orthovanadate
FGFR3 and VEGFR2 Data for the compounds of the invention in the above assays are provided in Table A3.

Ba/F3-TEL-FGFR3 & Ba/F3 (WT) Cell Proliferation Assays

Stably transfected Ba/F3-TEL-FGFR3 cells were plated out into black 96-well tissue culture plates with clear bottoms in RPMI medium containing 10% FBS and 0.25 mg/ml G418 at a density of 5×10³ cells/well (200 μl per well). The parental wild-type Ba/F3 cells (DSMZ no.: ACC 300) were plated out into black 96-well tissue culture plates with clear bottoms in RPMI medium containing 10% FBS and 2 ng/ml mouse IL-3 (R&D Sysems) at a density of 2.5×10³ cells/well (200 μl per well). Plates were placed in an incubator overnight before adding the compounds the following day. Dilutions of compounds were made in DMSO starting at 10 mM and were diluted into the wells to give a final DMSO concentration of 0.1% in assay. Compounds were left on the cells for 72 hours before the plates were removed from the incubator and 20 μl of Alamar Blue™ (Biosource) was added to each well. Plates were placed in the incubator for 4-6 hours before reading plates at 535 nm (excitation)/590 nm (emission) on a Fusion plate reader (Packard). Where inhibition is high an IC$_{50}$ can be determined.

Data for the compounds of the invention in the above assays are provided in Table A3.

TABLE A3

| Compound number | FGFR3 pIC$_{50}$ | VEGFR2 pIC$_{50}$ | BAF3_TEL_FGFR3 pIC$_{50}$ | BAF3_WT pIC$_{50}$ |
|---|---|---|---|---|
| 18 | | 5.2 | | |
| 22 | | 5.4 | 6.85 | |
| 29 | 7.7 | 6.0 | 7.7 | 5.3 |
| 20 | | 5.5 | | |
| 30 | 7.7 | 6.55 | | |

The invention claimed is:
1. A compound selected from the group consisting of a compound of formula (I):

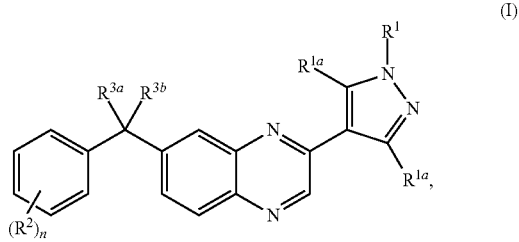

a tautomeric form, and stereochemically isomeric form thereof, wherein n represents 0, 1, 2, 3 or 4;

$R^1$ represents hydrogen, $C_{1-6}$alkyl, $C_{2-4}$alkenyl, hydroxyC$_{1-6}$alkyl, haloC$_{1-6}$alkyl, hydroxyhaloC$_{1-6}$alkyl, cyanoC$_{1-4}$alkyl, C$_{1-6}$alkoxyC$_{1-6}$alkyl wherein each C$_{1-6}$alkyl may optionally be substituted with one or two hydroxyl groups, C$_{1-6}$alkyl substituted with —NR$^4$R$^5$, C$_{1-6}$alkyl substituted with —C(=O)—NR$^4$R$^5$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$-C$_{1-6}$alkyl, C$_{1-6}$alkyl substituted with —NH—S(=O)$_2$-haloC$_{1-6}$alkyl, C$_{1-6}$alkyl substituted with —NR$^{12}$—S(=O)$_2$—NR$^{14}$R$^{15}$, R$^6$, C$_{1-6}$alkyl substituted with R$^6$, C$_{1-6}$alkyl substituted with —C(=O)—R$^6$, hydroxyC$_{1-6}$alkyl substituted with R$^6$, C$_{1-6}$alkyl substituted with —Si(CH$_3$)$_3$, C$_{1-6}$alkyl substituted with —P(=O)(OH)$_2$ or C$_{1-6}$alkyl substituted with —P(=O)(OC$_{1-6}$alkyl)$_2$;

each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms;

each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —NR$^7$R$^8$, $C_{1-4}$alkyl substituted with —C(=O)—NR$^7$R$^8$, $C_{1-4}$alkoxy substituted with —NR$^7$R$^8$, $C_{1-4}$alkoxy substituted with —C(=O)—NR$^7$R$^8$, —NR$^7$R$^8$ and —C(=O)—NR$^7$R$^8$; or when two $R^2$ groups are attached to adjacent carbon atoms they may be taken together to form a radical of formula:
—O—(C($R^{17}$)$_2$)$_p$—O—;
—X—CH=CH—; or
—X—CH=N—; wherein $R^{17}$ represents hydrogen or fluorine, p represents 1 or 2 and X represents O or S;

$R^{3a}$ represents —NR$^{10}$R$^{11}$, hydroxyl, $C_{1-6}$alkoxy, hydroxy$C_{1-6}$alkoxy, $C_{1-6}$alkoxy substituted with —NR$^{10}$R$^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —NR$^{10}$R$^{11}$, $C_{2-6}$alkenyl substituted with —NR$^{10}$R$^{11}$, $C_{2-6}$alkynyl substituted with —NR$^{10}$R$^{11}$, $C_{1-6}$alkyl substituted with hydroxyl and —NR$^{10}$R$^{11}$, $C_{1-6}$alkyl substituted with one or two halogens and —NR$^{10}$R$^{11}$, —$C_{1-6}$alkyl-C($R^{12}$)=N—O—$R^{12}$, $C_{1-6}$alkyl substituted with —C(=O)—NR$^{10}$R$^{11}$, $C_{1-6}$alkyl substituted with —O—C(=O)—NR$^{10}$R$^{11}$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NR$^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}$R$^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$;

$R^{3b}$ represents hydrogen or hydroxyl; provided that if $R^{3a}$ represents —NR$^{10}$R$^{11}$, then $R^{3b}$ represents hydrogen; or $R^{3a}$ and $R^{3b}$ are taken together to form =O, to form =NR$^{10}$, to form cyclopropyl together with the carbon atom to which they are attached, to form =CH—$C_{0-4}$alkyl substituted with $R^{3c}$, or to form

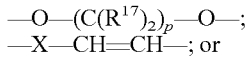

wherein ring A is a monocyclic 5 to 7 membered saturated heterocycle containing one heteroatom selected from N, O and S, said heteroatom not being positioned in alpha position of the double bond, wherein ring A is optionally being substituted with cyano, $C_{1-4}$alkyl, hydroxy$C_{1-4}$alkyl, H$_2$N—$C_{1-4}$alkyl, ($C_{1-4}$alkyl)NH—$C_{1-4}$alkyl, ($C_{1-4}$alkyl)$_2$N—$C_{1-4}$alkyl, halo$C_{1-4}$alkyl) NH—$C_{1-4}$alkyl, $C_{1-4}$alkoxy$C_{1-4}$alkyl, —C(=O)—NH$_2$, —C(=O)—NH($C_{1-4}$alkyl), —C(=O)—N($C_{1-4}$alkyl)$_2$;

$R^{3c}$ represents hydrogen, hydroxyl, $C_{1-6}$alkoxy, $R^9$, —NR$^{10}$R$^{11}$, cyano, —C(=O)—$C_{1-6}$alkyl or —CH(OH)—$C_{1-6}$alkyl;

$R^4$ and $R^5$ each independently represent hydrogen, $C_{1-6}$alkyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—NR$^{14}$R$^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O and S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —NR$^{14}$R$^{15}$, —C(=O)—NR$^{14}$R$^{15}$, $C_{1-6}$alkyl substituted with —NR$^{14}$R$^{15}$, $C_{1-6}$alkyl substituted with —C(=O)—NR$^{14}$R$^{15}$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—NR$^{14}$R$^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O and S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O and S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O and S;

$R^{10}$ and $R^{11}$ each independently represent hydrogen, carboxyl, $C_{1-6}$alkyl, cyano$C_{1-6}$alkyl, $C_{1-6}$alkyl substituted with —$NR^{14}R^{15}$, $C_{1-6}$alkyl substituted with —C(=O)—$NR^{14}R^{15}$, halo$C_{1-6}$alkyl, hydroxy$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —C(=O)—$R^6$, —C(=O)—$C_{1-6}$alkyl, —C(=O)-hydroxy$C_{1-6}$alkyl, —C(=O)-halo$C_{1-6}$alkyl,—C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O and S, wherein said $C_{3-8}$cycloalkyl or monocyclic heterocyclyl is optionally substituted with 1, 2 or 3 substituents each independently selected from halogen, hydroxyl, $C_{1-6}$alkyl, —C(=O)—$C_{1-6}$alkyl, $C_{1-6}$alkoxy, and —$NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino and mono-or di($C_{1-4}$alkyl)amino;

$R^{16}$ represents hydroxyl, halogen, cyano, $C_{1-4}$alkyl, $C_{1-4}$alkoxy, —$NR^{14}R^{15}$ or —C(=O)$NR^{14}R^{15}$;

or an N-oxide thereof or a pharmaceutically acceptable salt thereof.

2. A compound according to claim 1 wherein the compound is selected from the group consisting of a compound of formula (I°):

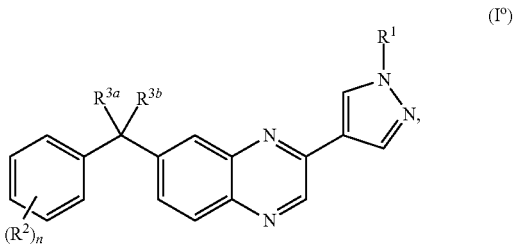

a tautomeric form, and stereochemically isomeric form thereof, wherein n represents 0, 1, 2, 3 or 4;

$R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;

each $R^2$ is independently selected from halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —$NR^7R^8$, $C_{1-4}$alkyl substituted with —C(=O)—$NR^7R^8$, $C_{1-4}$alkoxy substituted with —$NR^7R^8$, $C_{1-4}$alkoxy substituted with —C(=O)—$NR^7R^8$, —$NR^7R^8$ or —C(=O)—$NR^7R^8$;

$R^{3a}$ represents —$NR^{10}R^{11}$, hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo$C_{1-6}$alkyl, hydroxy$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups, $C_{2-6}$alkenyl substituted with $C_{1-6}$alkoxy, $C_{2-6}$alkynyl substituted with $C_{1-6}$alkoxy, $C_{1-6}$alkyl substituted with $R^9$, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$-$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$;

$R^{3b}$ represents hydrogen or hydroxyl; provided that if $R^{3a}$ represents —$NR^{10}R^{11}$, then $R^{3b}$ represents hydrogen; or $R^{3a}$ and $R^{3b}$ are taken together to form =O, to form =$NR^{10}$, to form cyclopropyl together with the carbon atom to which they are attached, to form =CH—$C_{0-4}$alkyl substituted with $R^{3c}$, or to form

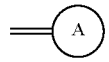

wherein ring A is a monocyclic 5 to 7 membered saturated heterocycle containing one heteroatom selected from N, O and S, said heteroatom not being positioned in alpha position of the double bond, wherein ring A is optionally being substituted with cyano, $C_{1-4}$alkyl, hydroxy$C_{1-4}$alkyl, $H_2N$—$C_{1-4}$alkyl, ($C_{1-4}$alkyl)NH—$C_{1-4}$alkyl, ($C_{1-4}$alkyl)N—$C_{1-4}$alkyl, halo$C_{1-4}$alkyl)NH—$C_{1-4\text{alkyl}}$, $C_{1-4}$alkoxy$C_{1-4}$alkyl, —C(=O)—$NH_2$, —C(=O)—NH($C_{1-4}$alkyl), —C(=O)—N($C_{1-4}$alkyl)$_2$;

$R^{3c}$ represents hydrogen, hydroxyl, $C_{1-6}$alkoxy, $R^9$, —$NR^{10}R^{11}$, cyano, —C(=O)—$C_{1-6}$alkyl or —CH(OH)—$C_{1-6}$alkyl;

$R^4$ and $R^5$ each independently represent hydrogen, $C_{1-6}$alkyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$-$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O and S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O and S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$-$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O and S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O and S;

$R^{10}$ and $R^{11}$ each independently represent hydrogen, $C_{1-6}$alkyl, cyano$C_{1-6}$alkyl, $C_{1-6}$alkyl substituted with —$NR^{14}R^{15}$, halo$C_{1-6}$alkyl, hydroxy$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —C(=O)—$R^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-haloC$_{1-6}$alkyl or C$_{1-6}$alkyl substituted with —NH—S(=O)$_2$—NR$^{14}$R$^{15}$;

R$^{12}$ represents hydrogen or C$_{1-4}$alkyl optionally substituted with C$_{1-4}$alkoxy;

R$^{13}$ represents C$_{3-8}$cycloalkyl or a saturated 4 to 6-membered monocyclic heterocyclyl containing at least one heteroatom selected from N, O and S, wherein said C$_{3-8}$cycloalkyl or monocyclic heterocyclyl is optionally substituted with 1, 2 or 3 substituents each independently selected from halogen, hydroxyl, C$_{1-6}$alkyl, —C(=O)—C$_{1-6}$, C$_{1-6}$alkoxy, and —NR$^{14}$R$^{15}$;

R$^{14}$ and R$^{15}$ each independently represent hydrogen, or haloC$_{1-4}$alkyl, or C$_{1-4}$alkyl optionally substituted with a substituent selected from hydroxyl, C$_{1-4}$alkoxy, amino and mono-or di(C$_{1-4}$alkyl)amino;

R$^{16}$ represents hydroxyl, halogen, cyano, C$_{1-4}$alkyl, C$_{1-4}$alkoxy, —NR$^{14}$R$^{15}$ or —C(=O)NR$^{14}$R$^{15}$;

or an N-oxide thereof or a pharmaceutically acceptable salt thereof.

3. A compound according to claim 1 wherein n represents 0, 1 or 2;

or an N-oxide thereof or a pharmaceutically acceptable salt thereof.

4. A compound according to claim 1 wherein R$^1$ is C$_{1-6}$alkyl;

or an N-oxide thereof or a pharmaceutically acceptable salt thereof.

5. A compound according to claim 1 wherein R$^2$ is C$_{1-4}$alkoxy;

or an N-oxide thereof or a pharmaceutically acceptable salt thereof.

6. A compound according to claim 1 wherein R$^{3a}$ is —NR$^{10}$R$^{11}$, hydroxyl, hydroxyC$_{1-6}$alkyl, cyanoC$_{1-6}$alkyl, C$_{1-6}$alkyl substituted with —C(=O)—C$_{1-6}$alkyl, C$_{1-6}$alkyl substituted with —C(=O)—O—C$_{1-6}$alkyl, C$_{1-6}$alkyl substituted with R$^9$, C$_{1-6}$alkyl substituted with —NR$^{10}$R$^{11}$, C$_{1-6}$alkyl substituted with hydroxyl and —NR$^{10}$R$^{11}$, C$_{1-6}$alkyl substituted with —C(=O)—NR$^{10}$R$^{11}$;

or an N-oxide thereof or a pharmaceutically acceptable salt thereof.

7. A compound according to claim 1 wherein R$^{3a}$ and R$^{3b}$ are taken together to form =O, to form cyclopropyl together with the carbon atom to which they are attached, to form =CH—C$_{0-4}$alkyl substituted with R$^{3c}$, or to form

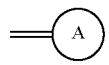

wherein ring A is a monocyclic 5 to 7 membered saturated heterocycle containing one heteroatom selected from N, O and S, said heteroatom not being positioned in alpha position of the double bond;

or an N-oxide thereof or a pharmaceutically acceptable salt thereof.

8. A compound according to claim 1 wherein R$^{3c}$ represents hydroxyl, —NR$^{10}$R$^{11}$, cyano, or —C(=O)—C$_{1-6}$alkyl;

or an N-oxide thereof or a pharmaceutically acceptable salt thereof.

9. A compound according to claim 1 wherein R$^9$ is a monocyclic heterocyclyl containing at least one heteroatom selected from N, O and S, said monocyclic heterocyclyl optionally being substituted with 1 substituent selected from =O and C$_{1-4}$alkyl;

or an N-oxide thereof or a pharmaceutically acceptable salt thereof.

10. A compound according to claim 1 wherein R$^{10}$ and R$^{11}$ each independently represent hydrogen, C$_{1-6}$alkyl, C$_{1-6}$alkyl substituted with —NR$^{14}$R$^{15}$ or haloC$_{1-6}$alkyl;

or an N-oxide thereof or a pharmaceutically acceptable salt thereof.

11. A compound according to claim 1 wherein R$^{14}$ and R$^{15}$ each independently represent hydrogen or C$_{1-4}$alkyl;

or an N-oxide thereof or a pharmaceutically acceptable salt thereof.

12. A compound as defined in claim 1 or a pharmaceutically acceptable salt thereof.

13. A compound according to claim 1 wherein the compound is selected from

{(Z)-3-(3,5-Dimethoxy-phenyl)-3-[3-(1-methyl-1H-pyrazol-4-yl)-quinoxalin-6-yl]-allyl}-dimethyl-amine;

{(Z)-3-(3,5-Dimethoxy-phenyl)-3-[3-(1-methyl-1H-pyrazol-4-yl)-quinoxalin-6-yl]-allyl}-isopropyl-amine;

{(Z)-3-(3,5-Dimethoxy-phenyl)-3-[3-(1-methyl-1H-pyrazol4-yl)-quinoxalin-6-yl]-allyl}-(2,2,2-trifluoro-ethyl)-amine;

{(S)-3-(3,5-Dimethoxy-phenyl)-3-[3-(1-methyl-1H-pyrazol-4-yl)-quinoxalin-6-yl]-propyl}-isopropyl-amine; and {3-(3,5-Dimethoxy-phenyl)-3-[3-(1-methyl-1H-pyrazol-4-yl)-quinoxalin-6-yl]-propyl}-isopropyl-amine;

or an N-oxide thereof or a pharmaceutically acceptable salt thereof.

14. A compound according to claim 13 or a pharmaceutically acceptable salt thereof.

15. A pharmaceutical composition comprising a pharmaceutically acceptable carrier and/or excipient, and a compound as defined in claim 1; or an N-oxide thereof or a pharmaceutically acceptable salt thereof.

16. A pharmaceutical composition comprising a pharmaceutically acceptable carrier and/or excipient, and a compound as defined in claim 13; or an N-oxide thereof or a pharmaceutically acceptable salt thereof.

17. A method for inhibiting a fibroblast growth factor receptor kinase, which method comprises contacting the kinase with a compound as defined in claim 1, or an N-oxide thereof or a pharmaceutically acceptable salt thereof.

18. A method according to claim 17, comprising contacting the kinase with a compound as defined in claim 1 or a pharmaceutically acceptable salt thereof.

19. A method for inhibiting a fibroblast growth factor receptor (FGFR) kinase, which method comprises contacting the kinase with a compound as defined in claim 13, or an N-oxide thereof or a pharmaceutically acceptable salt thereof.

20. A method according to claim 19, comprising contacting the kinase with a compound as defined in claim 13 or a pharmaceutically acceptable salt thereof.

* * * * *

UNITED STATES PATENT AND TRADEMARK OFFICE
CERTIFICATE OF CORRECTION

Page 1 of 1

PATENT NO.         : 9,290,478 B2
APPLICATION NO.    : 13/990193
DATED              : March 22, 2016
INVENTOR(S)        : Saxty et al.

It is certified that error appears in the above-identified patent and that said Letters Patent is hereby corrected as shown below:

In the Claims

Column 164, Lines 20-21: Claim 1, Delete "haloC$_{1-4}$alkyl)NH-C$_{1-4}$alkyl,"
and insert -- (haloC$_{1-4}$alkyl)NH-C$_{1-4}$alkyl, --

Column 167, Lines 42-43: Claim 2, Delete "haloC$_{1-4}$alkyl)NH-C$_{1-4alkyl}$, $_{C1-4}$alkoxyC$_{1-4}$alkyl,"
and insert -- (haloC$_{1-4}$alkyl)NH-C$_{1-4}$alkyl, C$_{1-4}$alkoxyC$_{1-4}$alkyl, --

Column 169, Line 11: Claim 2, Delete "-C(=O)-C$_{1-6}$, C$_{1-6}$alkoxy"
and insert -- -C(=O)-C$_{1-6}$alkyl, C$_{1-6}$alkoxy, --

Signed and Sealed this
Seventh Day of June, 2016

Michelle K. Lee
*Director of the United States Patent and Trademark Office*